US008586716B2

(12) United States Patent
Hsu et al.

(10) Patent No.: US 8,586,716 B2
(45) Date of Patent: Nov. 19, 2013

(54) EPHB3-SPECIFIC ANTIBODY AND USES THEREOF

(75) Inventors: Jeff Hsu, Pinole, CA (US); Linda Masat, Walnut Creek, CA (US); Judy Abraham, San Jose, CA (US); Masahisa Handa, Berkeley, CA (US); Siew Schleyer, Emeryville, CA (US)

(73) Assignees: Novartis AG, Basel (CH); Xoma Technology Ltd., Berkeley, CA (US)

( * ) Notice: Subject to any disclaimer, the term of this patent is extended or adjusted under 35 U.S.C. 154(b) by 1098 days.

(21) Appl. No.: 11/833,726

(22) Filed: Aug. 3, 2007

(65) Prior Publication Data

US 2009/0142261 A1 Jun. 4, 2009

Related U.S. Application Data

(60) Provisional application No. 60/835,777, filed on Aug. 4, 2006.

(51) Int. Cl.
*C07K 16/30* (2006.01)
*A61K 39/395* (2006.01)

(52) U.S. Cl.
USPC ............... 530/388.8; 530/387.3; 530/388.1; 530/391.1; 424/130.1; 424/133.1; 424/174.1; 424/178.1

(58) Field of Classification Search
None
See application file for complete search history.

(56) References Cited

U.S. PATENT DOCUMENTS

| | | |
|---|---|---|
| 30,985 A | 12/1860 | Pye |
| 3,773,919 A | 11/1973 | Boswell et al. |
| 4,179,337 A | 12/1979 | Davis et al. |
| 4,301,144 A | 11/1981 | Iwashita et al. |
| 4,419,446 A | 12/1983 | Howley et al. |
| 4,485,045 A | 11/1984 | Regen |
| 4,495,285 A | 1/1985 | Shimizu et al. |
| 4,496,285 A | 1/1985 | Albert et al. |
| 4,496,689 A | 1/1985 | Mitra |
| 4,544,545 A | 10/1985 | Ryan et al. |
| 4,560,655 A | 12/1985 | Baker |
| 4,601,978 A | 7/1986 | Karin |
| 4,609,546 A | 9/1986 | Hiratani et al. |
| 4,640,835 A | 2/1987 | Shimizu et al. |
| 4,657,866 A | 4/1987 | Kumar |
| 4,670,417 A | 6/1987 | Iwasaki et al. |
| 4,675,187 A | 6/1987 | Konishi et al. |
| 4,676,980 A | 6/1987 | Segal et al. |
| 4,766,106 A | 8/1988 | Katre et al. |
| 4,767,704 A | 8/1988 | Cleveland et al. |
| 4,791,192 A | 12/1988 | Nakagawa et al. |
| 4,816,567 A | 3/1989 | Cabilly et al. |
| 4,892,528 A | 1/1990 | Suzuki et al. |
| 4,927,762 A | 5/1990 | Darfler |
| 4,965,199 A | 10/1990 | Capon et al. |
| 4,975,278 A | 12/1990 | Senter et al. |
| 5,013,556 A | 5/1991 | Woodle et al. |
| 5,057,313 A | 10/1991 | Shih et al. |
| 5,122,469 A | 6/1992 | Mather et al. |
| 5,229,275 A | 7/1993 | Goroff |
| 5,283,187 A | 2/1994 | Aebischer et al. |
| 5,443,953 A | 8/1995 | Hansen et al. |
| 5,530,101 A | 6/1996 | Queen et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,585,089 A | 12/1996 | Queen et al. |
| 5,589,369 A | 12/1996 | Seidman et al. |
| 5,591,669 A | 1/1997 | Krimpenfort et al. |
| 5,624,821 A | 4/1997 | Winter et al. |
| 5,693,762 A | 12/1997 | Queen et al. |
| 5,766,866 A | 6/1998 | Center et al. |
| 5,766,886 A | 6/1998 | Studnicka et al. |
| 5,770,429 A | 6/1998 | Lonberg et al. |
| 5,877,293 A | 3/1999 | Adair et al. |
| 5,939,598 A | 8/1999 | Kucherlapati et al. |
| 6,054,287 A | 4/2000 | Gao et al. |
| 6,057,098 A | 5/2000 | Buechler et al. |
| 6,194,551 B1 | 2/2001 | Idusogie et al. |
| 6,306,393 B1 | 10/2001 | Goldenberg |
| 6,489,145 B1 | 12/2002 | Short |
| 6,605,449 B1 | 8/2003 | Short |
| 6,737,056 B1 | 5/2004 | Presta |
| 6,818,749 B1 * | 11/2004 | Kashmiri et al. ........ 530/388.85 |
| 2002/0004215 A1 | 1/2002 | Osbourn et al. |
| 2002/0091260 A1 | 7/2002 | Vasquez et al. |
| 2002/0199213 A1 | 12/2002 | Tomizuka et al. |
| 2003/0028071 A1 | 2/2003 | Handy et al. |

(Continued)

FOREIGN PATENT DOCUMENTS

| | | |
|---|---|---|
| EP | 0073657 | 3/1983 |
| EP | 0120694 | 10/1984 |

(Continued)

OTHER PUBLICATIONS

Paul, Fundamental Immunology, 3rd Edition, 1993. pp. 292-295.*
Rudikoff, Giusti, Cook, and Scharff. Single amino acid substitution altering antigen-binding specificity. Proceedings of the National Academy of Sciences, 1982. vol. 79, pp. 1979-1983.*
Colman. Research in Immunology, 1994. vol. 145, pp. 33-36.*
Mac Callum, Martin, and Thornton. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity-determining regions containing specificity-determining residues essential for ligand contact to engineer a less immunogenic humanized monoclonal antibody. Journal of Immunology, 2002. vol. 169, pp. 3076-3084.*

(Continued)

*Primary Examiner* — Sheela J Huff
*Assistant Examiner* — Jessica H Roark
(74) *Attorney, Agent, or Firm* — Marshall, Gerstein & Borun LLP

(57) ABSTRACT

EphB3-specific antibodies are provided, along with pharmaceutical compositions containing such antibody, kits containing a pharmaceutical composition, and methods of preventing and treating cancer.

20 Claims, 7 Drawing Sheets

(56) References Cited

U.S. PATENT DOCUMENTS

| | | |
|---|---|---|
| 2003/0031667 A1 | 2/2003 | Deo et al. |
| 2003/0032995 A1 | 2/2003 | Handy et al. |
| 2003/0092125 A1 | 5/2003 | Davis et al. |
| 2003/0118592 A1 | 6/2003 | Ledbetter et al. |
| 2003/0133939 A1 | 7/2003 | Ledbetter et al. |
| 2003/0190317 A1 | 10/2003 | Baca et al. |
| 2003/0194404 A1 | 10/2003 | Greenfeder et al. |
| 2004/0132101 A1 | 7/2004 | Lazar et al. |
| 2005/0037421 A1 | 2/2005 | Honda et al. |
| 2005/0136049 A1 | 6/2005 | Ledbetter et al. |
| 2006/0121042 A1* | 6/2006 | Dall'Acqua et al. ....... 424/155.1 |

FOREIGN PATENT DOCUMENTS

| | | |
|---|---|---|
| EP | 0125023 | 11/1984 |
| EP | 0171496 | 2/1986 |
| EP | 0173494 | 3/1986 |
| EP | 0194276 | 9/1986 |
| EP | 0315456 | 5/1989 |
| EP | 0404097 | 12/1990 |
| EP | 1400807 | 3/2004 |
| WO | WO-81/01145 | 4/1981 |
| WO | WO-86/01533 | 3/1986 |
| WO | WO-87/00195 | 1/1987 |
| WO | WO-87/05330 | 9/1987 |
| WO | WO-88/07278 | 9/1988 |
| WO | WO-90/13646 | 4/1990 |
| WO | WO-90/07861 | 7/1990 |
| WO | WO-91/09967 | 7/1991 |
| WO | WO-91/10741 | 7/1991 |
| WO | WO-91/11161 | 8/1991 |
| WO | WO-91/17271 | 11/1991 |
| WO | WO-92/01047 | 1/1992 |
| WO | WO-92/11018 | 7/1992 |
| WO | WO-93/19172 | 9/1993 |
| WO | WO-93/25673 | 12/1993 |
| WO | WO-94/02602 | 2/1994 |
| WO | WO-94/11026 | 5/1994 |
| WO | WO-95/15388 | 6/1995 |
| WO | WO-96/27011 | 9/1996 |
| WO | WO-96/30498 | 10/1996 |
| WO | WO-96/32478 | 10/1996 |
| WO | WO-96/33735 | 10/1996 |
| WO | WO-96/34096 | 10/1996 |
| WO | WO-97/34631 | 9/1997 |
| WO | WO-98/24893 | 6/1998 |
| WO | WO-99/58572 | 11/1999 |
| WO | WO-00/30673 | 6/2000 |
| WO | WO-02/092780 | 11/2002 |
| WO | WO-03/004057 A1 | 1/2003 |
| WO | WO-03/082608 A1 | 9/2003 |
| WO | WO 03072608 A1 * | 9/2003 |
| WO | WO-03/087841 | 10/2003 |
| WO | WO-2004/005457 | 1/2004 |
| WO | WO-2005/031002 A2 | 4/2005 |
| WO | WO-2006/047639 | 5/2006 |
| WO | WO-2006/132907 | 12/2006 |

OTHER PUBLICATIONS

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen binding site of an anti-ErbB2 antibody obtained with shotgun scanning mutagenesis. Journal of Molecular Biology, 2002. vol. 320, pp. 415-428.*
Holm, Jafari, and Sundstrom. Functional mapping and single chain construction of the anti-cytokeratin 8 monoclonal antibody TS1. Molecular Immunology, 2007. vol. 44, pp. 1075-1084.*
Chen, Wiesmann, Fuh, Li, Christinger, Mc Kay, De Vos, and Lowman. Selection and analysis of an optimized anti-VEGF antibody: crystal structure of an affinity-matured Fab in complex with antigen. Journal of Molecular Biology, 1999. vol. 293, pp. 865-881.*
Wu, Nie, Huse, and Watkins. Humanization of a murine monoclonal antibody by simultaneous optimization of framework and CDR residues. Journal of Molecular Biology, 1999. vol. 294, pp. 151-162.*
Skolnick and Fetrow. From genes to protein structure and function: novel applications of computational approaches in the genomic era. Trends in Biotechnology, 2000. vol. 18, pp. 34-39.*
Burgess, Shaheen, Ravera, Jaye, Donohue, and Winkles. Possible dissociation of the heparin binding and mitogenic activities of heparin-binding (acidic fibroblast) growth factor-1 from its receptor binding activities by site directed mutagenesis of a single lysine residue. Journal of Cell Biology, 1990. vol. 111, pp. 2129-2138.*
Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*
Muyldermans, Rev Mol Biotech 2001; 74:277-302.*
Brown et al., J. Immunol. 1996; 156(9):3285-91.*
Umeda et al., Am. J Ophthalmol 2004; 138:270-279.*
Adams et al., Roles of ephrinB ligands and EphB receptors in cardiovascular development: demarcation of arterial/venous domains, vascular morphogenesis, and sprouting angiogenesis. *Genes. Dev.* 13: 295-306 (1999).
Anderson, Human gene therapy. *Nature.* 392, Suppl. 6679: 25-30 (1998).
Angal et al., A single amino acid substitution abolishes the heterogeneity of chimeric mouse/human (IgG4) antibody. *Mol. Immunol.* 30: 105-8 (1993).
Aplin et al., Preparation, properties, and applications of carbohydrate conjugates of proteins and lipids. *CRC Crit. Rev. Biochem.* 259-306 (1981).
Armour et al., Differential binding to human FcgammaRIIa and FcgammaRIIb receptors by human IgG wildtype and mutant antibodies. *Mol. Immunol.* 40: 585-93 (2003).
Barnes et al., Methods for growth of cultured cells in serum-free medium. *Anal. Biochem.* 102: 255-70 (1980).
Bathe et al., EphB receptor activity suppresses colorectal cancer progression. *Nature.* 435: 1126-30 (2005).
Batra et al., Recombinant anti-erbB2 immunotoxins containing *Pseudomonas* exotoxin. *Proc. Natl. Acad. Sci. USA.* 89: 5867-71 (1992).
Bayer et al., The avidin-biotin complex in affinity cytochemistry. *Meth. Enzyme* 62: 308 (1979).
Becker et al., An antibody-interleukin 2 fusion protein overcomes tumor heterogeneity by induction of a cellular immune response. *Proc. Natl. Acad. Sci. USA.* 93: 7826-31 (1996).
Behr et al., Gene transfer with synthetic cationic amphiphiles: prospects for gene therapy. *Bioconjugate Chem.* 5: 382-9 (1994).
Behr, Efficient gene transfer into mammalian primary endocrine cells with lipopolyamine-coated DNA. Proc. Natl. Acad. Sci. USA. 86: 6982-6 (1989).
Behr, DNA strongly binds to micelles and vesicles containing lipopolyamines or lipointercalants. *Tetrahedron Lett.* 27: 5861-4 (1986).
Better et al., *Escherichia coli* secretion of an active chimeric antibody fragment. Science 240: 1041-3 (1988).
Better et al., Potent anti-CD5 ricin A chain immunoconjugates from bacterially produced Fab' and F(ab')2. *Proc. Natl. Acad. Sci. USA.* 90: 457-61 (1993).
Bianchi et al., Lac Z Histochemistry and immunohistochemistry reveal ephrin-B ligand expression in the inner ear. *J. Histchem. Cytochem.* 50: 1641-5 (2002).
Biocca et al., Expression and targeting of intracellular antibodies in mammalian cells. *EMBO J.* 9: 101-8 (1990).
Bird et al., Single-chain antigen-binding proteins. *Science.* 242: 423-6 (1988).
Bohme et al., Cell-cell adhesion mediated by binding of membrane-anchored ligand LERK-2 to the EPH-related receptor human embryonic kinase 2 promotes tyrosine kinase activity. *J. Biol. Chem.* 271: 24747-52 (1996).

(56) References Cited

OTHER PUBLICATIONS

Boleti et al., Construction, expression and characterisation of a single chain anti-tumour antibody (scFv)-IL-2 fusion protein. *Ann. Oncol.* 6: 945 (1995).
Boulianne et al., Production of functional chimaeric mouse/human antibody. *Nature.* 312: 643-6 (1984).
Brennan et al., Preparation of bispecific antibodies by chemical recombination of monoclonal immunoglobulin G1 fragments. *Science* 229: 81-3 (1985).
Brinkmann et al., B3(Fv)-PE38KDEL, a single-chain immunotoxin that causes complete regression of a human carcinoma in mice. *Proc. Natl. Acad. Sci. USA.* 88: 8616-20 (1991).
Brodeur et al., Monoclonal Antibody Production Techniques and Applications. Marcel Dekker, Inc., N.Y.: 51-63 (1987).
Bruggemann et al., Designer mice: the production of human antibody repertoires in transgenic animals. *Year in Immuno.* 7: 33-40 (1993).
Burton et al., Human antibodies from combinatorial libraries. *Adv. Immunol.* 57: 191-280 (1994).
Caron et al., Engineered humanized dimeric forms of IgG are more effective antibodies. *J. Exp. Med.* 176: 1191-5 (1992).
Carter et al., High level *Escherichia coli* expression and production of a bivalent humanized antibody fragment. *Bio/Technology.* 10: 163-7 (1992).
Caton et al., Influenza virus hemagglutinin-specific antibodies isolated from a combinatorial expression library are closely related to the immune response of the donor. *Proc. Natl. Acad. Sci. USA.* 87: 6450-4 (1990).
Champe et al., Monoclonal antibodies that block the activity of leukocyte function-associated antigen 1 recognize three discrete epitopes in the inserted domain of CD11a. *J. Biol. Chem.* 270: 1388-94 (1995).
Chappel et al., Identification of the Fc gamma receptor class I binding site in human IgG through the use of recombinant IgG1/IgG2 hybrid and point-mutated antibodies. *Proc. Natl. Acad. Sci. USA.* 88: 9036-40 (1991).
Chaudhary et al., A recombinant immunotoxin consisting of two antibody variable domains fused to *Pseudomonas* exotoxin. *Nature.* 339: 394-7 (1989).
Chothia et al., Canonical structures for the hypervariable regions of immunoglobulins. *J. Mol. Biol.* 196:901-17 (1987).
Chowdhury et al., Targeting random mutations to hotspots in antibody variable domains for affinity improvement. *Methods Mol. Biol.* 178,269-85 (2002).
Clackson et al., In vitro selection from protein and peptide libraries. *Trends Bitechnol.* 12: 173-84 (1994).
Conrath et al., Beta-lactamase inhibitors derived from single-domain antibody fragments elicited in the camelidae. *Antimicrob Agents Chemother.* 45: 2807-12 (2001).
Cotrez-Retamozo et al., Efficient cancer therapy with a nanobody-based conjugate. *Cancer Res.* 64: 2853-7 (2004).
Cunningham et al., High-resolution epitope mapping of hGH-receptor interactions by alanine-scanning mutagenesis. *Science.* 244: 1081-5 (1989).
Daugherty et al., Quantitative analysis of the effect of the mutation frequency on the affinity maturation of single chain Fv antibodies. *Proc. Natl. Acad. Sci. USA.* 97: 2029-34 (2000).
Desmyter et al., Antigen specificity and high affinity binding provided by one single loop of a camel single-domain antibody. *J. Biol. Chem.* 276: 26285-90 (2001).
Dohlsten et al., Monoclonal antibody-superantigen fusion proteins: tumor-specific agents for T-cell-based tumor therapy. *Proc. Natl. Acad. Sci. USA.* 91: 8945-50 (1994).
Edge et al., Deglycosylation of glycoproteins by trifluoromethanesulfonic acid. *Anal. Biochem.* 118: 131-7 (1981).
Engvall et al., Enzyme-linked immunosorbent assay, Elisa. 3. Quantitation of specific antibodies by enzyme-labeled anti-immunoglobulin in antigen-coated tubes. *Immunol.* 109: 129-35 (1972).
Eppstein et al., Biological activity of liposome-encapsulated murine interferon gamma is mediated by a cell membrane receptor. *Proc. Natl. Acad. Sci. USA.* 82: 3688-92 (1985).

Evan et al., Isolation of monoclonal antibodies specific for human c-myc proto-oncogene product. *Mol. Cell. Biol.* 5: 3610-6 (1985).
Ewert et al., Biophysical properties of camelid V(HH) domains compared to those of human V(H)3 domains. *Biochemistry.* 41: 3628-36 (2002).
Ferrara et al., The carbohydrate FcgammaRIIIa Asn-162. An element required for high affinity binding to non-fucosylated IgG glycoforms. *J. Biol. Chem.* 281: 5032-6 (2006).
Field et al., Purification of a RAS-responsive adenylyl cyclase complex from *Saccharomyces cerevisiae* by use of an epitope addition method. *Mol Cell. Biol.* 8: 2159-65 (1988).
Fishwild et al., High-avidity human IgG kappa monoclonal antibodies from a novel strain of minilocus transgenic mice. *Natl. Biotechol.* 14: 845-51 (1996).
Fleer et al., Stable multicopy vectors for high-level secretion of recombinant human serum albumin by *Kluyveromyces* yeasts. *Bio/Technology.* 9: 968-75 (1991).
Fominaya et al., Target cell-specific DNA transfer mediated by a chimeric multidomain protein. Novel non-viral gene delivery system. *J. Biol. Chem.* 271: 10560 (1996).
Friedmann et al., Antitumor activity of the single-chain immunotoxin BR96 sFv-PE40 against established breast and lung tumor xenografts. *J. Immunol.* 150: 3054 (1993).
Friedmann, Progress toward human gene therapy. *Science.* 244: 1275-81 (1989).
Gabizon et al., Pharmacokinetics and tissue distribution of doxorubicin encapsulated in stable liposomes with long circulation times. *J. Natl. Cancer Inst.* 81: 1484-8 (1989).
Goding et al., Conjugation of antibodies with fluorochromes: Modifications to the standard methods. . *J. Immunol. Meth.* 13: 215-26 (1976).
Goldenberg, New developments in monoclonal antibodies for cancer detection and therapy. *Cancer J. Clin.* 44: 43-63 (1994).
Graham et al., Characteristics of a human cell line transformed by DNA from human adenovirus type 5. *J. Gen. Virol.* 36: 59-74 (1977).
Greenberg et al., A new antigen receptor gene family that undergoes rearrangement and extensive somatic diversification in sharks. *Nature.* 374: 168-73 (1995).
Gruber et al., Efficient tumor cell lysis mediated by a bispecific single chain antibody expressed in *Escherichia coli. J. Immunol.* 152: 5368-74 (1994).
Guo et al., Reduced expression of EphB2 that parallels invasion and metastasis in colorectal tumours. *Carcinogenesis.* 27: 454-64 (2006).
Guss et al., Structure of the IgG-binding regions of streptococcal protein G. *EMBO J.* 5: 1567-75 (1986).
Ham et al., Media and growth requirements. *Methods Enzymol.* 58: 44-93 (1979).
Hamers-Casterman et al., Naturally occurring antibodies devoid of light chains. *Nature.* 363: 446-8 (1993).
Hank et al., Activation of human effector cells by a tumor reactive recombinant anti-ganglioside GD2 interleUkin-2 fusion protein (ch14.18-IL2). *Clin. Cancer. Res.* 2: 1951-9 (1996).
Hawkins et al., Selection of phage antibodies by binding affinity. Mimicking affinity maturation. *J. Mol. Biol.* 226: 889-96 (1992).
Helbling et al., The receptor tyrosine kinase EphB4 and ephrin-B ligands restrict angiogenic growth of embryonic veins in *Xenopus laevis. Development.* 127: 269-78 (2000).
Heng et al., Making cell-permeable antibodies (Transbody) through fusion of protein transduction domains (PTD) with single chain variable fragment (scFv) antibodies: potential advantages over antibodies expressed within the intracellular environment (Intrabody). *Med. Hypotheses.* 64: 1105-8 (2005).
Heroult et al., EPH receptor and ephrin ligand-mediated interactions during angiogenesis and tumor progression. *Exp. Cell. Res.* 312: 642-50 (2006).
Hollinger et al., "Diabodies": small bivalent and bispecific antibody fragments. *Proc. Natl. Acad. Sci. USA.* 90: 6444-8 (1993).
Hoogenboom et al., By-passing immunisation. Human antibodies from synthetic repertoires of germline Vh gene segments rearranged in vitro. *J. Mol. Biol.* 227: 381-8 (1991).
Hu et al., A chimeric Lym-1/interleukin 2 fusion protein for increasing tumor vascular permeability and enhancing antibody uptake. *Cancer Res.* 56: 4998-5004 (1996).

(56) References Cited

OTHER PUBLICATIONS

Huls et al., Tumor cell killing by in vitro affinity-matured recombinant human monoclonal antibodies. *Cancer Immunol. Immunother.* 50: 163-71 (2001).
Huston et al., Protein engineering of antibody binding sites: recovery of specific activity in an anti-digoxin single-chain Fv analogue produced in *Escherichia coli*. *Proc. Natl. Acad. Sci. USA.* 85: 5879-83 (1988).
Hwang et al., Hepatic uptake and degradation of unilamellar sphingomyelin/cholesterol liposomes: a kinetic study. *Proc. Natl. Acad. Sci. USA.* 77: 4030-4 (1980).
Isaacs et al., Therapy with monoclonal antibodies. II. The contribution of Fc gamma receptor binding and the influence of C(H)1 and C(H)3 domains on in vivo effector function. *J. Immunol.* 161: 3862-9 (1998).
Ishida et al., Production of human monoclonal and polyclonal antibodies in TransChromo animals. *Cloning Stem Cells.* 4: 91-102 (2002).
Jakobovits et al., Analysis of homozygous mutant chimeric mice: deletion of the immunoglobulin heavy-chain joining region blocks B-cell development and antibody production. *Proc. Natl. Acad. Sci. USA.* 90: 2551-5 (1993).
Jakobovits et al., Germ-line transmission and expression of a human-derived yeast artificial chromosome. *Nature.* 362: 255-8 (1993).
Jespers et al., Guiding the selection of human antibodies from phage display repertoires to a single epitope of an antigen. *Bio/Technology.* 12: 899-903 (1994).
Jones et al., Replacing the complementarity-determining regions in a human antibody with those from a mouse. *Nature.* 312: 522-5 (1986).
Kabat et al., Origins of antibody complementarity and specificity—hypervariable regions and minigene hypothesis. *J. Immunol.* 125: 961-9 (1980).
Kettleborough et al., Humanization of a mouse monoclonal antibody by CDR-grafting: the importance of framework residues on loop conformation. *Protein Eng.* 4: 773-83 (1991).
Kiyokawa et al., Overexpression of ERK, an EPH family receptor protein tyrosine kinase, in various human tumors. *Cancer Res.* 54: 3645-50 (1994).
Kohler et al., Continuous cultures of fused cells secreting antibody of predefined specificity. *Nature* 256: 495-7 (1975).
Kostelny et al., Formation of a bispecific antibody by the use of leucine zippers. *J. Immunol.* 148: 1547-53 (1992).
Kozbor, A human hybrid myeloma for production of human monoclonal antibodies. *J. Immunol.* 133: 3001-5 (1984).
Kuan et al., Recombinant immunotoxin containing a disulfide-stabilized Fv directed at erbB2 that does not require proteolytic activation. *Biochemistry.* 35: 2872 (1996).
Letsinger, Cholesteryl-conjugated oligonucleotides: synthesis, properties, and activity as. inhibitors of replication of human immunodeficiency virus in cell culture. *Proc. Natl. Acad. Sci. USA.* 86: 6553-6 (1989).
Leung et al., Engineering a unique glycosylation site for site-specific conjugation of haptens to antibody fragments. *J. Immunol.* 154: 5919 (1995).
Leventis et al., Interactions of mammalian cells with lipid dispersions containing novel metabolizable cationic amphiphiles. *Biochem . Biophys. Acta.* 1023: 124-32 (1990).
Linardou et al., Deoxyribonuclease I (DNAse I). A novel approach for targeted cancer therapy. *Cell Biophys.* 243: 24-5 (1994).
Lindmark et al., Binding of immunoglobulins to protein A and immunoglobulin levels in mammalian sera. *J. Immnol. Meth.* 62: 1-13 (1983).
Low et al., Mimicking somatic hypermutation: affinity maturation of antibodies displayed on bacteriophage using a bacterial mutator strain. *J. Mol. Biol.* 260: 359-68 (1996).
Malone et al., Cationic liposome-mediated RNA transfection. *Proc. Natl. Acad. Sci. USA.* 86: 6077-81 (1989).
Mao et al., EphB2 as a therapeutic antibody drug target for the treatment of colorectal cancer. *Cancer Res.* 64: 781-8 (2004).

Marks et al., By-passing immunization. Human antibodies from V-gene libraries displayed on phage. *J. Mol. Biol.* 222: 581-97 (1991).
Martin et al., Irreversible coupling of immunoglobulin fragments to preformed vesicles. An improved method for liposome targeting. *J. Biol. Chem.* 257: 286-8 (1982).
Maru et al., Overexpression confers an oncogenic potential upon the eph gene. *Oncogene.* 5: 445-7 (1990).
Massey, Catalytic antibodies catchin on. *Nature.* 328: 457-8 (1987).
Mather et al., Culture of testicular cells in hormone-supplemented serum-free medium. *Ann. N.Y. Acad. Sci.* 383: 44-68 (1982).
Mather et al., Establishment and characterization of two distinct mouse testicular epithelial cell lines. *Biol. Reprod.* 23: 243-51 (1980).
Mhashilkar et al., Inhibition of HIV-1 Tat-mediated LTR transactivation and HIV-1 infection by anti-Tat single chain intrabodies. *EMBO J.* 14: 1542-51 (1995).
Miller, Human gene therapy comes of age. *Nature.* 357: 455-60 (1992).
Morimoto et al., Single-step purification of F(ab')2 fragments of mouse monoclonal antibodies (immunoglobulins G1) by hydrophobic interaction high performance liquid chromatography using TSKgel Phenyl-5PW. *J. Biochem. Biophys. Methods.* 24: 107-17 (1992).
Morrison et al., Chimeric human antibody molecules; Mouse antigen binding domains with human constant region domains, *Proc. Natl. Acad. Sci. USA.* 81: 6851-55 (1984).
Morrison et al., Genetically engineered antibody molecules. *Adv. Immunol.* 44: 65-92 (1989).
Munson et al., Ligand: a versatile computerized approach for characterization of ligand-binding systems. *Anal. Biochem.* 107: 220-39 (1980).
Neri et al., High-affinity antigen binding by chelating recombinant antibodies (CRAbs). *J. Mol Biol.* 246: 367-73 (1995).
Neuberger et al., Recombinant antibodies possessing novel effector functions. *Nature.* 312: 604-8 (1984).
Nguyen et al., The specific variable domain of camel heavy-chain antibodies is encoded in the germline. *J. Mol. Biol.* 275: 413-8 (1998).
Nichimiya et al., Thermodynamic consequences of grafting enhanced affinity toward the mutated antigen onto an antibody. The case of anti-lysozyme antibody, HyHEL-10. *J. Biol. Chem.* 275: 12813-20 (2000).
Nicholls et al., Characterization of single-chain antibody (sFv)-toxin fusion proteins produced in vitro in rabbit reticulocyte lysate. *J. Biol. Chem.* 268: 5302-8 (1993).
Nuttall et al., Isolation of the new antigen receptor from wobbegong sharks, and use as a scaffold for the display of protein loop libraries. *Mol. Immunol.* 38: 313-26 (2001).
Ohmori et al., The enhancing effect of anionic alpha-helical peptide on cationic peptide-mediating transfection systems. *Biochem. Biophsy. Res. Commun.* 235: 726-9 (1997).
Olafsen et al., Characterization of engineered anti-p185HER-2 (scFv-CH3)2 antibody fragments (minibodies) for tumor targeting. *Protein Eng. Des. Sel.* 17: 315-23 (2004).
Paborsky et al., Mammalian cell transient expression of tissue factor for the production of antigen. *Protein Eng.* 3: 547-53 (1990).
Padlan, A possible procedure for reducing the immunogenicity of antibody variable domains while preserving their ligand-binding properties. *Molec. Immun.* 28: 489-98 (1991).
Padlan, Anatomy of the antibody molecule. *Molec. Immun.* 31: 169-217 (1994).
Pandey et al., Role of B61, the ligand for the Eck receptor tyrosine kinase, in TNF-alpha-induced angiogenesis. *Science* 268: 567-9 (1995).
Pastan et al., Immunotoxins. *Cell.* 47: 641-8 (1986).
Pinnaduwage et al., Use of a quaternary ammonium detergent in liposome mediated DNA transfection of mouse L-cells. *Biochim. Biophys. Acta.* 985: 33-7 1989.
Pluckthun, The Pharmacology of Monoclonal Antibodies, Springer-Verlag, N.Y. 1-13: 269-315 (1994).

(56) References Cited

OTHER PUBLICATIONS

Pollard et al., Polyethylenimine but not cationic lipids promotes transgene delivery to the nucleus in mammalian cells. *J. Biol. Chem.* 273: 7507-11 (1998).
Presta et al., Engineering therapeutic antibodies for improved function. *Biochem. Soc. Trans.* 30: 487-90 (2002).
Rajpal et al., A general method for greatly improving the affinity of antibodies by using combinatorial libraries. *Proc. Natl. Acad. Sci. USA.* 102: 8466-71 (2005).
Reyes et al., Expression of human beta-interferon cDNA under the control of a thymidine kinase promoter from herpes simplex virus. *Nature* 297: 598-601 (1982).
Riechman et al., Single domain antibodies: comparison of camel VH and camelised human VH domains. *J. Immunol. Methods.* 231: 25-38 (1999).
Riechmann et al., Reshaping human antibodies for therapy. *Nature.* 332: 323-7 (1988).
Rose et al., A new cationic liposome reagent mediating nearly quantitative transfection of animal cells. *Biotechnique* 10: 520-5 (1991).
Roth et al., VDJ recombination: a transposase goes to work. *Cell.* 94: 411-4 (1998).
Sarmay et al., Mapping and comparison of the interaction sites on the Fc region of IgG responsible for triggering antibody dependent cellular cytotoxicity (ADCC) through different types of human Fc gamma receptor. *Molec. Immunol.* 29: 633-9 (1992).
Schmidt et al., A bivalent single-chain antibody-toxin specific for ErbB-2 and the EGF receptor. *Int. J. Cancer.* 65: 538 (1996).
Schoonjans et al., Fab chains as an efficient heterodimerization scaffold for the production of recombinant bispecific and trispecific antibody derivatives. *J. Immunol.* 165: 7050-7 (2000).
Schuurman et al., The inter-heavy chain disulfide bonds of IgG4 are in equilibrium with intra-chain disulfide bonds. *Mol. Immunol.* 38: 1-8 (2001).
Shalaby et al., Development of humanized bispecific antibodies reactive with cytotoxic lymphocytes and tumor cells overexpressing the HER2 protooncogene. *J. Exp. Med.* 175: 217-25 (1992).
Shields et al., High resolution mapping of the binding site on human IgG1 for Fc gamma RI, Fc gamma RII, Fc gamma RIII, and FcRn and design of IgG1 variants with improved binding to the Fc gamma R. *J. Biol. Chem.* 276: 6591-04 (2001).
Shields et al., Lack of fucose on human IgG1 N-linked oligosaccharide improves binding to human Fcgamma RIII and antibody-dependent cellular toxicity. *J. Biol. Chem.* 277: 26733-40 (2002).
Shih et al., A fluorouridine-anti-CEA immunoconjugate is therapeutically effective in a human colonic cancer xenograft model. *Int. J. Cancer.* 46: 1101-6 (1990).
Shih et al., Site-specific linkage of methotrexate to monoclonal antibodies using an intermediate carrier. *Int. J. Cancer.* 41: 832-9 (1988).
Shinkawa et al., The absence of fucose but not the presence of galactose or bisecting N-acetylglucosamine of human IgG1 complex-type oligosaccharides shows the critical role of enhancing antibody-dependent cellular cytotoxicity. *J. Biol. Chem.* 278: 3466-73 (2003).
Shopes et al., A genetically engineered human IgG mutant with enhanced cytolytic activity. *J. Immunol.* 148: 2918-22 (1992).
Skerra et al., Assembly of a functional immunoglobulin Fv fragment in *Escherichia coli. Science* 240: 1038-41 (1988).
Sojar et al., A chemical method for the deglycosylation of proteins. *Arch. Biochem. Biophys.* 259: 52-7 (1987).
Stein et al., Eph receptors discriminate specific ligand oligomers to determine alternative signaling complexes, attachment, and assembly responses. *Genes. Dev.* 12: 667-78 (1998).
Stemmer, DNA shuffling by random fragmentation and reassembly: in vitro recombination for molecular evolution. *Proc. Natl. Acad. Sci. USA.* 91: 10747-51 (1994).
Steplewski et al., Biological activity of human-mouse IgG1, IgG2, IgG3, and IgG4 chimeric monoclonal antibodies with antitumor specificity. *Proc. Natl. Acad. Sci. USA.* 85: 4852-6 (1988).
Sternberger et al., The unlabeled antibody enzyme method of immunohistochemistry: preparation and properties of soluble antigen-antibody complex (horseradish peroxidase-antihorseradish peroxidase) and its use in identification of spirochetes. *J. Histchem. Cytochem.* 18: 315-33 (1970).
Stevenson et al., A chimeric antibody with dual Fc regions (bisFabFc) prepared by manipulations at the IgG hinge. *Anticancer Drug Des.* 3: 219-30 (1989).
Stinchcomb et al., Isolation and characterisation of a yeast chromosomal replicator. *Nature.* 282: 39-43 (1979).
Studnicka et al., Human-engineered monoclonal antibodies retain full specific binding activity by preserving non-CDR complementarity-modulating residues. *Protein Eng.* 7: 805-14 (1994).
Tang et al., High-level expression of EPHB6, EFNB2, and EFNB3 is associated with low tumor stage and high TrkA expression in human neuroblastomas. *Clin. Cancer. Res.* 5: 1491-6 (1999).
Thompson et al., An anti-CD3 single-chain immunotoxin with a truncated diphtheria toxin avoids inhibition by pre-existing antibodies in human blood. *J. Biol. Chem.* 270: 28037-41 (1995).
Thotakura et al., Enzymatic deglycosylation of glycoproteins. *Methods Enzymol.* 138: 350-9 (1987).
Tutt et al., Trispecific F(ab')3 derivatives that use cooperative signaling via the TCR/CD3 complex and CD2 to activate and redirect resting cytotoxic T cells. *J. Immunol.* 147: 60-9 (1991).
Umana et al., Engineered glycoforms of an antineuroblastoma IgG1 with optimized antibody-dependent cellular cytotoxic activity. *Nat. Biotechnol.* 17: 176-80 (1999).
Urlaub et al., Isolation of Chinese hamster cell mutants deficient in dihydrofolate reductase activity. *Proc. Natl. Acad. Sci. USA.* 77: 4216-20 (1980).
Vallera et al., Anti-graft-versus-host disease effect of DT390-anti-CD3sFv, a single-chain Fv fusion immunotoxin specifically targeting the CD3 epsilon moiety of the T-cell receptor. *Blood.* 88: 2342-53 (1996).
Van den Berg, Kluyveromyces as a host for heterologous gene expression: expression and secretion of prochymosin. *Bio/Technology.* 8: 135-9 (1991).
Van Heumen et al., Expression of EphA4 in developing inner ear of the mouse and guinea pig. *Hear. Res..* 139: 42-50 (2000).
Verhoeyen et al., Reshaping human antibodies: grafting an antilysozyme activity. *Science.* 239: 1534-6 (1988).
Verma, Gene therapy. *Sci Am.* 68-84 (1990).
Vitetta et al., Redesigning nature's poisons to create anti-tumor reagents. *Science* 238: 1098-104 (1987).
Wang et al., Molecular distinction and angiogenic interaction between embryonic arteries and veins revealed by ephrin-B2 and its receptor Eph-B4. *Cell.* 93: 741-53 (1998).
Ward et al., Binding activities of a repertoire of single immunoglobulin variable domains secreted from *Escherichia coli. Nature.* 341 544-6 (1989).
Wels et al., EGF receptor and p185erbB-2-specific single-chain antibody toxins differ in their cell-killing activity on tumor cells expressing both receptor proteins. *Int. J. Cancer.* 60: 137-44 (1995).
Wheeler et al., Intrabody-based strategies for inhibition of vascular endothelial growth factor receptor-2: effects on apoptosis, cell growth, and angiogenesis. *FASEB J.* 17: 1733-5 (2003).
Willems et al., Optimizing expression and purification from cell culture medium of trispecific recombinant antibody derivatives. *J. Chromatogr. B. Analyt Technol. Biomed. Life Sci.* 786: 161-76 (2003).
Wilman, Prodrugs in Cancer Chemotherapy, *Biochem. Soc. Trans.* 14: 375-82 (1986).
Winter et al., Making antibodies by phage display technology. *Annu. Rev. Immunol.* 12: 433-55 (1994).
Wolff et al., Monoclonal antibody homodimers: enhanced antitumor activity in nude mice. *Cancer Res.* 53: 2560-5 (1993).
Xu et al., Residue at position 331 in the IgG1 and IgG4 CH2 domains contributes to their differential ability to bind and activate complement. *J. Biol. Chem.* 269: 3469-74 (1994).
Yamane-Ohnuki et al., Establishment of FUT8 knockout Chinese hamster ovary cells: an ideal host cell line for producing completely defucosylated antibodies with enhanced antibody-dependent cellular cytotoxicity. *Biotechnol. Bioeng.* 87: 614-22 (2004).

(56) References Cited

OTHER PUBLICATIONS

Yaniv et al., Enhancing elements for activation of eukaryotic promoters. *Nature*. 297: 17-8 (1982).

Yu et al., Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells. *Int. J. Cancer*. 56: 244-8 (1994).

Zaccolo et al., The effect of high-frequency random mutagenesis on in vitro protein evolution: a study on TEM-1 beta-lactamase. *J. Mol. Biol*. 285: 775-83 (1999).

Zapata et al., Engineering linear F(ab')2 fragments for efficient production in *Escherichia coli* and enhanced antiproliferative activity. *Protein Eng*. 8: 1057-62 (1995).

Zhou et al., Lipophilic polylsines mediate effienct DNA transfection in mammalian cells: *Biochim. Biophys. Acta*. 1065: 8-14 (1991).

Zou et al., An Eph receptor regulates integrin activity through R-Ras. *Proc. Natl. Acad. Sci. USA*. 96: 13813-8 (1999).

International Search Report, European Patent Office, PCT/US2007/075215, dated Mar. 13, 2008.

Written Opinion of the International Searching Authority, European Patent Office, PCT/US2007/075215, dated Mar. 13, 2008.

* cited by examiner

FIGURE 7

EPHB3-SPECIFIC ANTIBODY AND USES THEREOF

CROSS REFERENCE TO RELATED APPLICATIONS

This application claims priority to U.S. Provisional Patent Application Ser. No. 60/835,777, filed Aug. 4, 2006.

TECHNICAL FIELD

This invention relates to methods for preventing and treating cancer by administering EphB3-specific antibodies.

BACKGROUND OF THE INVENTION

Cancer is the second leading cause of death in the United States. Although "cancer" is used to describe many different types of cancer, i.e. breast, prostate, lung, colon, pancreas, each type of cancer differs both at the phenotypic level and the genetic level. The unregulated growth characteristic of cancer occurs when the expression of one or more genes becomes dysregulated due to mutations or epigenetic changes, and cell growth can no longer be controlled.

Growth control genes are often classified in two classes, oncogenes and tumor suppressor genes. Oncogenes are genes whose normal function is to promote cell growth, but only under specific conditions. When an oncogene gains a mutation and loses that specificity control, it promotes growth under a much wider variety of conditions. However, it has been found that for cancer to be truly successful the cancer cell must also acquire mutations in tumor suppressor genes. The normal function of tumor suppressor genes is to stop cellular growth. Examples of tumor suppressors include p53, p16, p21, and APC, all of which, when acting normally, stop a cell from dividing and growing uncontrollably. When a tumor suppressor is mutated or lost, that brake on cellular growth is also lost, allowing cells to now grow without the normal restraints.

EphB3 is a receptor in the ephrin receptor tyrosine kinase family. Presently there are 14 Eph receptors and 9 ephrin ligands known in humans. Ephrin receptors (Ephs) and their ligands, the ephrins, mediate numerous developmental processes, particularly in the nervous system and vascular systems. Ephrins are also known to play a role in tumor development, angiogenesis, metastatic growth and cell survival. Based on their structures and sequence relationships, ephrins are divided into the ephrin-A (EFNA) class, which are anchored to the membrane by a glycosylphosphatidylinositol linkage, and the ephrin-B (EFNB) class, which are transmembrane proteins. The Eph family of receptors is divided into 2 groups based on the similarity of their extracellular domain sequences and their affinities for binding ephrin-A and ephrin-B ligands. Eph receptors make up the largest subgroup of the receptor tyrosine kinase (RTK) family.

Eph receptors have been implicated in cancer. NIH3T3 cells transfected with EphA1 and transplanted into nude mice produce 10 mm$^3$ tumors in 5-6 weeks, while vector controls did not produce any tumors during the same time period (Maru et al., Oncogene. 1990 March; 5(3):445-7). EphB2 is expressed at higher levels in cancers of the stomach (12/16), colon (3/11), esophagus (3/6), ovarian (1/7), kidney (1/2) and lung (1/1) when compared to normal tissues (Kiyokawa et al., Cancer Res 1994 Jul. 15; 54(14):3645-50). EphB6 expression correlates with low grade neuroblastomas. The kinase domain of EphB6 is not active, therefore this receptor has been proposed to act as a naturally occurring dominant negative (Tang et al., Clin Cancer Res 1999a June; 5(6):1491-6).

There is an increasing volume of evidence that implicates the involvement of Ephs and ephrins in angiogenesis. EphrinA1, ephrinB1, ephrinB2, EphB2, EphB3 and EphB4 have been reported to be expressed in blood vessels. EphrinA1 can induce angiogenesis in the rat cornea model and antibodies to ephrinA1 can inhibit TNF-α induced angiogenesis in this same model (Pandey et al., Science 1995 Apr. 28; 268(5210): 567-9). Clustered ephrinB1 induces cell attachment and capillary-like assembly in P19, a teratocarcinoma-derived murine cell line, and in human renal microvascular endothelial cells (HRMEC) (Stein et al., Genes Dev 1998 Mar. 1; 12(5):667-78). Clustered ephrinB1 and ephrinB2 can also induce sprouting of adrenal-cortex derived microvascular endothelial cells (ACE) (Adams et al., Genes Dev 1999 Feb. 1; 13(3):295-306). Injection of a dominant negative EphB4 receptor RNA in *Xenopus* embryos causes intersomitic veins to project abnormally into adjacent somites (Helbling et al., Development 2000 January; 127(2):269-78). EphB2/EphB3 double knockout, EphB4 and ephrinB2 knockout mice all have vascular remodeling defects (Adams et al., 1999; Wang et al., Cell 1998 May 29; 93(5):741-53; PCT WO 00/30673).

Ephs may also play a role in metastasis. 293T human epithelial kidney cells transfected with either EphB3 or EphB2 exhibit reduced cell adhesion to fibronectin or collagen coated surfaces in vitro. Failure of 293 cells to adhere was mediated by EphB2 phosphorylation of R-ras followed by integrin de-activation (Zou et al., Proc Natl Acad Sci USA 1999 Nov. 23; 96(24):13813-8).

Ephs appear to function by signaling upon activation. Ephrin binding induces Eph receptor oligomerization causing phosphorylation of juxtamembrane residues of Ephs. Activated Ephs have multiple phosphorylated tyrosines that act as docking sites for signaling proteins (e.g. RasGAP, Src, LMW-PTP, PLCg, PI3-kinase, Grb2, and PDZ containing proteins). Overexpression of Eph receptors (EphA1, EphA2, EphB2) causes transformation in the absence of receptor hyper-phosphorylation. Phosphorylated EphB receptors negatively regulate the Ras-MAP-kinase pathway and FAK signaling, impairing cell growth.

EphB3 (also known as Hek2, Sek4, Mdk5, Tyro6, Cek10 and Qek10) is a receptor for ephrin B family members (ephrin B1, ephrin B2 and ephrin B3), and is known to be expressed in normal tissue and in certain tumors and cancer cell lines. To date, however, the role of EphB3 in cancer has not been elucidated. Thus, there is a need to identify compositions and methods that modulate EphB3 and its role in such cancers. The present invention is directed to these, as well as other, important needs.

SUMMARY OF THE INVENTION

The nucleotide sequence for EphB3 is set out in SEQ ID NO: 1, and the amino acid sequence is set out in SEQ ID NO: 2. The extracellular domain (ECD) consists of amino acids 1 through 559 of SEQ ID NO: 2. Alternatively, the ECD consists of 34 through 555 of SEQ ID NO: 2 (Note that there are two locus numbers corresponding to human EphB3 in the NCBI Entrez database of protein sequences. In both cases, predictions were made by the researchers submitting the sequences as to (a) the number of amino acids encoded by the coding region from the ATG start codon to the termination codon; (b) what stretch of amino acids in that precursor sequence represents the secretion signal sequence (this sequence would be clipped off during the maturation process to create the mature protein); and (c) what stretch of residues represents the transmembrane region. Since the "extracellular" domain of the mature protein is whatever lies between the signal sequence and the transmembrane domain, the predicted extent of the ECD depends on where you place the signal and TM regions. Both locus submissions (NP_004434 and P54753) predict that the precursor is 998 amino acids in length, and that the secretion signal spans residues 1-33. Thus, they both agree that the start of the ECD is residue 34. However, they disagree on the start of the TM region: NP_004434 predicts the start is residue 556 (making the end of the ECD amino acid number 555), while P54753 predicts the TM starts at residue 560 (making the ECD end at amino acid number 559)). As described in the examples herein, an ECD consisting of amino acids 37-558 was used for immunizations for antibody generation.

The materials and methods of the present invention fulfill the aforementioned and other related needs in the art.

In one embodiment of the invention, an antibody that binds the extracellular domain of EphB3 with an affinity (KD) of $10^{-6}$ M or less and competes with any of antibodies XPA.04.001, XPA.04.013, XPA.04.018, XPA.04.048, XHA.05.337, XHA.05.200, XHA.05.111, XHA.05.005, XHA.05.228, XHA.05.030, XHA.05.964, or XHA.05.885 for binding to EphB3 by more than 75% is provided. By the term "affinity (KD) of 10-6 M or less" it is meant an affinity of, e.g., $10^{-6}$ M, $10^{-7}$ M, $10^{-8}$ M, $10^{-9}$ M, $10^{-10}$ M, $10^{-11}$ M or $10^{-12}$ M (i.e., a number lower than $10^{-6}$ M). In another embodiment, the antibody binds to the same epitope of EphB3 as any of antibodies XPA.04.001, XPA.04.013, XPA.04.018, XPA.04.048, XHA.05.337, XHA.05.200, XHA.05.111, XHA.05.005, XHA.05.228, XHA.05.030, XHA.05.964, or XHA.05.885. In still another embodiment, an antibody is provided that comprises 1, 2, 3, 4, 5 or 6 CDRs of any of antibodies XPA.04.001, XPA.04.013, XPA.04.018, XPA.04.048, XHA.05.337, XHA.05.200, XHA.05.111, XHA.05.005, XHA.05.228, XHA.05.030, XHA.05.964, or XHA.05.885. In yet another embodiment, an aforementioned antibody is a chimeric antibody, a humanized antibody, a human engineered antibody, a human antibody, a single chain antibody or an antibody fragment.

In another embodiment of the invention, an aforementioned antibody is provided in which at least one amino acid within a CDR is substituted by a corresponding residue of a corresponding CDR of another anti-EphB3 antibody. In an exemplary embodiment, an aforementioned antibody is provided in which at least one amino acid within a CDR from an antibody selected from the group consisting of XPA.04.001, XPA.04.013, XPA.04.018, XPA.04.048, XHA.05.337, XHA.05.200, XHA.05.111, XHA.05.005, XHA.05.228, XHA.05.030, XHA.05.964, and XHA.05.885 is substituted by a corresponding residue of a corresponding CDR of another anti-EphB3 antibody. In another exemplary embodiment, an aforementioned antibody is provided in which at least one amino acid within a CDR from an antibody selected from the group consisting of XPA.04.001, XPA.04.013, XPA.04.018, XPA.04.048, XHA.05.337, XHA.05.200, XHA.05.111, XHA.05.005, XHA.05.228, XHA.05.030, XHA.05.964, and XHA.05.885 is substituted by a corresponding residue of a corresponding CDR of another antibody selected from the group consisting of XPA.04.001, XPA.04.013, XPA.04.018, XPA.04.048, XHA.05.337, XHA.05.200, XHA.05.111, XHA.05.005, XHA.05.228, XHA.05.030, XHA.05.964, and XHA.05.885. In another embodiment, an aforementioned antibody is provided in which one or two amino acids within a CDR have been modified. In still another embodiment, the antibody retains at least 60, 65, 70, 75, 80, 85, 90, 91, 92, 93, 94, 95, 96, 97, 98, or 99% identity over either the variable light or heavy region to the antibodies of XPA.04.001, XPA.04.013, XPA.04.018, XPA.04.048, XHA.05.337, XHA.05.200, XHA.05.111, XHA.05.005, XHA.05.228, XHA.05.030, XHA.05.964, or XHA.05.885. In yet another embodiment, the aforementioned antibody comprises a constant region of a human antibody sequence and one or more heavy and light chain variable framework regions of a human antibody sequence. In still another embodiment, the aforementioned antibody is provided wherein the human antibody sequence is an individual human sequence, a human consensus sequence, an individual human germline sequence, or a human consensus germline sequence.

In still another embodiment, the invention provides an aforementioned antibody wherein the heavy chain constant region is a modified or unmodified IgG, IgM, IgA, IgD, IgE, a fragment thereof, or combinations thereof. In another embodiment, the antibody has a binding affinity of $10^{-7}$, $10^{-8}$, $10^{-9}$, $10^{-10}$ or $10^{-11}$ M or less to EphB3. In yet another embodiment, an aforementioned antibody is provided comprising a conservative substitution in the CDRs. In yet another embodiment, an aforementioned antibody is provided comprising conservative or non-conservative change in low and moderate risk residues. In another embodiment, an aforementioned antibody is provided wherein the light chain constant region is a modified or unmodified lambda light chain constant region, a kappa light chain constant region, a fragment thereof, or combinations thereof.

In another embodiment of the invention, an aforementioned antibody is provided that induces EphB3 phosphorylation, induces EphB3 oligomerization, induces EphB3 internalization, induces EphB3 degradation, induces EphB3 signaling, inhibits the binding of an ephrinB to EphB3, and/or inhibits the proliferation of a cancer cell. In yet another embodiment, an aforementioned antibody is provided that inhibits proliferation of a lung, ovarian, esophageal, colon or breast cancer cell. In still another embodiment, an aforementioned antibody is provided that is conjugated to another diagnostic or therapeutic agent.

Numerous methods are contemplated by the present invention. In one embodiment of the invention, a method of screening for an antibody to the extracellular domain of a EphB3 protein useful for the treatment of cancer is provided comprising the steps of: contacting a polypeptide comprising the ECD of EphB3 with a candidate antibody that contains at least 1, 2, 3, 4, 5 or 6 CDRs of antibodies XPA.04.001, XPA.04.013, XPA.04.018, XPA.04.048, XHA.05.337, XHA.05.200, XHA.05.111, XHA.05.005, XHA.05.228, XHA.05.030, XHA.05.964, or XHA.05.885; detecting binding affinity of the candidate antibody to the polypeptide, and identifying the candidate antibody as an antibody useful for the treatment of cancer if a binding affinity of at least $10^{-6}$ M is detected. In yet another embodiment, a method of systematically altering antibodies and screening for an antibody to the extracellular domain of a EphB3 protein useful for the treatment of cancer is provided comprising the steps of: preparing a candidate antibody that contains modifications to one or two amino acids within the CDRs of antibodies XPA.04.001, XPA.04.013, XPA.04.018, XPA.04.048, XHA.05.337, XHA.05.200, XHA.05.111, XHA.05.005, XHA.05.228, XHA.05.030, XHA.05.964, or XHA.05.885; contacting a polypeptide comprising the ECD of EphB3 with the candidate antibody; detecting binding affinity of the candidate antibody to the polypeptide, and identifying the candidate antibody as an antibody useful for the treatment of cancer if a binding affinity of at least 10-6 M is detected.

In yet another embodiment, a method of screening for an antibody to the extracellular domain of a EphB3 protein useful for the treatment of cancer is provided comprising the steps of: contacting a lung, ovarian, esophageal, colon or breast cell with a candidate antibody that contains at least 1, 2, 3, 4, 5 or 6 CDRs of antibodies XPA.04.001, XPA.04.013, XPA.04.018, XPA.04.048, XHA.05.337, XHA.05.200, XHA.05.111, XHA.05.005, XHA.05.228, XHA.05.030, XHA.05.964, or XHA.05.885 or an antibody that contains a modification of one or two amino acids within one or more CDRs; detecting proliferation or survival of the cell; and identifying the candidate antibody as an antibody useful for the treatment of cancer if a decrease in cell proliferation or survival is detected.

In yet another embodiment, a method of treating a subject suffering from cancer is provided comprising the step of administering an aforementioned antibody in a therapeutically effective amount. In a related embodiment, the cancer is lung, ovarian, esophageal, colon or breast cancer. In still another embodiment, a second therapeutic agent is administered. In yet another embodiment, the subject is further treated with radiation therapy or surgery. In a further embodiment, the invention provides an antibody of the invention for use in medicine, including for use in treating a cancer e.g. by the aforementioned methods. In other embodiments, the invention provides the use of an antibody of the invention in the manufacture of a medicament for treating a cancer. The medicament may be administered to a patient in combination with a second therapeutic agent, and/or with radiation therapy.

In still another embodiment of the invention, a method of targeting a tumor cell expressing EphB3 is provided comprising the step of administering an aforementioned antibody, conjugated to a radionuclide or other toxin. In still another embodiment, an aforementioned method is provided wherein the subject is a mammal. In still another embodiment, the subject is a human.

In another embodiment of the invention, an isolated nucleic acid molecule is provided comprising a nucleotide sequence that encodes the heavy chain or light chain of an aforementioned antibody. In still another embodiment, an expression vector is provided comprising the aforementioned nucleic acid molecule operably linked to a regulatory control sequence. In yet another embodiment, a host cell is provided comprising the aforementioned vector or the aforementioned nucleic acid molecule. In still another embodiment, a method of using the aforementioned host cell to produce an antibody is provided, comprising culturing the host cell under suitable conditions and recovering the antibody. In another embodiment, the antibody produced by the aforementioned method is provided.

In another embodiment of the invention, an aforementioned antibody is provided that is purified to at least 95% homogeneity by weight. In still another embodiment, a pharmaceutical composition comprising the aforementionmed antibody and a pharmaceutically acceptable carrier is provided. In yet another embodiment, a kit is provided comprising an aforementioned antibody comprising a therapeutically effective amount of an antibody of the invention, packaged in a container, wherein the kit optionally contains a second therapeutic agent, and further comprising a label attached to or packaged with the container, the label describing the contents of the container and providing indications and/or instructions regarding use of the contents of the container to treat cancer. In another embodiment, the aforementioned kit is provided wherein the container is a vial or bottle or prefilled syringe.

BRIEF DESCRIPTION OF THE DRAWINGS

Figure 7:
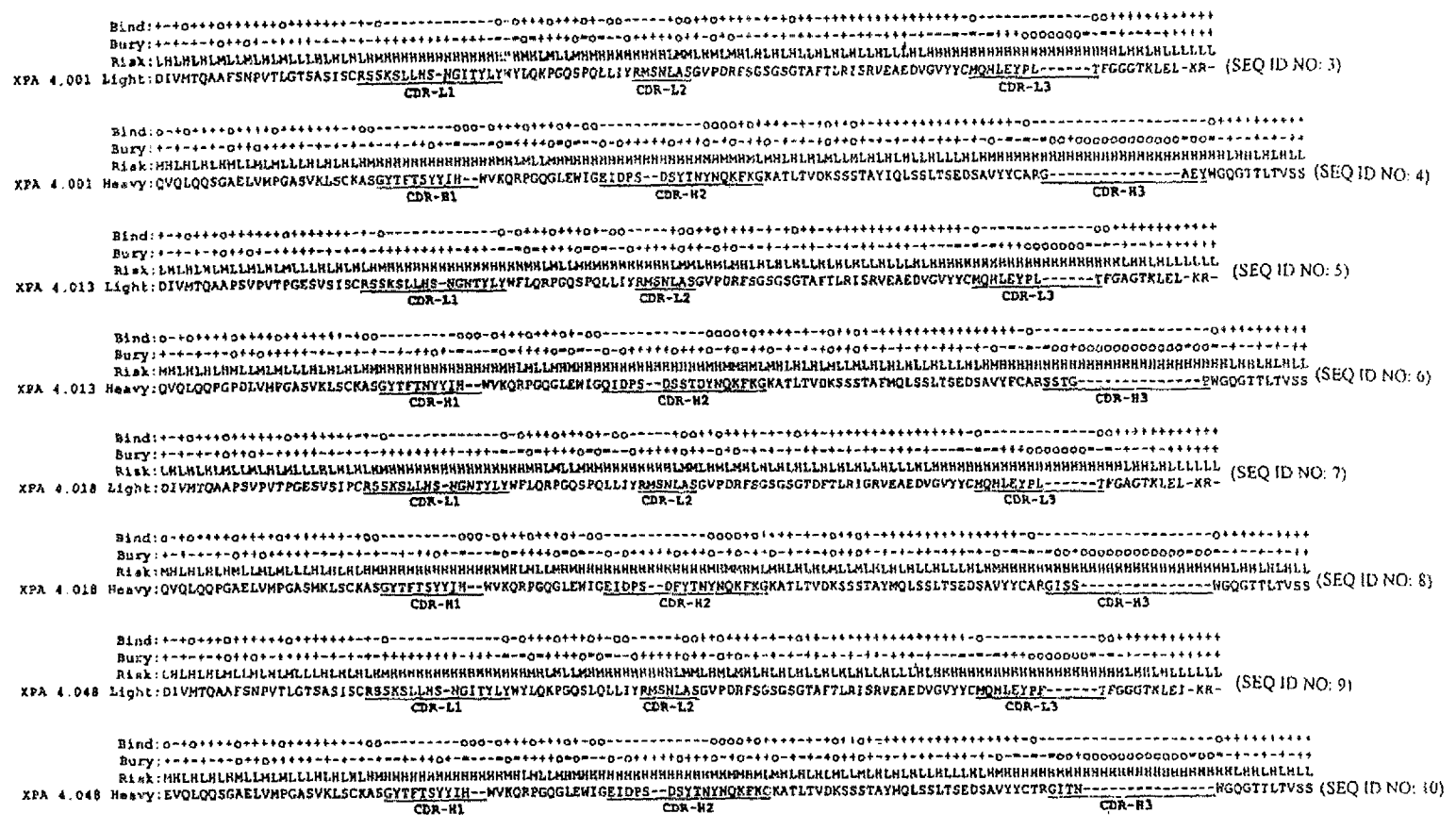

FIG. 7 shows the risk line for the XPA.04.001, XPA.04.013, XPA.04.018, XPA.04.048 light chain and heavy chain (H=high risk, M=moderate risk, L=low risk), the XPA.04.001, XPA.04.013, XPA.04.018, XPA.04.048 light chain and heavy chain variable region amino acid sequence (SEQ ID NOs: 3-10), and the location of CDR H1, H2 and H3 within the amino acid sequence.

DETAILED DESCRIPTION

Figure 1:
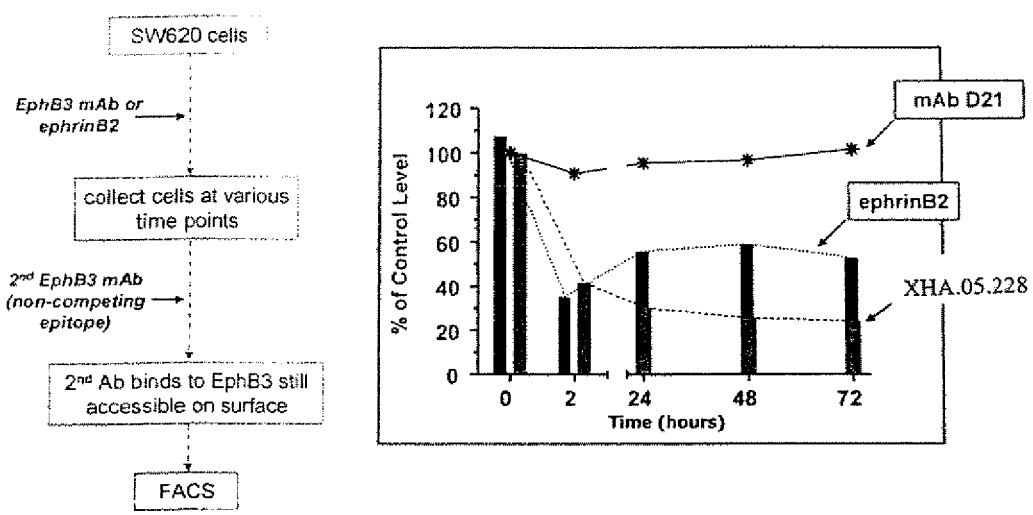
FIG. 1 shows the results of a FACS analysis demonstrating mAb-induced EphB3 internalization/degradation.

The present invention provides EphB3-specific antibodies, pharmaceutical formulations containing such antibodies, methods of preparing the antibodies and pharmaceutical formulations, and methods of treating patients with the pharmaceutical formulations and compounds. Antibodies according to the present invention may have a desired biological activity of binding to EphB3, inducing EphB3 phosphorylation, inducing EphB3 oligomerization, inducing EphB3 internalization, inducing EphB3 degradation, inducing EphB3 signaling, and/or modulating EphB3-mediated cell-cell adhesion.

In one embodiments, antibodies of the present invention act as agonists of the polypeptides of the present invention. Accordingly, in some embodiments, antibodies of the present invention may activate or induce a function of a target antigen to which it binds (e.g., increasing a function of the target, such as phosphorylation activity or intracellular signaling).

In some embodiments antibodies of the present invention bind an epitope disclosed herein, or a portion thereof. In some embodiments, binding of the antibody to the receptor induces receptor degradation. In some embodiments, binding of the antibody to the receptor induces receptor oligomerization. In some embodiments, binding of the antibody to the receptor induces receptor phosphorylation. In some embodiments, binding of the antibody to the receptor induces receptor activation. Receptor activation (i.e., signaling) may be determined by techniques known in the art. For example, receptor activation can be determined by detecting the phosphorylation (e.g., tyrosine or serine/threonine) of the receptor or its substrate by immunoprecipitation followed by Western blot analysis. In some embodiments, antibodies are provided that modulate ligand activity or receptor activity as described herein by at least 95%, at least 90%, at least 85%, at least 80%, at least 75%, at least 70%, at least 60%, or at least 50% of the activity in absence of the antibody.

In some embodiments the EphB3 antibodies stimulate EphB3 binding to intracellular adaptor proteins. In some embodiments, EphB3 antibodies inhibit and/or inactivate FAK, the Erk/MAPK pathway, the Cdc42/Rac pathway, activates RasGAP, inhibits and/or inactivates Abl/Arg, Fyn, Src, LMW-PTP, Intersectin, the Cdc42 pathway, Kalirin or the Rac pathway. In some embodiments, the EphB3 antibodies inactivate R-ras or activate Syndecan. In some embodiments, the EphB3 antibodies lead to the phosphorylation of R-Ras.

As used herein, the term "intracellular adaptor proteins" refers to a protein that connects different segments of a signaling complex. The adaptor may or may not have enzymatic activity. Examples of adaptor proteins are known to those of skill in the art. For example, Grb2 is an adaptor protein that does not have intrinsic enzymatic activity, while RasGAP is an adaptor protein that has enzymatic activity.

Antibodies according to the present invention may alternatively (or in addition) have a desired biological activity of binding to EphB3 expressed on cancer cells, thus serving to target cytotoxic therapies to the cancer cells.

Several preferred murine or chimeric antibodies with high affinity and potency as measured by in vitro assays are modified to be less immunogenic in humans based on the Human Engineering™ method of Studnicka et al. Briefly, surface exposed amino acid residues of the heavy chain and light chain variable regions are modified to human residues in positions determined to be unlikely to adversely effect either antigen binding or protein folding, while reducing its immunogenicity with respect to a human environment. Synthetic genes encoding modified heavy and/or light chain variable regions are constructed and linked to coding sequences for the human gamma heavy chain and/or kappa light chain constant regions. Any human heavy chain and light chain constant regions may be used in combination with the Human Engineered™ antibody variable regions. The human heavy and light chain genes are introduced into mammalian cells and the resultant recombinant immunoglobulin products are obtained and characterized.

Exemplary antibodies according to the invention include XPA.04.001, XPA.04.013, XPA.04.018, XPA.04.048, XHA.05.337, XHA.05.200, XHA.05.111, XHA.05.005, XHA.05.228, XHA.05.030, XHA.05.964, and XHA.05.885. The following antibody-secreting hybridomas were deposited with the American Type Culture Collection (ATCC), 10801 University Blvd., Manassas, Va. 20110-2209 (USA), pursuant to the provisions of the Budapest Treaty, on Aug. 4, 2006:

| HYBRIDOMA NAME | ATCC DEPOSIT NUMBER |
|---|---|
| XHA.05.337 | PTA-7779 |
| XHA.05.200 | PTA-7786 |
| XHA.05.111 | PTA-7785 |
| XHA.05.005 | PTA-7782 |
| XHA.05.228 | PTA-7781 |
| XHA.05.030 | PTA-7780 |
| XHA.05.964 | PTA-7784 |
| XHA.05.885 | PTA-7783 |

The definitions below are provided as an aid to understanding the invention more completely.

General Definitions

The target antigen human "EphB3" as used herein refers to a human polypeptide having substantially the same amino acid sequence as SEQ ID NO: 2 and naturally occurring allelic variants thereof. "ECD of EphB3" as used herein refers to the extracellular portion of EphB3 represented by amino acids 37-558 of SEQ ID NO: 2 (see also discussion above with respect to the published classification of the ECD).

"Tumor" as used herein refers to all neoplastic cell growth and proliferation, whether malignant or benign, and all pre-cancerous and cancerous cells and tissues.

The terms "cancer" and "cancerous" refer to or describe the physiological condition in mammals that is typically characterized by dysregulated cell growth. Examples of cancer include but are not limited to squamous and small cell lung carcinomas, esophageal squamous cell carcinoma, ovarian clear cell carcinoma, colon adenocarcinomas, and infiltrating ductal breast carcinoma.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. Treatment of patients suffering from clinical, biochemical, radiological or subjective symptoms of the disease may include alleviating some or all of such symptoms or reducing the predisposition to the disease. The "pathology" of cancer includes all phenomena that compromise the well being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, etc. Thus, improvement after treatment may be manifested as decreased tumor size, decline in tumor growth rate, destruction of existing tumor cells or metastatic cells, and/or a reduction in the size or number of metastases.

"Mammal" for purposes of treatment refers to any animal classified as a mammal, including humans, domestic and farm animals, and zoo, sports, or pet animals, such as dogs, horses, cats, cows, etc. Preferably, the mammal is human.

As used herein, the phrase "therapeutically effective amount" is meant to refer to an amount of therapeutic or prophylactic antibody that would be appropriate for an embodiment of the present invention, that will elicit the desired therapeutic or prophylactic effect or response, including alleviating some or all of such symptoms of disease or reducing the predisposition to the disease, when administered in accordance with the desired treatment regimen.

Antibodies

The term "immunospecific" or "specifically binding" means that the antibody binds to EphB3 or its ECD with a $K_a$ of greater than or equal to about $10^4$ $M^{-1}$, preferably greater than or equal to about $10^5$ $M^{-1}$, more preferably greater than or equal to about $10^6$ $M^{-1}$. The antibody may have substantially greater affinity for the target antigen compared to other unrelated molecules. The antibody may also have substantially greater affinity for the target antigen compared to orthologs or homologs, e.g. at least 1.5-fold, 2-fold, 5-fold 10-fold, 100-fold, $10^3$-fold, $10^4$-fold, $10^5$-fold, $10^6$-fold or greater relative affinity for the target antigen. Alternatively, it might be useful for the antibody to cross react with a known homolog or ortholog.

Antibodies of the invention may also be characterized by an affinity ($K_D$) of at least $10^{-4}$ M, preferably at least about $10^{-4}$ M to about $10^{-12}$ M, more preferably at least about $10^{-5}$ M, $10^{-6}$ M, $10^{-7}$ M or $10^{-8}$ M, $10^{-9}$ M, $10^{-10}$ M, or $10^{-11}$ M. The appropriate affinity for the antibodies may vary depending on the therapeutic application. For example, while antibodies with very high affinity may be most desirable as a blood cancer therapeutic, an antibody with very high affinity may display poor penetration of solid tumors. Accordingly, an antibody with an affinity of about $10^{-6}$ M to $10^{-10}$ M may be more appropriate as a solid tumor therapeutic. Such affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. Sci., 51:660 (1949).

By "agonist antibody" is meant an antibody molecule that is able to activate or induce a function of a target antigen to which it binds. Accordingly, an "agonist" anti-target antibody is capable of increasing a function of the target, such as phosphorylation activity or intracellular signaling.

The term "antibody" is used in the broadest sense and includes fully assembled antibodies, monoclonal antibodies, polyclonal antibodies, multispecific antibodies (e.g., bispecific antibodies), antibody fragments that can bind antigen (e.g., Fab', F'(ab)2, Fv, single chain antibodies, diabodies), and recombinant peptides comprising the forgoing as long as they exhibit the desired biological activity. Antibody fragments may be produced by recombinant DNA techniques or by enzymatic or chemical cleavage of intact antibodies and are described further below. Nonlimiting examples of monoclonal antibodies include murine, chimeric, humanized, human, and Human Engineered™ immunoglobulins, antibodies, chimeric fusion proteins having sequences derived from immunoglobulins, or muteins or derivatives thereof, each described further below. Multimers or aggregates of intact molecules and/or fragments, including chemically derivatized antibodies, are contemplated. Antibodies of any isotype class or subclass are contemplated according to the present invention.

The term "monoclonal antibody" as used herein refers to an antibody obtained from a population of substantially homogeneous antibodies, i.e., the individual antibodies comprising the population are identical except for possible naturally occurring mutations or alternative post-translational modifications that may be present in minor amounts. Monoclonal antibodies are highly specific; in contrast to conventional (polyclonal) antibody preparations that typically include different antibodies directed against different determinants (epitopes), each monoclonal antibody is directed against a single determinant on the antigen. In addition to their specificity, the monoclonal antibodies are advantageous in that they are synthesized by the homogeneous culture, uncontaminated by other immunoglobulins with different specificities and characteristics.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., 1975 Nature, 256:495, or may be made by recombinant DNA methods (see, e.g., U.S. Pat. No. 4,816,567). The "monoclonal antibodies" may also be recombinant, chimeric, humanized, human, Human Engineered™, or antibody fragments, for example.

An "isolated" antibody is one that has been identified and separated and recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "immunoglobulin" or "native antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a "variable" ("V") region of about 100 to 110 or more amino acids primarily responsible for antigen recognition. The carboxy-terminal portion of each chain defines a constant region primarily responsible for effector function. Immunoglobulins can be assigned to different classes depending on the amino acid sequence of the constant domain of their heavy chains. Heavy chains are classified as mu (μ), delta (Δ), gamma (γ), alpha (α), and epsilon (ε), and define the antibody's isotype as IgM, IgD, IgG, IgA, and IgE, respectively. Several of these may be further divided into subclasses or isotypes, e.g. IgG1, IgG2, IgG3, IgG4, IgA1 and IgA2. Different isotypes have different effector functions; for example, IgG1 and IgG3 isotypes have antibody-dependent cellular cytotoxicity (ADCC) activity. Human light chains are classified as kappa (κ) and lambda (λ) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)).

For a detailed description of the structure and generation of antibodies, see Roth, D. B., and Craig, N.L., *Cell,* 94:411-414 (1998), herein incorporated by reference in its entirety. Briefly, the process for generating DNA encoding the heavy and light chain immunoglobulin sequences occurs primarily in developing B-cells. Prior to the rearranging and joining of various immunoglobulin gene segments, the V, D, J and constant (C) gene segments are found generally in relatively close proximity on a single chromosome. During B-cell-differentiation, one of each of the appropriate family members of the V, D, J (or only V and J in the case of light chain genes) gene segments are recombined to form functionally rearranged variable regions of the heavy and light immunoglobulin genes. This gene segment rearrangement process appears to be sequential. First, heavy chain D-to-J joints are made, followed by heavy chain V-to-DJ joints and light chain V-to-J joints. In addition to the rearrangement of V, D and J segments, further diversity is generated in the primary repertoire of immunoglobulin heavy and light chains by way of variable recombination at the locations where the V and J segments in the light chain are joined and where the D and J segments of the heavy chain are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity. The net effect of such rearrangements in the variable region gene segments and the variable recombination which may occur during such joining is the production of a primary antibody repertoire.

"Antibody fragments" comprise a portion of an intact full length antibody (including, e.g., human antibodies), preferably the antigen binding or variable region of the intact antibody, and include multispecific antibodies formed from antibody fragments. Nonlimiting examples of antibody fragments include Fab, Fab', F(ab')2, Fv, domain antibody (dAb), complementarity determining region (CDR) fragments, single-chain antibodies (scFv), single chain antibody fragments, diabodies, triabodies, tetrabodies, minibodies, linear antibodies (Zapata et al., Protein Eng., 8(10):1057-1062 (1995)); chelating recombinant antibodies, tribodies or bibodies, intrabodies, nanobodies, small modular immunopharmaceuticals (SMIPs), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen binding to the polypeptide, such as a CDR sequence, as long as the antibody retains the desired biological activity.

Papain digestion of antibodies produces two identical antigen-binding fragments, called "Fab" fragments, each with a single antigen-binding site, and a residual "Fc" fragment, whose name reflects its ability to crystallize 35 readily. Pepsin treatment yields an F(ab')2 fragment that has two "Fv" fragments. An "Fv" fragment is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH VL dimer. Collectively, the six CDRs confer antigen-binding specificity to the antibody. However, even a single variable domain (or half of an Fv comprising only three CDRs specific for an antigen) has the ability to recognize and bind antigen.

"Single-chain Fv" or "sFv" or "scFv" antibody fragments comprise the VH and VL domains of antibody, wherein these domains are present in a single polypeptide chain. Preferably, the Fv polypeptide further comprises a polypeptide linker between the VH and VL domains that enables the Fv to form the desired structure for antigen binding. For a review of scFv see Pluckthun in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them.

The term "hypervariable" region refers to the amino acid residues of an antibody which are responsible for antigen-binding. The hypervariable region comprises amino acid residues from a "complementarity determining region" or CDR [i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5$^{th}$ Ed. Public Health Service, National Institutes of Health, Bethesda, Md. (1991)] and/or those residues from a hypervariable loop (i.e., residues 26-32 (L1), 50-52 (L2) and 91-96 (L3) in the light chain variable domain and 26-32 (H1), 53-55 (H2) and 96-101 (H3) in the heavy chain variable domain as described by [Chothia et al., J. Mol. Biol. 196: 901-917 (1987)].

"Framework" or FR residues are those variable domain residues other than the hypervariable region residues.

The phrase "constant region" refers to the portion of the antibody molecule that confers effector functions.

The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

The term "mutein" refers to the polypeptide sequence of an antibody that contains at least one amino acid substitution, deletion, or insertion in the variable region or the portion equivalent to the variable region, provided that the mutein retains the desired binding affinity or biological activity. Muteins may be substantially homologous or substantially identical to the parent antibody.

The term "derivative" when used in connection with antibodies of the invention refers to antibodies covalently modified by such techniques as ubiquitination, conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. Derivatives of the invention will retain the binding properties of underivatized molecules of the invention.

When used herein, the term "antibody" specifically includes any one of the following that retain the ability to bind the extracellular portion of EphB3:

1) an amino acid mutein of a parent antibody having an amino acid sequence set out in FIG. 7, including muteins comprising a variable heavy chain amino acid sequence which is at least 60, 65, 70, 75, 80, 85, 90, 91, 92, 93, 94, 95, 96, 97, 98, or 99% homologous to the parent amino acid sequence, and/or comprising a variable light chain amino acid sequence which is at least 60, 65, 70, 75, 80, 85, 90, 91, 92, 93, 94, 95, 96, 97, 98, or 99% homologous to the parent amino acid sequence, taking into account similar amino acids for the homology determination;

2) EphB3-binding polypeptides comprising one or more complementary determining regions (CDRs) of a parent antibody having an amino acid sequence set out in FIG. 7, preferably comprising at least CDR3 of the heavy chain, and preferably comprising two or more, or three or more, or four or more, or five or more, or all six CDRs;

3) Human Engineered™ antibodies generated by altering the parent sequence according to the methods set forth in Studnicka et al., U.S. Pat. No. 5,766,886 and Example 8 herein, using Kabat numbering to identify low, moderate and high risk residues; such antibodies comprising at least one of the following heavy chains and at least one of the following light chains: (a) a heavy chain in which all of the low risk rodent residues that differ from corresponding residues in a human reference immunoglobulin sequence have been modified to be the same as the human residue in the human reference immunoglobulin sequence or (b) a heavy chain in which all of the low and moderate risk rodent residues have been modified, if necessary, to be the same residues as in the human reference immunoglobulin sequence, (c) a light chain in which all of the low risk residues have been modified, if necessary, to be the same residues as a human reference immunoglobulin sequence or (b) a light chain in which all of the low and moderate risk residues have been modified, if necessary, to be the same residues as a human reference immunoglobulin sequence 4) muteins of the aforementioned antibodies in preceding paragraph (3) comprising a heavy or light chain or heavy or light chain variable regions having at least 60% amino acid sequence identity with the original rodent light chain, more preferably at least 80%, more preferably at least 85%, more preferably at least 90%, and most preferably at least 95%, including for example, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, and 100% identical;

5) EphB3-binding polypeptides comprising the high risk residues of one or more CDRs of the rodent antibody, and preferably comprising high risk residues of two or more, or three or more, or four or more, or five or more, or all six CDRs, and optionally comprising one or more changes at the low or moderate risk residues;

for example, comprising one or more changes at a low risk residue and conservative substitutions at a moderate risk residue, or for example, retaining the moderate and high risk amino acid residues and comprising one or more changes at a low risk residue, where changes include insertions, deletions or substitutions and may be conservative substitutions or may cause the engineered antibody to be closer in sequence to a human light chain or heavy chain sequence, a human germline light chain or heavy chain sequence, a consensus human light chain or heavy chain sequence, or a consensus human germline light chain or heavy chain sequence. Such contemplated changes may also be displayed in sequence format as follows. In a hypothetical sequence of AKKLVHTPYSFKEDF (SEQ ID NO: 426), where the respective risk allotted to each residue according to Studnicka et al., U.S. Pat. No. 5,766,886, is HMLHMLHMLHMLHML (H=high, M=medium, L=low), exemplary changes to the low risk residues of the hypothetical sequence may be displayed as: AKXLVXTPXSFXEDX (SEQ ID NO: 427) where X is any amino acid, or alternatively where X is a conservative substitution of the original residue at that position, and exemplary changes to the low and moderate risk residues can be displayed similarly, e.g. AYXLYXTYXSYXEYX (SEQ ID NO: 428), where X is any amino acid and Y is a conservative substitution of the original residue at that position.

The term "competing antibody" includes 1) a non-murine or non-rodent monoclonal antibody that binds to the same epitope of EphB3 as murine antibody XHA.05.465, XHA.05.783, XHA.05.031, XHA.05.942, XHA.05.751, XHA.05.599, XPA.04.031, XPA.04.030, XPA.04.040, XHA.05.119, XHA.05.228, XHA.05.337, XHA.05.440, XPA.04.022, XHA.05.964, XHA.05.653, XHA.05.885, XPA.04.001, XPA.04.013, XPA.04.018, XPA.04.036, XPA.04.046, XPA.04.048, XHA.05.660, XHA.05.552, XHA.05.949, XHA.05.151, XPA.04.019, XHA.05.676, XHA.05.030, XHA.05.200, XHA.05.005, XHA.05.001, XHA.05.888, or XHA.05.111, e.g. as determined through X-ray crystallography; and 2) a non-murine or non-rodent monoclonal antibody that competes with murine antibody XHA.05.465, XHA.05.783, XHA.05.031, XHA.05.942, XHA.05.751, XHA.05.599, XPA.04.031, XPA.04.030, XPA.04.040, XHA.05.119, XHA.05.228, XHA.05.337, XHA.05.440, XPA.04.022, XHA.05.964, XHA.05.653, XHA.05.885, XPA.04.001, XPA.04.013, XPA.04.018, XPA.04.036, XPA.04.046, XPA.04.048, XHA.05.660, XHA.05.552, XHA.05.949, XHA.05.151, XPA.04.019, XHA.05.676, XHA.05.030, XHA.05.200, XHA.05.005, XHA.05.001, XHA.05.888, or XHA.05.111 by more than 75%, more than 80%, or more than 81%, 82%, 83%, 84%, 85%, 86%, 87%, 88%, 89%, 90%, 91%, 92%, 93%, 94% or 95%.

Antibodies of the invention preferably bind to the ECD of EphB3 with an affinity $K_D$ of at least $10^{-6}$, $10^{-7}$, $10^{-8}$, $10^{-9}$, $10^{-10}$ or $10^{-11}$ M or less and preferably inducing receptor phosphorylation, oligomerization, internalization, degradation, signaling, and/or EphB3-mediated cell-cell adhesion.

Optionally, any chimeric, human or humanized antibody publicly disclosed before the filing date hereof, or disclosed in an application filed before the filing date hereof, is excluded from the scope of the invention.

"Non-rodent" monoclonal antibody is any antibody, as broadly defined herein, that is not a complete intact rodent monoclonal antibody generated by a rodent hybridoma. Thus, non-rodent antibodies specifically include, but are not limited to, muteins of rodent antibodies, rodent antibody fragments, linear antibodies, chimeric antibodies, humanized antibodies, Human Engineered™ antibodies and human antibodies, including human antibodies produced from transgenic animals or via phage display technology. Similarly, non-murine antibodies include but are not limited to muteins of murine antibodies, murine antibody fragments, linear antibodies, chimeric, humanized, Human Engineered™ and human antibodies.

Target Antigen

The target antigen to be used for production of antibodies may be, e.g., the extracellular portion of EphB3, or a fragment thereof that retains the desired epitope, optionally fused to another polypeptide that allows the epitope to be displayed in its native conformation. Alternatively, intact EphB3 expressed at the surface of cells can be used to generate antibodies. Such cells can be transformed to express EphB3 or may be other naturally occurring cells that express EphB3. Other forms of EphB3 polypeptides useful for generating antibodies will be apparent to those skilled in the art.

In one embodiment, the antibodies of the present invention bind to an epitope of EphB3, wherein the epitope is selected from the group consisting of SEQ ID NOS:11-421 set forth in Table 1. In some embodiments the domain is selected from the group consisting of the ligand binding domain (amino acid residues 39-212 of SEQ ID NO: 2), the TNFR domain (amino acid residues 256-331 of SEQ ID NO: 2), the 1st fibronectin domain (amino acid residues 340-435 of SEQ ID NO: 2), and the 2nd fibronectin domain (amino acid residues 453-535 of SEQ ID NO: 2). In some embodiments the antibodies of the present invention bind to an epitope of the ligand binding domain of EphB3, the epitope selected from the group consisting of SEQ ID NOS:11-145. In some embodiments the antibodies of the present invention bind to an epitope of the TNFR domain of EphB3, the epitope selected from the group consisting of SEQ ID NOS:161-259. In some embodiments the antibodies of the present invention bind to an epitope of the 1st fibronectin domain of EphB3, the epitope selected from the group consisting of SEQ ID NOS:259-301. In some embodiments the antibodies of the present invention bind to an epitope of the 2nd fibronectin domain of EphB3, the epitope selected from the group consisting of SEQ ID NOS:380-421.

Table 1 below provides regions of EphB3 (SEQ ID NO:2) that have been identified as linear epitopes suitable for recognition by anti EphB3 antibodies.

TABLE 1

| Mapped region (aa) | epitope length | epitope | aa seq location | epitope # | SEQ ID NO: |
|---|---|---|---|---|---|
| 98-115 | 8-mer | WRRDVQRV | 98-105 | 1 | 11 |
| 98-115 | 8-mer | RRDVQRVY | 99-106 | 2 | 12 |
| 98-115 | 8-mer | RDVQRVYV | 100-107 | 3 | 13 |
| 98-115 | 8-mer | DVQRVYVE | 101-108 | 4 | 14 |
| 98-115 | 8-mer | VQRVYVEL | 102-109 | 5 | 15 |
| 98-115 | 8-mer | QRVYVELK | 103-110 | 6 | 16 |
| 98-115 | 8-mer | RVYVELKF | 104-111 | 7 | 17 |
| 98-115 | 8-mer | VYVELKFT | 105-112 | 8 | 18 |
| 98-115 | 8-mer | YVELKFTV | 106-113 | 9 | 19 |
| 98-115 | 8-mer | VELKFTVR | 107-114 | 10 | 20 |
| 98-115 | 8-mer | ELKFTVRD | 108-115 | 11 | 21 |
| 98-115 | 9-mer | WRRDVQRVY | 98-106 | 12 | 22 |
| 98-115 | 9-mer | RRDVQRVYV | 99-107 | 13 | 23 |
| 98-115 | 9-mer | RDVQRVYVE | 100-108 | 14 | 24 |
| 98-115 | 9-mer | DVQRVYVEL | 101-109 | 15 | 25 |
| 98-115 | 9-mer | VQRVYVELK | 102-110 | 16 | 26 |
| 98-115 | 9-mer | QRVYVELKF | 103-111 | 17 | 27 |
| 98-115 | 9-mer | RVYVELKFT | 104-112 | 18 | 28 |
| 98-115 | 9-mer | VYVELKFTV | 105-113 | 19 | 29 |
| 98-115 | 9-mer | YVELKFTVR | 106-114 | 20 | 30 |
| 98-115 | 9-mer | VELKFTVRD | 107-115 | 21 | 31 |
| 98-115 | 10-mer | WRRDVQRVYV | 98-107 | 22 | 32 |
| 98-115 | 10-mer | RRDVQRVYVE | 99-108 | 23 | 33 |
| 98-115 | 10-mer | RDVQRVYVEL | 100-109 | 24 | 34 |
| 98-115 | 10-mer | DVQRVYVELK | 101-110 | 25 | 35 |
| 98-115 | 10-mer | VQRVYVELKF | 102-111 | 26 | 36 |
| 98-115 | 10-mer | QRVYVELKFT | 103-112 | 27 | 37 |
| 98-115 | 10-mer | RVYVELKFTV | 104-113 | 28 | 38 |
| 98-115 | 10-mer | VYVELKFTVR | 105-114 | 29 | 39 |
| 98-115 | 10-mer | YVELKFTVRD | 106-115 | 30 | 40 |
| 152-194 | 8-mer | NPYVKVDT | 152-159 | 1 | 41 |
| 152-194 | 8-mer | PYVKVDTI | 153-160 | 2 | 42 |
| 152-194 | 8-mer | YVKVDTIA | 154-161 | 3 | 43 |
| 152-194 | 8-mer | VKVDTIAP | 155-162 | 4 | 44 |
| 152-194 | 8-mer | KVDTIAPD | 156-163 | 5 | 45 |
| 152-194 | 8-mer | VDTIAPDE | 157-164 | 6 | 46 |
| 152-194 | 8-mer | DTIAPDES | 158-165 | 7 | 47 |
| 152-194 | 8-mer | TIAPDESF | 159-166 | 8 | 48 |

TABLE 1-continued

| Mapped region (aa) | epitope length | epitope | aa seq location | epitope # | SEQ ID NO: |
|---|---|---|---|---|---|
| 152-194 | 8-mer | IAPDESFS | 160-167 | 9 | 49 |
| 152-194 | 8-mer | APDESFSR | 161-168 | 10 | 50 |
| 152-194 | 8-mer | PDESFSRL | 162-169 | 11 | 51 |
| 152-194 | 8-mer | DESFSRLD | 163-170 | 12 | 52 |
| 152-194 | 8-mer | ESFSRLDA | 164-171 | 13 | 53 |
| 152-194 | 8-mer | SFSRLDAG | 165-172 | 14 | 54 |
| 152-194 | 8-mer | FSRLDAGR | 166-173 | 15 | 55 |
| 152-194 | 8-mer | SRLDAGRV | 167-174 | 16 | 56 |
| 152-194 | 8-mer | RLDAGRVN | 168-175 | 17 | 57 |
| 152-194 | 8-mer | LDAGRVNT | 169-176 | 18 | 58 |
| 152-194 | 8-mer | DAGRVNTK | 170-177 | 19 | 59 |
| 152-194 | 8-mer | AGRVNTKV | 171-178 | 20 | 60 |
| 152-194 | 8-mer | GRVNTKVR | 172-179 | 21 | 61 |
| 152-194 | 8-mer | RVNTKVRS | 173-180 | 22 | 62 |
| 152-194 | 8-mer | VNTKVRSF | 174-181 | 23 | 63 |
| 152-194 | 8-mer | NTKVRSFG | 175-182 | 24 | 64 |
| 152-194 | 8-mer | TKVRSFGP | 176-183 | 25 | 65 |
| 152-194 | 8-mer | KVRSFGPL | 177-184 | 26 | 66 |
| 152-194 | 8-mer | VRSFGPLS | 178-185 | 27 | 67 |
| 152-194 | 8-mer | RSFGPLSK | 179-186 | 28 | 68 |
| 152-194 | 8-mer | SFGPLSKA | 180-187 | 29 | 69 |
| 152-194 | 8-mer | FGPLSKAG | 181-188 | 30 | 70 |
| 152-194 | 8-mer | GPLSKAGF | 182-189 | 31 | 71 |
| 152-194 | 8-mer | PLSKAGFY | 183-190 | 32 | 72 |
| 152-194 | 8-mer | LSKAGFYL | 184-191 | 33 | 73 |
| 152-194 | 8-mer | SKAGFYLA | 185-192 | 34 | 74 |
| 152-194 | 8-mer | KAGFYLAF | 186-193 | 35 | 75 |
| 152-194 | 8-mer | AGFYLAFQ | 187-194 | 36 | 76 |
| 152-194 | 9-mer | NPYVKVDTI | 152-160 | 37 | 77 |
| 152-194 | 9-mer | PYVKVDTIA | 153-161 | 38 | 78 |
| 152-194 | 9-mer | YVKVDTIAP | 154-162 | 39 | 79 |
| 152-194 | 9-mer | VKVDTIAPD | 155-163 | 40 | 80 |
| 152-194 | 9-mer | KVDTIAPDE | 156-164 | 41 | 81 |
| 152-194 | 9-mer | VDTIAPDES | 157-165 | 42 | 82 |
| 152-194 | 9-mer | DTIAPDESF | 158-166 | 43 | 83 |
| 152-194 | 9-mer | TIAPDESFS | 159-167 | 44 | 84 |
| 152-194 | 9-mer | IAPDESFSR | 160-168 | 45 | 85 |
| 152-194 | 9-mer | APDESFSRL | 161-169 | 46 | 86 |

TABLE 1-continued

| Mapped region (aa) | epitope length | epitope | aa seq location | epitope # | SEQ ID NO: |
|---|---|---|---|---|---|
| 152-194 | 9-mer | PDESFSRLD | 162-170 | 47 | 87 |
| 152-194 | 9-mer | DESFSRLDA | 163-171 | 48 | 88 |
| 152-194 | 9-mer | ESFSRLDAG | 164-172 | 49 | 89 |
| 152-194 | 9-mer | SFSRLDAGR | 165-173 | 50 | 90 |
| 152-194 | 9-mer | FSRLDAGRV | 166-174 | 51 | 91 |
| 152-194 | 9-mer | SRLDAGRVN | 167-175 | 52 | 92 |
| 152-194 | 9-mer | RLDAGRVNT | 168-176 | 53 | 93 |
| 152-194 | 9-mer | LDAGRVNTK | 169-177 | 54 | 94 |
| 152-194 | 9-mer | DAGRVNTKV | 170-178 | 55 | 95 |
| 152-194 | 9-mer | AGRVNTKVR | 171-179 | 56 | 96 |
| 152-194 | 9-mer | GRVNTKVRS | 172-180 | 57 | 97 |
| 152-194 | 9-mer | RVNTKVRSF | 173-181 | 58 | 98 |
| 152-194 | 9-mer | VNTKVRSFG | 174-182 | 59 | 99 |
| 152-194 | 9-mer | NTKVRSFGP | 175-183 | 60 | 100 |
| 152-194 | 9-mer | TKVRSFGPL | 176-184 | 61 | 101 |
| 152-194 | 9-mer | KVRSFGPLS | 177-185 | 62 | 102 |
| 152-194 | 9-mer | VRSFGPLSK | 178-186 | 63 | 103 |
| 152-194 | 9-mer | RSFGPLSKA | 179-187 | 64 | 104 |
| 152-194 | 9-mer | SFGPLSKAG | 180-188 | 65 | 105 |
| 152-194 | 9-mer | FGPLSKAGF | 181-189 | 66 | 106 |
| 152-194 | 9-mer | GPLSKAGFY | 182-190 | 67 | 107 |
| 152-194 | 9-mer | PLSKAGFYL | 183-191 | 68 | 108 |
| 152-194 | 9-mer | LSKAGFYLA | 184-192 | 69 | 109 |
| 152-194 | 9-mer | SKASFYLAF | 185-193 | 70 | 110 |
| 152-194 | 9-mer | KAGFYLAFQ | 186-194 | 71 | 111 |
| 152-194 | 10-mer | NPYVKVDTIA | 152-161 | 72 | 112 |
| 152-194 | 10-mer | PYVKVDTIAP | 153-162 | 73 | 113 |
| 152-194 | 10-mer | YVKVDTIAPD | 154-163 | 74 | 114 |
| 152-194 | 10-mer | VKVDTIAPDE | 155-164 | 75 | 115 |
| 152-194 | 10-mer | KVDTIAPDES | 156-165 | 76 | 116 |
| 152-194 | 10-mer | VDTIAPDESF | 157-166 | 77 | 117 |
| 152-194 | 10-mer | DTIAPDESFS | 158-167 | 78 | 118 |
| 152-194 | 10-mer | TIAPDESFSR | 159-168 | 79 | 119 |
| 152-194 | 10-mer | IAPDESFSRL | 160-169 | 80 | 120 |
| 152-194 | 10-mer | APDESFSRLD | 161-170 | 81 | 121 |
| 152-194 | 10-mer | PDESFSRLDA | 162-171 | 82 | 122 |
| 152-194 | 10-mer | DESFSRLDAG | 163-172 | 83 | 123 |
| 152-194 | 10-mer | ESFSRLDASR | 164-173 | 84 | 124 |
| 152-194 | 10-mer | SFSRLDAGRV | 165-174 | 85 | 125 |
| 152-194 | 10-mer | FSRLDAGRVN | 166-175 | 86 | 126 |
| 152-194 | 10-mer | SRLDAGRVNT | 167-176 | 87 | 127 |
| 152-194 | 10-mer | RLDAGRVNTK | 168-177 | 88 | 128 |
| 152-194 | 10-mer | LDAGRVNTKV | 169-178 | 89 | 129 |
| 152-194 | 10-mer | DAGRVNTKVR | 170-179 | 90 | 130 |
| 152-194 | 10-mer | AGRVNTKVRS | 171-180 | 91 | 131 |
| 152-194 | 10-mer | GRVNTKVRSF | 172-181 | 92 | 132 |
| 152-194 | 10-mer | RVNTKVRSFG | 173-182 | 93 | 133 |
| 152-194 | 10-mer | VNTKVRSFGP | 174-183 | 94 | 134 |
| 152-194 | 10-mer | NTKVRSFGPL | 175-184 | 95 | 135 |
| 152-194 | 10-mer | TKVRSFGPLS | 176-185 | 96 | 136 |
| 152-194 | 10-mer | KVRSFGPLSK | 177-186 | 97 | 137 |
| 152-194 | 10-mer | VRSFGPLSKA | 178-187 | 98 | 138 |
| 152-194 | 10-mer | RSFGPLSKAG | 179-188 | 99 | 139 |
| 152-194 | 10-mer | SFGPLSKAGF | 180-189 | 100 | 140 |
| 152-194 | 10-mer | FGPLSKAGFY | 181-190 | 101 | 141 |
| 152-194 | 10-mer | GPLSKAGFYL | 182-191 | 102 | 142 |
| 152-194 | 10-mer | PLSKAGFYLA | 183-192 | 103 | 143 |
| 152-194 | 10-mer | LSKASFYLAF | 184-193 | 104 | 144 |
| 152-194 | 10-mer | SKAGFYLAFQ | 185-194 | 105 | 145 |
| 244-256 | 8-mer | NAVEVSVP | 244-251 | 1 | 146 |
| 244-256 | 8-mer | AVEVSVPL | 245-252 | 2 | 147 |
| 244-256 | 8-mer | VEVSVPLK | 246-253 | 3 | 148 |
| 244-256 | 8-mer | EVSVPLKL | 247-254 | 4 | 149 |
| 244-256 | 8-mer | VSVPLKLY | 248-255 | 5 | 150 |
| 244-256 | 8-mer | SVPLKLYC | 249-256 | 6 | 151 |
| 244-256 | 9-mer | NAVEVSVPL | 244-252 | 7 | 152 |
| 244-256 | 9-mer | AVEVSVPLK | 245-253 | 8 | 153 |
| 244-256 | 9-mer | VEVSVPLKL | 246-254 | 9 | 154 |
| 244-256 | 9-mer | EVSVPLKLY | 247-255 | 10 | 155 |
| 244-256 | 9-mer | VSVPLKLYC | 248-256 | 11 | 156 |
| 244-256 | 10-mer | NAVEVSVPLK | 244-253 | 12 | 157 |
| 244-256 | 10-mer | AVEVSVPLKL | 245-254 | 13 | 158 |
| 244-256 | 10-mer | VEVSVPLKLY | 246-255 | 14 | 159 |
| 244-256 | 10-mer | EVSVPLKLYC | 247-256 | 15 | 160 |
| 274-298 | 8-mer | GHEPAAKE | 274-281 | 1 | 161 |
| 274-298 | 8-mer | HEPAAKES | 275-282 | 2 | 162 |

TABLE 1-continued

| Mapped region (aa) | epitope length | epitope | aa seq location | epitope # | SEQ ID NO: |
|---|---|---|---|---|---|
| 274-298 | 8-mer | EPAAKESQ | 276-283 | 3 | 163 |
| 274-298 | 8-mer | PAAKESQC | 277-284 | 4 | 164 |
| 274-298 | 8-mer | AAKESQCR | 278-285 | 5 | 165 |
| 274-298 | 8-mer | AKESQCRP | 279-286 | 6 | 166 |
| 274-298 | 8-mer | KESQCRPC | 280-287 | 7 | 167 |
| 274-298 | 8-mer | ESQCRPCP | 281-288 | 8 | 168 |
| 274-298 | 8-mer | SQCRPCPP | 282-289 | 9 | 169 |
| 274-298 | 8-mer | QCRPCPPG | 283-290 | 10 | 170 |
| 274-298 | 8-mer | CRPCPPGS | 284-291 | 11 | 171 |
| 274-298 | 8-mer | RPCPPGSY | 285-292 | 12 | 172 |
| 274-298 | 8-mer | PCPPGSYK | 286-293 | 13 | 173 |
| 274-298 | 8-mer | CPPGSYKA | 287-294 | 14 | 174 |
| 274-298 | 8-mer | PPGSYKAK | 288-295 | 15 | 175 |
| 274-298 | 8-mer | PGSYKAKQ | 289-296 | 16 | 176 |
| 274-298 | 8-mer | GSYKAKQG | 290-297 | 17 | 177 |
| 274-298 | 8-mer | SYKAKQGE | 291-298 | 18 | 178 |
| 274-298 | 9-mer | GHEPAAKES | 274-282 | 19 | 179 |
| 274-298 | 9-mer | HEPAAKESQ | 275-283 | 20 | 180 |
| 274-298 | 9-mer | EPAAKESQC | 276-284 | 21 | 181 |
| 274-298 | 9-mer | PAAKESQCR | 277-285 | 22 | 182 |
| 274-298 | 9-mer | AAKESQCRP | 278-286 | 23 | 183 |
| 274-298 | 9-mer | AKESQCRPC | 279-287 | 24 | 184 |
| 274-298 | 9-mer | KESQCRPCP | 280-288 | 25 | 185 |
| 274-298 | 9-mer | ESQCRPCPP | 281-289 | 26 | 186 |
| 274-298 | 9-mer | SQCRPCPPG | 282-290 | 27 | 187 |
| 274-298 | 9-mer | QCRPCPPGS | 283-291 | 28 | 188 |
| 274-298 | 9-mer | CRPCPPGSY | 284-292 | 29 | 189 |
| 274-298 | 9-mer | RPCPPGSYK | 285-293 | 30 | 190 |
| 274-298 | 9-mer | PCPPGSYKA | 286-294 | 31 | 191 |
| 274-298 | 9-mer | CPPGSYKAK | 287-295 | 32 | 192 |
| 274-298 | 9-mer | PPGSYKAKQ | 288-296 | 33 | 193 |
| 274-298 | 9-mer | PGSYKAKQG | 289-297 | 34 | 194 |
| 274-298 | 9-mer | GSYKAKQGE | 290-298 | 35 | 195 |
| 274-298 | 10-mer | GHEPAAKESQ | 274-283 | 36 | 196 |
| 274-298 | 10-mer | HEPAAKESQC | 275-284 | 37 | 197 |
| 274-298 | 10-mer | EPAAKESQCR | 276-285 | 38 | 198 |
| 274-298 | 10-mer | PAAKESQCRP | 277-286 | 39 | 199 |
| 274-298 | 10-mer | AAKESQCRPC | 278-287 | 40 | 200 |
| 274-298 | 10-mer | AKESQCRPCP | 279-288 | 41 | 201 |
| 274-298 | 10-mer | KESQCRPCPP | 280-289 | 42 | 202 |
| 274-298 | 10-mer | ESQCRPCPPG | 281-290 | 43 | 203 |
| 274-298 | 10-mer | SQCRPCPPGS | 282-291 | 44 | 204 |
| 274-298 | 10-mer | QCRPCPPGSY | 283-292 | 45 | 205 |
| 274-298 | 10-mer | CRPCPPGSYK | 284-293 | 46 | 206 |
| 274-298 | 10-mer | RPCPPGSYKA | 285-294 | 47 | 207 |
| 274-298 | 10-mer | PCPPGSYKAK | 286-295 | 48 | 208 |
| 274-298 | 10-mer | CPPGSYKAKQ | 287-296 | 49 | 209 |
| 274-298 | 10-mer | PPGSYKAKQG | 288-297 | 50 | 210 |
| 274-298 | 10-mer | PGSYKAKQGE | 289-298 | 51 | 211 |
| 313-336 | 8-mer | PAASICTC | 313-320 | 1 | 212 |
| 313-336 | 8-mer | AASICTCH | 314-321 | 2 | 213 |
| 313-336 | 8-mer | ASICTCHN | 315-322 | 3 | 214 |
| 313-336 | 8-mer | SICTCHNN | 316-323 | 4 | 215 |
| 313-336 | 8-mer | ICTCHNNF | 317-324 | 5 | 216 |
| 313-336 | 8-mer | CTCHNNFY | 318-325 | 6 | 217 |
| 313-336 | 8-mer | TCHNNFYR | 319-326 | 7 | 218 |
| 313-336 | 8-mer | CHNNFYRA | 320-327 | 8 | 219 |
| 313-336 | 8-mer | HNNFYRAD | 321-328 | 9 | 220 |
| 313-336 | 8-mer | NNFYRADS | 322-329 | 10 | 221 |
| 313-336 | 8-mer | NFYRADSD | 323-330 | 11 | 222 |
| 313-336 | 8-mer | FYRADSDS | 324-331 | 12 | 223 |
| 313-336 | 8-mer | YRADSDSA | 325-332 | 13 | 224 |
| 313-336 | 8-mer | RADSDSAD | 326-333 | 14 | 225 |
| 313-336 | 8-mer | ADSDSADS | 327-334 | 15 | 226 |
| 313-336 | 8-mer | DSDSADSA | 328-335 | 16 | 227 |
| 313-336 | 8-mer | SDSADSAC | 329-336 | 17 | 228 |
| 313-336 | 9-mer | PAASICTCH | 313-321 | 18 | 229 |
| 313-336 | 9-mer | AASICTCHN | 314-322 | 19 | 230 |
| 313-336 | 9-mer | ASICTCHNN | 315-323 | 20 | 231 |
| 313-336 | 9-mer | SICTCHNNF | 316-324 | 21 | 232 |
| 313-336 | 9-mer | ICTCHNNFY | 317-325 | 22 | 233 |
| 313-336 | 9-mer | CTCHNNFYR | 318-326 | 23 | 234 |
| 313-336 | 9-mer | TCHNNFYRA | 319-327 | 24 | 235 |
| 313-336 | 9-mer | CHNNFYRAD | 320-328 | 25 | 236 |
| 313-336 | 9-mer | HNNFYRADS | 321-329 | 26 | 237 |
| 313-336 | 9-mer | NNFYRADSD | 322-330 | 27 | 238 |

TABLE 1-continued

| Mapped region (aa) | epitope length | epitope | aa seq location | epitope # | SEQ ID NO: |
|---|---|---|---|---|---|
| 313-336 | 9-mer | NFYRADSDS | 323-331 | 28 | 239 |
| 313-336 | 9-mer | FYRADSDSA | 324-332 | 29 | 240 |
| 313-336 | 9-mer | YRADSDSAD | 325-333 | 30 | 241 |
| 313-336 | 9-mer | RADSDSADS | 326-334 | 31 | 242 |
| 313-336 | 9-mer | ADSDSADSA | 327-335 | 32 | 243 |
| 313-336 | 9-mer | DSDSADSAC | 328-336 | 33 | 244 |
| 313-336 | 10-mer | PAASICTCHN | 313-322 | 34 | 245 |
| 313-336 | 10-mer | AASICTCHNN | 314-323 | 35 | 246 |
| 313-336 | 10-mer | ASICTCHNNF | 315-324 | 36 | 247 |
| 313-336 | 10-mer | SICTCHNNFY | 316-325 | 37 | 248 |
| 313-336 | 10-mer | ICTCHNNFYR | 317-326 | 38 | 249 |
| 313-336 | 10-mer | CTCHNNFYRA | 318-327 | 39 | 250 |
| 313-336 | 10-mer | TCHNNFYRAD | 319-328 | 40 | 251 |
| 313-336 | 10-mer | CHNNFYRADS | 320-329 | 41 | 252 |
| 313-336 | 10-mer | HNNFYRADSD | 321-330 | 42 | 253 |
| 313-336 | 10-mer | NNFYRADSDS | 322-331 | 43 | 254 |
| 313-336 | 10-mer | NFYRADSDSA | 323-332 | 44 | 255 |
| 313-336 | 10-mer | FYRADSDSAD | 324-333 | 45 | 256 |
| 313-336 | 10-mer | YRADSDSADS | 325-334 | 46 | 257 |
| 313-336 | 10-mer | RADSDSADSA | 326-335 | 47 | 258 |
| 313-336 | 10-mer | ADSDSADSAC | 327-336 | 48 | 259 |
| 362-383 | 8-mer | PRDLGGRD | 362-369 | 1 | 260 |
| 362-383 | 8-mer | RDLGGRDD | 363-370 | 2 | 261 |
| 362-383 | 8-mer | DLGGRDDL | 364-371 | 3 | 262 |
| 362-383 | 8-mer | LGGRDDLL | 365-372 | 4 | 263 |
| 362-383 | 8-mer | GGRDDLLY | 366-373 | 5 | 264 |
| 362-383 | 8-mer | GRDDLLYN | 367-374 | 6 | 265 |
| 362-383 | 8-mer | RDDLLYNV | 368-375 | 7 | 266 |
| 362-383 | 8-mer | DDLLYNVI | 369-376 | 8 | 267 |
| 362-383 | 8-mer | DLLYNVIC | 370-377 | 9 | 268 |
| 362-383 | 8-mer | LLYNVICK | 371-378 | 10 | 269 |
| 362-383 | 8-mer | LYNVICKK | 372-379 | 11 | 270 |
| 362-383 | 8-mer | YNVICKKC | 373-380 | 12 | 271 |
| 362-383 | 8-mer | NVICKKCH | 374-381 | 13 | 272 |
| 362-383 | 8-mer | VICKKCHG | 375-382 | 14 | 273 |
| 362-383 | 8-mer | ICKKCHGA | 376-383 | 15 | 274 |
| 362-383 | 9-mer | PRDLGGRDD | 362-370 | 16 | 275 |
| 362-383 | 9-mer | RDLGGRDDL | 363-371 | 17 | 276 |
| 362-383 | 9-mer | DLGGRDDLL | 364-372 | 18 | 277 |
| 362-383 | 9-mer | LGGRDDLLY | 365-373 | 19 | 278 |
| 362-383 | 9-mer | GGRDDLLYN | 366-374 | 20 | 279 |
| 362-383 | 9-mer | GRDDLLYNV | 367-375 | 21 | 280 |
| 362-383 | 9-mer | RDDLLYNVI | 368-376 | 22 | 281 |
| 362-383 | 9-mer | DDLLYNVIC | 369-377 | 23 | 282 |
| 362-383 | 9-mer | DLLYNVICK | 370-378 | 24 | 283 |
| 362-383 | 9-mer | LLYNVICKK | 371-379 | 25 | 284 |
| 362-383 | 9-mer | LYNVICKKC | 372-380 | 26 | 285 |
| 362-383 | 9-mer | YNVICKKCH | 373-381 | 27 | 286 |
| 362-383 | 9-mer | NVICKKCHG | 374-382 | 28 | 287 |
| 362-383 | 9-mer | VICKKCHGA | 375-383 | 29 | 288 |
| 362-383 | 10-mer | PRDLGGRDDL | 362-371 | 30 | 289 |
| 362-383 | 10-mer | RDLGGRDDLL | 363-372 | 31 | 290 |
| 362-383 | 10-mer | DLGGRDDLLY | 364-373 | 32 | 291 |
| 362-383 | 10-mer | LGGRDDLLYN | 365-374 | 33 | 292 |
| 362-383 | 10-mer | GGRDDLLYNV | 366-375 | 34 | 293 |
| 362-383 | 10-mer | GRDDLLYNVI | 367-376 | 35 | 294 |
| 362-383 | 10-mer | RDDLLYNVIC | 368-377 | 36 | 295 |
| 362-383 | 10-mer | DDLLYNVICK | 369-378 | 37 | 296 |
| 362-383 | 10-mer | DLLYNVICKK | 370-379 | 38 | 297 |
| 362-383 | 10-mer | LLYNVICKKC | 371-380 | 39 | 298 |
| 362-383 | 10-mer | LYNVICKKCH | 372-381 | 40 | 299 |
| 362-383 | 10-mer | YNVICKKCHG | 373-382 | 41 | 300 |
| 362-383 | 10-mer | NVICKKCHGA | 374-383 | 42 | 301 |
| 436-469 | 8-mer | PLPPRYAA | 436-443 | 1 | 302 |
| 436-469 | 8-mer | LPPRYAAV | 437-444 | 2 | 303 |
| 436-469 | 8-mer | PPRYAAVN | 438-445 | 3 | 304 |
| 436-469 | 8-mer | PRYAAVNI | 439-446 | 4 | 305 |
| 436-469 | 8-mer | RYAAVNIT | 440-447 | 5 | 306 |
| 436-469 | 8-mer | YAAVNITT | 441-448 | 6 | 307 |
| 436-469 | 8-mer | AAVNITTN | 442-449 | 7 | 308 |
| 436-469 | 8-mer | AVNITTNQ | 443-450 | 8 | 309 |
| 436-469 | 8-mer | VNITTNQA | 444-451 | 9 | 310 |
| 436-469 | 8-mer | NITTNQAA | 445-452 | 10 | 311 |
| 436-469 | 8-mer | ITTNQAAP | 446-453 | 11 | 312 |
| 436-469 | 8-mer | TTNQAAPS | 447-454 | 12 | 313 |
| 436-469 | 8-mer | TNQAAPSE | 448-455 | 13 | 314 |

TABLE 1-continued

| Mapped region (aa) | epitope length | epitope | aa seq location | epitope # | SEQ ID NO: |
|---|---|---|---|---|---|
| 436-469 | 8-mer | NQAAPSEV | 449-456 | 14 | 315 |
| 436-469 | 8-mer | QAAPSEVP | 450-457 | 15 | 316 |
| 436-469 | 8-mer | AAPSEVPT | 451-458 | 16 | 317 |
| 436-469 | 8-mer | APSEVPTL | 452-459 | 17 | 318 |
| 436-469 | 8-mer | PSEVPTLR | 453-460 | 18 | 319 |
| 436-469 | 8-mer | SEVPTLRL | 454-461 | 19 | 320 |
| 436-469 | 8-mer | EVPTLRLH | 455-462 | 20 | 321 |
| 436-469 | 8-mer | VPTLRLHS | 456-463 | 21 | 322 |
| 436-469 | 8-mer | PTLRLHSS | 457-464 | 22 | 323 |
| 436-469 | 8-mer | TLRLHSSS | 458-465 | 23 | 324 |
| 436-469 | 8-mer | LRLHSSSG | 459-466 | 24 | 325 |
| 436-469 | 8-mer | RLHSSSGS | 460-467 | 25 | 326 |
| 436-469 | 8-mer | LHSSSGSS | 461-468 | 26 | 327 |
| 436-469 | 8-mer | HSSSGSSL | 462-469 | 27 | 328 |
| 436-469 | 9-mer | PLPPRYAAV | 436-444 | 28 | 329 |
| 436-469 | 9-mer | LPPRYAAVN | 437-445 | 29 | 330 |
| 436-469 | 9-mer | PPRYAAVNI | 438-446 | 30 | 331 |
| 436-469 | 9-mer | PRYAAVNIT | 439-447 | 31 | 332 |
| 436-469 | 9-mer | RYAAVNITT | 440-448 | 32 | 333 |
| 436-469 | 9-mer | YAAVNITTN | 441-449 | 33 | 334 |
| 436-469 | 9-mer | AAVNITTNQ | 442-450 | 34 | 335 |
| 436-469 | 9-mer | AVNITTNQA | 443-451 | 35 | 336 |
| 436-469 | 9-mer | VNITTNQAA | 444-452 | 36 | 337 |
| 436-469 | 9-mer | NITTNQAAP | 445-453 | 37 | 338 |
| 436-469 | 9-mer | ITTNQAAPS | 446-454 | 38 | 339 |
| 436-469 | 9-mer | TTNQAAPSE | 447-455 | 39 | 340 |
| 436-469 | 9-mer | TNQAAPSEV | 448-456 | 40 | 341 |
| 436-469 | 9-mer | NQAAPSEVP | 449-457 | 41 | 342 |
| 436-469 | 9-mer | QAAPSEVPT | 450-458 | 42 | 343 |
| 436-469 | 9-mer | AAPSEVPTL | 451-459 | 43 | 344 |
| 436-469 | 9-mer | APSEVPTLR | 452-460 | 44 | 345 |
| 436-469 | 9-mer | PSEVPTLRL | 453-461 | 45 | 346 |
| 436-469 | 9-mer | SEVPTLRLH | 454-462 | 46 | 347 |
| 436-469 | 9-mer | EVPTLRLHS | 455-463 | 47 | 348 |
| 436-469 | 9-mer | VPTLRLHSS | 456-464 | 48 | 349 |
| 436-469 | 9-mer | PTLRLHSSS | 457-465 | 49 | 350 |
| 436-469 | 9-mer | TLRLHSSSG | 458-466 | 50 | 351 |
| 436-469 | 9-mer | LRLHSSSGS | 459-467 | 51 | 352 |
| 436-469 | 9-mer | RLHSSSGSS | 460-468 | 52 | 353 |
| 436-469 | 9-mer | LHSSSGSSL | 461-469 | 53 | 354 |
| 436-469 | 10-mer | PLPPRYAAVN | 436-445 | 54 | 355 |
| 436-469 | 10-mer | LPPRYAAVNI | 437-446 | 55 | 356 |
| 436-469 | 10-mer | PPRYAAVNIT | 438-447 | 56 | 357 |
| 436-469 | 10-mer | PRYAAVNITT | 439-448 | 57 | 358 |
| 436-469 | 10-mer | RYAAVNITTN | 440-449 | 58 | 359 |
| 436-469 | 10-mer | YAAVNITTNQ | 441-450 | 59 | 360 |
| 436-469 | 10-mer | AAVNITTNQA | 442-451 | 60 | 361 |
| 436-469 | 10-mer | AVNITTNQAA | 443-452 | 61 | 362 |
| 436-469 | 10-mer | VNITTNQAAP | 444-453 | 62 | 363 |
| 436-469 | 10-mer | NITTNQAAPS | 445-454 | 63 | 364 |
| 436-469 | 10-mer | ITTNQAAPSE | 446-455 | 64 | 365 |
| 436-469 | 10-mer | TTNQAAPSEV | 447-456 | 65 | 366 |
| 436-469 | 10-mer | TNQAAPSEVP | 448-457 | 66 | 367 |
| 436-469 | 10-mer | NQAAPSEVPT | 449-458 | 67 | 368 |
| 436-469 | 10-mer | QAAPSEVPTL | 450-459 | 68 | 369 |
| 436-469 | 10-mer | AAPSEVPTLR | 451-460 | 69 | 370 |
| 436-469 | 10-mer | APSEVPTLRL | 452-461 | 70 | 371 |
| 436-469 | 10-mer | PSEVPTLRLH | 453-462 | 71 | 372 |
| 436-469 | 10-mer | SEVPTLRLHS | 454-463 | 72 | 373 |
| 436-469 | 10-mer | EVPTLRLHSS | 455-464 | 73 | 374 |
| 436-469 | 10-mer | VPTLRLHSSS | 456-465 | 74 | 375 |
| 436-469 | 10-mer | PTLRLHSSSG | 457-466 | 75 | 376 |
| 436-469 | 10-mer | TLRLHSSSGS | 458-467 | 76 | 377 |
| 436-469 | 10-mer | LRLHSSSGSS | 459-468 | 77 | 378 |
| 436-469 | 10-mer | RLHSSSGSSL | 460-469 | 78 | 379 |
| 509-530 | 8-mer | QLDGLRPD | 509-516 | 1 | 380 |
| 509-530 | 8-mer | LDGLRPDA | 510-517 | 2 | 381 |
| 509-530 | 8-mer | DGLRPDAR | 511-518 | 3 | 382 |
| 509-530 | 8-mer | GLRPDARY | 512-519 | 4 | 383 |
| 509-530 | 8-mer | LRPDARYV | 513-520 | 5 | 384 |
| 509-530 | 8-mer | RPDARYVV | 514-521 | 6 | 385 |
| 509-530 | 8-mer | PDARYVVQ | 515-522 | 7 | 386 |
| 509-530 | 8-mer | DARYVVQV | 516-523 | 8 | 387 |
| 509-530 | 8-mer | ARYVVQVR | 517-524 | 9 | 388 |
| 509-530 | 8-mer | RYVVQVRA | 518-525 | 10 | 389 |
| 509-530 | 8-mer | YVVQVRAR | 519-526 | 11 | 390 |

TABLE 1-continued

| Mapped region (aa) | epitope length | epitope | aa seq location | epitope # | SEQ ID NO: |
|---|---|---|---|---|---|
| 509-530 | 8-mer | VVQVRART | 520-527 | 12 | 391 |
| 509-530 | 8-mer | VQVRARTV | 521-528 | 13 | 392 |
| 509-530 | 8-mer | QVRARTVA | 522-529 | 14 | 393 |
| 509-530 | 8-mer | VRARTVAG | 523-530 | 15 | 394 |
| 509-530 | 9-mer | QLDGLRPDA | 509-517 | 16 | 395 |
| 509-530 | 9-mer | LDGLRPDAR | 510-518 | 17 | 396 |
| 509-530 | 9-mer | DGLRPDARY | 511-519 | 18 | 397 |
| 509-530 | 9-mer | GLRPDARYV | 512-520 | 19 | 398 |
| 509-530 | 9-mer | LRPDARYVV | 513-521 | 20 | 399 |
| 509-530 | 9-mer | RPDARYVVQ | 514-522 | 21 | 400 |
| 509-530 | 9-mer | PDARYVVQV | 515-523 | 22 | 401 |
| 509-530 | 9-mer | DARYVVQVR | 516-524 | 23 | 402 |
| 509-530 | 9-mer | ARYVVQVRA | 517-525 | 24 | 403 |
| 509-530 | 9-mer | RYVVQVRAR | 518-526 | 25 | 404 |
| 509-530 | 9-mer | YVVQVRART | 519-527 | 26 | 405 |
| 509-530 | 9-mer | VVQVRARTV | 520-528 | 27 | 406 |
| 509-530 | 9-mer | VQVRARTVA | 521-529 | 28 | 407 |
| 509-530 | 9-mer | QVRARTVAG | 522-530 | 29 | 408 |
| 509-530 | 10-mer | QLDGLRPDAR | 509-518 | 30 | 409 |
| 509-530 | 10-mer | LDGLRPDARY | 510-519 | 31 | 410 |
| 509-530 | 10-mer | DGLRPDARYV | 511-520 | 32 | 411 |
| 509-530 | 10-mer | GLRPDARYVV | 512-521 | 33 | 412 |
| 509-530 | 10-mer | LRPDARYVVQ | 513-522 | 34 | 413 |
| 509-530 | 10-mer | RPDARYVVQV | 514-523 | 35 | 414 |
| 509-530 | 10-mer | PDARYVVQVR | 515-524 | 36 | 415 |
| 509-530 | 10-mer | DARYVVQVRA | 516-525 | 37 | 416 |
| 509-530 | 10-mer | ARYVVQVRAR | 517-526 | 38 | 417 |
| 509-530 | 10-mer | RYVVQVRART | 518-527 | 39 | 418 |
| 509-530 | 10-mer | YVVQVRARTV | 519-528 | 40 | 419 |
| 509-530 | 10-mer | VVQVRARTVA | 520-529 | 41 | 420 |
| 509-530 | 10-mer | VQVRARTVAG | 521-530 | 42 | 421 |

Polyclonal Antibodies

Polyclonal antibodies are preferably raised in animals by multiple subcutaneous (sc) or intraperitoneal (ip) injections of the relevant antigen and an adjuvant. An improved antibody response may be obtained by conjugating the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride or other agents known in the art.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to {fraction (1/10)} the original amount of peptide or conjugate in Freund's complete adjuvant by subcutaneous injection at multiple sites. At 7-14 days post-booster injection, the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Monoclonal antibodies may be made using the hybridoma method first described by Kohler et al., Nature, 256:495 (1975), or may be made by recombinant DNA methods.

In the hybridoma method, a mouse or other appropriate host animal, such as a hamster or macaque monkey, is immunized as herein described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (Kozbor, J. Immunol., 133: 3001 (1984); Brodeur et al., Monoclonal Antibody Production Techniques and Applications, pp. 51-63 (Marcel Dekker, Inc., New York, 1987)). Exemplary murine myeloma lines include those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by Scatchard analysis (Munson et al., Anal. Biochem., 107:220 (1980)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies may be isolated and sequenced from the hybridoma cells using conventional procedures (e.g., by using oligonucleotide probes that are capable of binding specifically to genes encoding the heavy and light chains of the monoclonal antibodies). Sequence determination will generally require isolation of at least a portion of the gene or cDNA of interest. Usually this requires cloning the DNA or, preferably, mRNA (i.e., cDNA) encoding the monoclonal antibodies. Cloning is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+ mRNA, preferably membrane-associated mRNA, and the library screened using probes specific for human immunoglobulin polypeptide gene sequences. In a preferred embodiment, however, the polymerase chain reaction (PCR) is used to amplify cDNAs (or portions of full-length cDNAs) encoding an immunoglobulin gene segment of interest (e.g., a light chain variable segment). The amplified sequences can be readily cloned into any suitable vector, e.g., expression vectors, minigene vectors, or phage display vectors. It will be appreciated that the particular method of cloning used not critical, so long as it is possible to determine the sequence of some portion of the immunoglobulin polypeptide of interest. As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined, is considered isolated. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

One source for RNA used for cloning and sequencing is a hybridoma produced by obtaining a B cell from the transgenic mouse and fusing the B cell to an immortal cell. An advantage of using hybridomas is that they can be easily screened, and a hybridoma that produces a human monoclonal antibody of interest selected. Alternatively, RNA can be isolated from B cells (or whole spleen) of the immunized animal. When sources other than hybridomas are used, it may be desirable to screen for sequences encoding immunoglobulins or immunoglobulin polypeptides with specific binding characteristics. One method for such screening is the use of phage display technology. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference. In one embodiment using phage display technology, cDNA from an immunized transgenic mouse (e.g., total spleen cDNA) is isolated, the polymerase chain reaction is used to amplify a cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics, are identified by standard techniques such as panning.

The sequence of the amplified or cloned nucleic acid is then determined. Typically the sequence encoding an entire variable region of the immunoglobulin polypeptide is determined, however, it will sometimes by adequate to sequence only a portion of a variable region, for example, the CDR-encoding portion. Typically the portion sequenced will be at least 30 bases in length, more often based coding for at least about one-third or at least about one-half of the length of the variable region will be sequenced.

Sequencing can be carried out on clones isolated from a cDNA library, or, when PCR is used, after subcloning the amplified sequence or by direct PCR sequencing of the amplified segment. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Antibody Fragments

As noted above, antibody fragments comprise a portion of an intact full length antibody, preferably an antigen binding or variable region of the intact antibody, and include linear antibodies and multi specific antibodies formed from antibody fragments. Nonlimiting examples of antibody fragments include Fab, Fab', F(ab')2, Fv, Fd, domain antibody (dAb), complementarity determining region (CDR) fragments, single-chain antibodies (scFv), single chain antibody fragments, diabodies, triabodies, tetrabodies, minibodies, linear antibodies, chelating recombinant antibodies, tribodies or bibodies, intrabodies, nanobodies, small modular immunopharmaceuticals (SMIPs), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen binding to the polypeptide, such as a CDR sequence, as long as the antibody retains the desired biological activity. Such antigen fragments may be produced by the modification of whole antibodies or synthesized de novo using recombinant DNA technologies or peptide synthesis.

The term "diabodies" refers to small antibody fragments with two antigen-binding sites, which fragments comprise a heavy-chain variable domain (VH) connected to a light-chain variable domain (VL) in the same polypeptide chain (VH VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and 30 Hollinger et al., Proc. Natl. Acad. Sci. USA, 90:6444-6448 (1993).

"Single-chain Fv" or "scFv" antibody fragments comprise the $V_H$ and $V_L$ domains of antibody, wherein these domains are present in a single polypeptide chain, and optionally comprising a polypeptide linker between the $V_H$ and $V_L$ domains that enables the Fv to form the desired structure for antigen binding (Bird et al., *Science* 242:423-426, 1988, and Huston et al., *Proc. Natl. Acad. Sci. USA* 85:5879-5883, 1988). An Fd fragment consists of the $V_H$ and $C_H1$ domains.

Additional antibody fragment include a domain antibody (dAb) fragment (Ward et al., *Nature* 341:544-546, 1989) which consists of a $V_H$ domain.

"Linear antibodies" comprise a pair of tandem Fd segments ($V_H$-$C_H$1-$V_H$-$C_H$1) which form a pair of antigen binding regions. Linear antibodies can be bispecific or monospecific (Zapata et al. Protein Eng. 8:1057-62 (1995)).

A "minibody" consisting of scFv fused to CH3 via a peptide linker (hingeless) or via an IgG hinge has been described in Olafsen, et al., Protein Eng Des Sel. 2004 April; 17(4):315-23.

Functional heavy-chain antibodies devoid of light chains are naturally occurring in nurse sharks (Greenberg et al., *Nature* 374:168-73, 1995), wobbegong sharks (Nuttall et al., *Mol Immunol*. 38:313-26, 2001) and *Camelidae* (Hamers-Casterman et al., *Nature* 363: 446-8, 1993; Nguyen et al., *J. Mol. Biol.* 275: 413, 1998), such as camels, dromedaries, alpacas and llamas. The antigen-binding site is reduced to a single domain, the $VH_H$ domain, in these animals. These antibodies form antigen-binding regions using only heavy chain variable region, i.e., these functional antibodies are homodimers of heavy chains only having the structure $H_2L_2$ (referred to as "heavy-chain antibodies" or "HCAbs"). Camelized $V_{HH}$ reportedly recombines with IgG2 and IgG3 constant regions that contain hinge, CH2, and CH3 domains and lack a CH1 domain (Hamers-Casterman et al., supra). For example, llama IgG1 is a conventional ($H_2L_2$) antibody isotype in which $V_H$ recombines with a constant region that contains hinge, CH1, CH2 and CH3 domains, whereas the llama IgG2 and IgG3 are heavy chain-only isotypes that lack CH1 domains and that contain no light chains. Classical $V_H$-only fragments are difficult to produce in soluble form, but improvements in solubility and specific binding can be obtained when framework residues are altered to be more $VH_H$-like. (See, e.g., Reichman, et al., J Immunol Methods 1999, 231:25-38.) Camelized $V_{HH}$ domains have been found to bind to antigen with high affinity (Desmyter et al., *J. Biol. Chem.* 276:26285-90, 2001) and possess high stability in solution (Ewert et al., *Biochemistry* 41:3628-36, 2002). Methods for generating antibodies having camelized heavy chains are described in, for example, in U.S. Patent Publication Nos. 20050136049 and 20050037421.

Because the variable domain of the heavy-chain antibodies is the smallest fully functional antigen-binding fragment with a molecular mass of only 15 kDa, this entity is referred to as a nanobody (Cortez-Retamozo et al., *Cancer Research* 64:2853-57, 2004). A nanobody library may be generated from an immunized dromedary as described in Conrath et al., (*Antimicrob Agents Chemother* 45: 2807-12, 2001) or using recombinant methods as described in Intrabodies are single chain antibodies which demonstrate intracellular expression and can manipulate intracellular protein function (Biocca, et al., *EMBO J.* 9:101-108, 1990; Colby et al., *Proc Natl Acad Sci USA*. 101:17616-21, 2004). Intrabodies, which comprise cell signal sequences which retain the antibody construct in intracellular regions, may be produced as described in Mhashilkar et al (*EMBO J* 14:1542-51, 1995) and Wheeler et al. (*FASEB J.* 17:1733-5. 2003). Transbodies are cell-permeable antibodies in which a protein transduction domains (PTD) is fused with single chain variable fragment (scFv) antibodies Heng et al., (*Med Hypotheses*. 64:1105-8, 2005).

Further contemplated are antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

Multivalent Antibodies

In some embodiments, it may be desirable to generate multivalent or even a multispecific (e.g. bispecific, trispecific, etc.) monoclonal antibody. Such antibody may have binding specificities for at least two different epitopes of the target antigen, or alternatively it may bind to two different molecules, e.g. to the target antigen and to a cell surface protein or receptor. For example, a bispecific antibody may include an arm that binds to the target and another arm that binds to a triggering molecule on a leukocyte such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the target-expressing cell. As another example, bispecific antibodies may be used to localize cytotoxic agents to cells which express target antigen. These antibodies possess a target-binding arm and an arm which binds the cytotoxic agent (e.g., saporin, anti-interferon-60, vinca alkaloid, ricin A chain, methotrexate or radioactive isotope hapten). Multispecific antibodies can be prepared as full length antibodies or antibody fragments.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

According to another approach for making bispecific antibodies, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO96/27011 published Sep. 6, 1996.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. Better et al., Science 240: 1041-1043 (1988) disclose secretion of functional antibody fragments from bacteria (see, e.g., Better et al., Skerra et al. Science 240: 1038-1041 (1988)). For example, Fab'-SH fragments can be directly recovered from *E. coli* and chemically coupled to form bispecific antibodies (Carter et al., Bio/Technology 10:163-167 (1992); Shalaby et al., J. Exp. Med. 175:217-225 (1992)).

Shalaby et al., J. Exp. Med. 175:217-225 (1992) describe the production of a fully humanized bispecific antibody F(ab')$_2$ molecule. Each Fab' fragment was separately secreted from *E. coli* and subjected to directed chemical coupling in vitro to form the bispecfic antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers, e.g. GCN4. (See generally Kostelny et al., J. Immunol. 148(5):1547-1553 (1992).) The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

The term "diabodies" refers to small antibody fragments with two antigen-binding sites, which fragments comprise a heavy-chain variable domain (VH) connected to a light-chain variable domain (VL) in the same polypeptide chain (VH VL). By using a linker that is too short to allow pairing between the two domains on the same chain, the domains are forced to pair with the complementary domains of another chain and create two antigen-binding sites. See, for example, Hollinger et al., Proc. Natl. Acad. Sci. USA, 90:6444-6448 (1993).

Another strategy for making bispecific antibody fragments by the use of single-chain Fv (sFv) dimers has also been reported. See Gruber et al., J. Immunol. 152: 5368 (1994).

Alternatively, the bispecific antibody may be a "linear antibody" produced as described in Zapata et al. Protein Eng. 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

Antibodies with more than two valencies are also contemplated. For example, trispecific antibodies can be prepared. (Tutt et al., J. Immunol. 147:60 (1991)).

A "chelating recombinant antibody" is a bispecific antibody that recognizes adjacent and non-overlapping epitopes of the target antigen, and is flexible enough to bind to both epitopes simultaneously (Neri et al., *J Mol Biol.* 246:367-73, 1995).

Production of bispecific Fab-scFv ("bibody") and trispecific Fab-(scFv)(2) ("tribody") are described in Schoonjans et al. (*J Immunol.* 165:7050-57, 2000) and Willems et al. (*J Chromatogr B Analyt Technol Biomed Life Sci.* 786:161-76, 2003). For bibodies or tribodies, a scFv molecule is fused to one or both of the VL-CL (L) and VH-CH$_1$ (Fd) chains, e.g., to produce a tribody two scFvs are fused to C-term of Fab while in a bibody one scFv is fused to C-term of Fab.

Recombinant Production of Antibodies

Antibodies may be produced by recombinant DNA methodology using one of the antibody expression systems well known in the art (See, e.g., Harlow and Lane, Antibodies: A Laboratory Manual, Cold Spring Harbor Laboratory (1988)).

DNA encoding antibodies of the invention may be placed into expression vectors, which are then transfected into host cells such as *E. coli* cells, simian COS cells, human embryonic kidney 293 cells (e.g., 293E cells), Chinese hamster ovary (CHO) cells, or myeloma cells that do not otherwise produce immunoglobulin protein, to obtain the synthesis of monoclonal antibodies in the recombinant host cells. Recombinant production of antibodies is well known in the art. Antibody fragments have been derived via proteolytic digestion of intact antibodies (see, e.g., Morimoto et al., Journal of Biochemical and Biophysical Methods 24:107-117 (1992) and Brennan et al., Science 229:81 (1985)). However, these fragments can now be produced directly by recombinant host cells. Other techniques for the production of antibody fragments, including peptide synthesis and covalent linkage, will be apparent to the skilled practitioner.

Expression control sequences refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

In an alternative embodiment, the amino acid sequence of an immunoglobulin of interest may be determined by direct protein sequencing. Suitable encoding nucleotide sequences can be designed according to a universal codon table.

Amino acid sequence muteins of the desired antibody may be prepared by introducing appropriate nucleotide changes into the encoding DNA, or by peptide synthesis. Such muteins include, for example, deletions from, and/or insertions into and/or substitutions of, residues within the amino acid sequences of the antibodies. Any combination of deletion, insertion, and substitution is made to arrive at the final construct, provided that the final construct possesses the desired characteristics. The amino acid changes also may alter post-translational processes of the monoclonal, human, humanized, Human Engineered™ or mutein antibody, such as changing the number or position of glycosylation sites.

Nucleic acid molecules encoding amino acid sequence muteins of the antibody are prepared by a variety of methods known in the art. These methods include, but are not limited to, isolation from a natural source (in the case of naturally occurring amino acid sequence muteins) or preparation by oligonucleotide-mediated (or site-directed) mutagenesis, PCR mutagenesis, and cassette mutagenesis of an earlier prepared mutein or a non-mutein version of the antibody.

The invention also provides isolated nucleic acid encoding antibodies of the invention, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium.

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more selective marker genes, an enhancer element, a promoter, and a transcription termination sequence.

(1) Signal Sequence Component

The antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The signal sequence selected preferably is one that is recognized and processed (i.e., cleaved by a signal peptidase) by the host cell. If prokaryotic host cells do not recognize and process the native antibody signal sequence, the signal sequence may be substituted by a signal sequence selected, for example, from the group of the pectate lyase (e.g., pelB) alkaline phosphatase, penicillinase, lpp, or heat-stable enterotoxin II leaders. For yeast secretion the native signal sequence may be substituted by, e.g., the yeast invertase leader, a factor leader (including Saccharomyces and Kluyveromyces α-factor leaders), or acid phosphatase leader, the C. albicans glucoamylase leader, or the signal described in WO90/13646. In mammalian cell expression, mammalian signal sequences as well as viral secretory leaders, for example, the herpes simplex gD signal, are available.

The DNA for such precursor region is ligated in reading frame to DNA encoding the antibody.

(2) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2µ plasmid origin is suitable for yeast, and various viral origins are useful for cloning vectors in mammalian cells. Generally, the origin of replication component is not needed for mammalian expression vectors (the SV40 origin may typically be used only because it contains the early promoter).

(3) Selective Marker Component Expression and cloning vectors may contain a selective gene, also termed a selectable marker. Typical selection genes encode proteins that (a) confer resistance to antibiotics or other toxins, e.g., ampicillin, neomycin, methotrexate, tetracycline, G418, geneticin, histidinol, or mycophenolic acid (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs methotrexate, neomycin, histidinol, puromycin, mycophenolic acid and hygromycin.

Another example of suitable selectable markers for mammalian cells are those that enable the identification of cells competent to take up the antibody-encoding nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding antibody of the invention, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp 1 gene present in the yeast plasmid YRp7 (Stinchcomb et al., Nature, 282: 39 (1979)). The trp1 gene provides a selection marker for a mutant strain of yeast lacking the ability to grow in tryptophan, for example, ATCC No. 44076 or PEP4-1. Jones, Genetics, 85: 12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene. Ura3-deficient yeast strains are complemented by plasmids bearing the ura3 gene.

In addition, vectors derived from the 1.6 µm circular plasmid pKD1 can be used for transformation of Kluyveromyces yeasts. Alternatively, an expression system for large-scale production of recombinant calf chymosin was reported for K. lactis. Van den Berg, Bio/Technology, 8: 135 (1990). Stable multi-copy expression vectors for secretion of mature recombinant human serum albumin by industrial strains of Kluyveromyces have also been disclosed. Fleer et al, Bio/Technology, 9: 968-975 (1991).

(4) Promoter Component

Expression and cloning vectors usually contain a promoter that is recognized by the host organism and is operably linked to the antibody-encoding nucleic acid. Promoters suitable for use with prokaryotic hosts include the arabinose (e.g., araB) promoter phoA promoter, β-lactamaseand lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibody of the invention.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as Abelson leukemia virus, polyoma virus, fowlpox virus, adenovirus (such as Adenovirus 2), bovine papilloma virus, avian sarcoma virus, most preferably cytomegalovirus, a retrovirus, hepatitis-B virus, Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297: 598-601 (1982) on expression of human β-interferon cDNA in mouse cells under the control of a thymidine kinase promoter from herpes simplex virus. Alternatively, the rous sarcoma virus long terminal repeat can be used as the promoter.

(5) Enhancer Element Component

Transcription of a DNA encoding the antibody of this invention by higher eukaryotes is often increased by inserting an enhancer sequence into the vector. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297: 17-18 (1982) on enhancing elements for activation of eukaryotic promoters. The enhancer may be spliced into the vector at a position 5' or 3' to the antibody-encoding sequence, but is preferably located at a site 5' from the promoter.

(6) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein. Another is the mouse immunoglobulin light chain transcription terminator.

(7) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastors* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, tobacco, lemna, and other plant cells can also be utilized as hosts.

However, interest has been greatest in vertebrate cells, and propagation of vertebrate cells in culture (tissue culture) has become routine procedure. Examples of useful mammalian host cell lines are Chinese hamster ovary cells, including CHOK1 cells (ATCC CCL61), DXB-11, DG-44, and Chinese hamster ovary cells/–DHFR(CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, [Graham et al., *J. Gen Virol.* 36: 59 (1977)]; baby hamster kidney cells (BHK, ATCC CCL 10); mouse sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383: 44-68 (1982)); MRC 5 cells; FS4 cells; and a human hepatoma line (Hep G2).

Host cells are transformed or transfected with the above-described expression or cloning vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies.

(8) Culturing the Host Cells

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(9) Purification of Antibody

When using recombinant techniques, the antibody can be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration. Better et al. Science 240: 1041-1043 (1988); ICSU Short Reports 10: 105 (1990); and Proc. Natl. Acad. Sci. USA 90: 457-461 (1993) describe a procedure for isolating antibodies which are secreted to the periplasmic space of *E. coli*. (See also, [Carter et al., *Bio/Technology* 10: 163-167 (1992)].

The antibody composition prepared from microbial or mammalian cells can be purified using, for example, hydroxylapatite chromatography cation or avian exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62: 1-13 (1983)). Protein G is recommended for all mouse isotypes and for human γ3 (Guss et al., EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H 3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Chimeric Antibodies

A rodent antibody on repeated in vivo administration in man either alone or as a conjugate will bring about an immune response in the recipient against the rodent antibody; the so-called HAMA response (Human Anti Mouse Antibody). The HAMA response may limit the effectiveness of the pharmaceutical if repeated dosing is required. The immunogenicity of the antibody may be reduced by chemical modification of the antibody with a hydrophilic polymer such as polyethylene glycol or by using genetic engineering methods to make the antibody structure more human like, e.g. chimeric, humanized, human or Human Engineered™ antibodies. Because such engineered antibodies are less immunogenic in humans than the parental mouse monoclonal antibodies, they can be used for the treatment of humans with far less risk of anaphylaxis. Thus, these antibodies may be preferred in therapeutic applications that involve in vivo administration to a human.

Chimeric monoclonal antibodies, in which the variable Ig domains of a mouse monoclonal antibody are fused to human constant Ig domains, can be generated using standard procedures known in the art (See Morrison, S. L., et al. (1984) Chimeric Human Antibody Molecules; Mouse Antigen Binding Domains with Human Constant Region Domains, Proc. Natl. Acad. Sci. USA 81, 6841-6855; and, Boulianne, G. L., et al, Nature 312, 643-646. (1984)). For example, the gene sequences for the variable domains of the rodent antibody which bind CEA can be substituted for the variable domains of a human myeloma protein, thus producing a recombinant chimeric antibody. These procedures are detailed in EP 194276, EP 0120694, EP 0125023, EP 0171496, EP 0173494 and WO 86/01533. Although some chimeric monoclonal antibodies have proved less immunogenic in humans, the mouse variable Ig domains can still lead to a significant human anti-mouse response.

Humanized Antibodies

Humanized antibodies may be achieved by a variety of methods including, for example: (1) grafting the non-human complementarity determining regions (CDRs) onto a human framework and constant region (a process referred to in the art as humanizing through "CDR grafting"), or, alternatively, (2) transplanting the entire non-human variable domains, but "cloaking" them with a human-like surface by replacement of surface residues (a process referred to in the art as "veneering"). In the present invention, humanized antibodies will include both "humanized" and "veneered" antibodies. These methods are disclosed in, e.g., Jones et al., Nature 321:522 525 (1986); Morrison et al., Proc. Natl. Acad. Sci., U.S.A., 81:6851 6855 (1984); Morrison and Oi, Adv. Immunol., 44:65 92 (1988); Verhoeyer et al., Science 239:1534 1536 (1988); Padlan, Molec. Immun. 28:489 498 (1991); Padlan, Molec. Immunol. 31(3):169 217 (1994); and Kettleborough, C. A. et al., Protein Eng. 4(7):773 83 (1991) each of which is incorporated herein by reference.

For example, the gene sequences of the CDRs of the rodent antibody may be isolated or synthesized and substituted for the corresponding sequence regions of a homologous human antibody gene, producing a human antibody with the specificity of the original rodent antibody. These procedures are described in EP 023940, WO 90/07861 and WO91/09967.

CDR grafting involves introducing one or more of the six CDRs from the mouse heavy and light chain variable Ig domains into the appropriate four framework regions of human variable Ig domains is also called CDR grafting. This technique (Riechmann, L., et al., Nature 332, 323 (1988)), utilizes the conserved framework regions (FR1-FR4) as a scaffold to support the CDR loops which are the primary contacts with antigen. A disadvantage of CDR grafting, however, is that it can result in a humanized antibody that has a substantially lower binding affinity than the original mouse antibody, because amino acids of the framework regions can contribute to antigen binding, and because amino acids of the CDR loops can influence the association of the two variable Ig domains. To maintain the affinity of the humanized monoclonal antibody, the CDR grafting technique can be improved by choosing human framework regions that most closely resemble the framework regions of the original mouse antibody, and by site-directed mutagenesis of single amino acids within the framework or CDRs aided by computer modeling of the antigen binding site (e.g., Co, M. S., et al. (1994), J. Immunol. 152, 2968-2976).

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors (See, e.g., U.S. Pat. Nos. 5,530,101 and 5,585,089 which patents are incorporated herein by reference).

A number of humanizations of mouse monoclonal antibodies by rational design have been reported (See, for example, 20020091240 published Jul. 11, 2002, WO 92/11018 and U.S. Pat. Nos., 5,693,762, 5,766,866.

Human Engineered™ Antibodies

The phrase "Human Engineered™ antibody" refers to an antibody derived from a non-human antibody, typically a mouse monoclonal antibody. Alternatively, a Human Engineered™ antibody may be derived from a chimeric antibody that retains or substantially retains the antigen binding properties of the parental, non-human, antibody but which exhibits diminished immunogenicity as compared to the parental antibody when administered to humans.

Human Engineering™ of antibody variable domains has been described by Studnicka [See, e.g., Studnicka et al. U.S. Pat. No. 5,766,886; Studnicka et al. Protein Engineering 7: 805-814 (1994)] as a method for reducing immunogenicity while maintaining binding activity of antibody molecules. According to the method, each variable region amino acid has been assigned a risk of substitution. Amino acid substitutions are distinguished by one of three risk categories: (1) low risk changes are those that have the greatest potential for reducing immunogenicity with the least chance of disrupting antigen binding; (2) moderate risk changes are those that would further reduce immunogenicity, but have a greater chance of affecting antigen binding or protein folding; (3) high risk residues are those that are important for binding or for maintaining antibody structure and carry the highest risk that antigen binding or protein folding will be affected. Due to the three-dimensional structural role of prolines, modifications at prolines are generally considered to be at least moderate risk changes, even if the position is typically a low risk position.

Variable regions of the light and heavy chains of a rodent antibody are Human Engineered™ as follows to substitute human amino acids at positions determined to be unlikely to adversely effect either antigen binding or protein folding, but likely to reduce immunogenicity in a human environment. Amino acid residues that are at "low risk" positions and that are candidates for modification according to the method are identified by aligning the amino acid sequences of the rodent variable regions with a human variable region sequence. Any human variable region can be used, including an individual VH or VL sequence or a human consensus VH or VL sequence or an individual or consensus human germline sequence. The amino acid residues at any number of the low risk positions, or at all of the low risk positions, can be changed. For example, at each low risk position where the aligned murine and human amino acid residues differ, an amino acid modification is introduced that replaces the rodent residue with the human residue. Alternatively, the amino acid residues at all of the low risk positions and at any number of the moderate risk positions can be changed. Ideally, to achieve the least immunogenicity all of the low and moderate risk positions are changed from rodent to human sequence.

Synthetic genes containing modified heavy and/or light chain variable regions are constructed and linked to human γ heavy chain and/or kappa light chain constant regions. Any human heavy chain and light chain constant regions may be used in combination with the Human Engineered™ antibody variable regions, including IgA (of any subclass, such as IgA1 or IgA2), IgD, IgE, IgG (of any subclass, such as IgG1, IgG2, IgG3, or IgG4), or IgM. The human heavy and light chain genes are introduced into host cells, such as mammalian cells, and the resultant recombinant immunoglobulin products are obtained and characterized.

Human Antibodies from Transgenic Animals

Human antibodies to target antigen can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions.

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL 6, IL 8, TNFa, human CD4, L selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. patent application no. 20030194404; and U.S. patent application no. 20030031667). See also Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. No. 5,591,669, U.S. Pat. No. 5,589,369, U.S. Pat. No. 5,545,807; and U.S. Patent Application No. 20020199213, WO 96/34096 and U.S. patent application no. 20030194404; and U.S. patent application no. 20030031667.

Additional transgenic animals useful to make monoclonal antibodies include the Medarex HuMAb-MOUSE®, described in U.S. Pat. No. 5,770,429 and Fishwild, et al. (Nat. Biotechnol. 14:845-851, 1996), which contains gene sequences from unrearranged human antibody genes that code for the heavy and light chains of human antibodies. Immunization of a HuMAb-MOUSE® enables the production of monoclonal antibodies to the target protein.

Also, Ishida et al. (Cloning Stem Cells. 4:91-102, 2002) describes the TransChromo Mouse (TCMOUSE™) which comprises megabase-sized segments of human DNA and which incorporates the entire human immunoglobulin (hIg) loci. The TCMOUSE has a fully diverse repertoire of hIgs, including all the subclasses of IgGs (IgG1-G4). Immunization of the TC Mouse with various human antigens produces antibody responses comprising human antibodies.

U.S. Patent Application No. 20030092125 describes methods for biasing the immune response of an animal to the desired epitope. Human antibodies may also be generated by in vitro activated B cells (see U.S. Pat. Nos. 5,567,610 and 5,229,275).

Antibodies from Phage Display Technology

The development of technologies for making repertoires of recombinant human antibody genes, and the display of the encoded antibody fragments on the surface of filamentous bacteriophage, has provided a recombinant means for directly making and selecting human antibodies, which also can be applied to humanized, chimeric, murine or mutein antibodies. The antibodies produced by phage technology are produced as antigen binding fragments-usually Fv or Fab fragments-in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

Typically, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. By several rounds of antigen binding and re-amplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., J. Mol. Biol., 227:381 (1991); Marks et al., J. Mol. Biol, 222:581-597 (1991); U.S. Pat. Nos. 5,565,332 and 5,573,905; Clackson, T., and Wells, J. A., TIBTECH 12, 173-184 (1994)). In particular, in vitro selection and evolution of antibodies derived from phage display libraries has become a powerful tool (See Burton, D. R., and Barbas III, C. F., Adv. Immunol. 57, 191-280 (1994); and, Winter, G., et al., Annu. Rev. Immunol. 12, 433-455 (1994); U.S. patent application no. 20020004215 and WO92/01047; U.S. patent application no. 20030190317 published Oct. 9, 2003 and U.S. Pat. No. 6,054,287; U.S. Pat. No. 5,877,293.

Watkins, "Screening of Phage-Expressed Antibody Libraries by Capture Lift," Methods in Molecular Biology, Antibody Phage Display: Methods and Protocols 178: 187-193, and U.S. patent application no. 200120030044772 published Mar. 6, 2003 describe methods for screening phage-expressed antibody libraries or other binding molecules by capture lift, a method involving immobilization of the candidate binding molecules on a solid support.

The antibody products may be screened for activity and for suitability in the treatment methods of the invention using assays as described in the section entitled "Screening Methods" herein or using any suitable assays known in the art.

Amino Acid Sequence Muteins

Antibodies of the invention include muteins of a parent antibody wherein the polypeptide sequence of the parent antibody has been altered by at least one amino acid substitution, deletion, or insertion in the variable region or the portion equivalent to the variable region, including within the CDRs, provided that the mutein retains the desired binding affinity or biological activity. Muteins may be substantially homologous or substantially identical to the parent antibody, e.g. at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical or homologous. Identity or homology with respect to this sequence is defined herein as the percentage of amino acid residues in the candidate sequence that are identical with the parent sequence, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology. Thus, sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences, or along a pre-determined portion of one or both sequences). The programs provide a default opening penalty and a default gap penalty, and a scoring matrix such as PAM 250 [a standard scoring matrix; see Dayhoff et al., in *Atlas of Protein Sequence and Structure*, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences.

Antibodies of the invention may also include alterations in the polypeptide sequence of the constant region, which will not affect binding affinity but may alter effector function, such as antibody-dependent cellular toxicity (ADCC), complement dependent cytotoxicity (CDC) or clearance and uptake (and resultant effect on half-life).

Insertions

Amino acid sequence insertions include amino- and/or carboxyl-terminal fusions ranging in length from one residue to polypeptides containing a hundred or more residues, as well as intra-sequence insertions of single or multiple amino acid residues, e.g. 2, 3 or more. Examples of terminal insertions include an antibody with an N-terminal methionyl residue or the antibody (including antibody fragment) fused to an epitope tag or a salvage receptor epitope. Other insertional muteins of the antibody molecule include the addition of glycosylation sites, addition of cysteines for intramolecular or intermolecular bonding, or fusion to a polypeptide which increases the serum half-life of the antibody, e.g. at the N-terminus or C-terminus. For example, cysteine bond(s) may be added to the antibody to improve its stability (particularly where the antibody is an antibody fragment such as an Fv fragment).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to an antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to an antibody by inserting or substituting one or more serine or threonine residues to the sequence of the original antibody.

The term "epitope tagged" refers to the antibody fused to an epitope tag. The epitope tag polypeptide has enough residues to provide an epitope against which an antibody there against can be made, yet is short enough such that it does not interfere with activity of the antibody. The epitope tag preferably is sufficiently unique so that the antibody there against does not substantially cross-react with other epitopes. Suitable tag polypeptides generally have at least 6 amino acid residues and usually between about 8-50 amino acid residues (preferably between about 9-30 residues). Examples include the flu HA tag polypeptide and its antibody 12CA5 [Field et al., *Mol. Cell. Biol.* 8: 2159-2165 (1988)]; the c-myc tag and the 8F9, 3C7, 6E10, G4, B7 and 9E10 antibodies thereto [Evan et al., *Mol. Cell. Biol.* 5(12): 3610-3616 (1985)]; and the Herpes Simplex virus glycoprotein D (gD) tag and its antibody [Paborsky et al., *Protein Engineering* 3(6): 547-553 (1990)]. Other exemplary tags are a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention.

As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Deletions

Amino acid sequence deletions include amino- and/or carboxyl-terminal deletions ranging in length from one to a hundred or more residues, resulting in fragments that retain binding affinity for target antigen, as well as intra-sequence deletions of single or multiple amino acid residues, e.g. 2, 3 or more. For example, glycosylation sites may be deleted or moved to a different position by deleting part or all of the tripeptide or other recognition sequences for glycosylation.

Substitutions

Another type of mutein is an amino acid substitution mutein. These muteins have at least one amino acid residue in the antibody molecule removed and a different residue inserted in its place. Substitutional mutagenesis within any of the hypervariable or CDR regions or framework regions is contemplated. Conservative substitutions are shown in Table 2. The most conservative substitution is found under the heading of "preferred substitutions". If such substitutions result in no change in biological activity, then more substantial changes, denominated "exemplary substitutions" in Table 1, or as further described below in reference to amino acid classes, may be introduced and the products screened.

TABLE 2

| Original | Exemplary | Preferred Residue Substitutions |
|---|---|---|
| Ala (A) | val; leu; ile | val |
| Arg (R) | lys; gln; asn | lys |
| Asn (N) | gln; his; asp, lys; gln | arg |
| Asp (D) | glu; asn | glu |
| Cys (C) | ser; ala | ser |
| Gln (Q) | asn; glu | asn |
| Glu (E) | asp; gln | asp |
| Gly (G) | ala | |
| His (H) | asn; gln; lys; arg | |
| Ile (I) | leu; val; met; ala; phe; | leu norleucine |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | |
| Pro (P) | ala | |
| Ser (S) | thr | |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Conservative substitutions involve replacing an amino acid with another member of its class. Non-conservative substitutions involve replacing a member of one of these classes with a member of another class.

Any cysteine residue not involved in maintaining the proper conformation of the antibody also may be substituted, generally with serine, to improve the oxidative stability of the molecule and prevent aberrant crosslinking.

Affinity maturation generally involves preparing and screening antibody muteins that have substitutions within the CDRs of a parent antibody and selecting muteins that have improved biological properties such as binding affinity relative to the parent antibody. A convenient way for generating such substitutional muteins is affinity maturation using phage display. Briefly, several hypervariable region sites (e.g. 6-7 sites) are mutated to generate all possible amino substitutions at each site. The antibody muteins thus generated are displayed in a monovalent fashion from filamentous phage particles as fusions to the gene III product of M13 packaged within each particle. The phage-displayed muteins are then screened for their biological activity (e.g. binding affinity). See e.g., WO 92/01047, WO 93/112366, WO 95/15388 and WO 93/19172.

Current antibody affinity maturation methods belong to two mutagenesis categories: stochastic and nonstochastic. Error prone PCR, mutator bacterial strains (Low et al., *J. Mol. Biol.* 260, 359-68, 1996), and saturation mutagenesis (Nishimiya et al., *J. Biol. Chem.* 275:12813-20, 2000; Chowdhury, P. S. *Methods Mol. Biol.* 178, 269-85, 2002) are typical examples of stochastic mutagenesis methods (Rajpal et al., *Proc Natl Acad Sci USA.* 102:8466-71, 2005). Nonstochastic techniques often use alanine-scanning or site-directed mutagenesis to generate limited collections of specific muteins. Some methods are described in further detail below.

Affinity maturation via panning methods—Affinity maturation of recombinant antibodies is commonly performed through several rounds of panning of candidate antibodies in the presence of decreasing amounts of antigen. Decreasing the amount of antigen per round selects the antibodies with the highest affinity to the antigen thereby yielding antibodies of high affinity from a large pool of starting material. Affinity maturation via panning is well known in the art and is described, for example, in Huls et al. (*Cancer Immunol Immunother.* 50:163-71, 2001). Methods of affinity maturation using phage display technologies are described elsewhere herein and known in the art (see e.g., Daugherty et al., *Proc Natl Acad Sci USA.* 97:2029-34, 2000).

Look-through mutagenesis—Look-through mutagenesis (LTM) (Rajpal et al., *Proc Natl Acad Sci USA.* 102:8466-71, 2005) provides a method for rapidly mapping the antibody-binding site. For LTM, nine amino acids, representative of the major side-chain chemistries provided by the 20 natural amino acids, are selected to dissect the functional side-chain contributions to binding at every position in all six CDRs of an antibody. LTM generates a positional series of single mutations within a CDR where each "wild type" residue is systematically substituted by one of nine selected amino acids. Mutated CDRs are combined to generate combinatorial single-chain variable fragment (scFv) libraries of increasing complexity and size without becoming prohibitive to the quantitative display of all muteins. After positive selection, clones with improved binding are sequenced, and beneficial mutations are mapped.

Error-prone PCR—Error-prone PCR involves the randomization of nucleic acids between different selection rounds. The randomization occurs at a low rate by the intrinsic error rate of the polymerase used but can be enhanced by error-prone PCR (Zaccolo et al., J. Mol. Biol. 285:775-783, 1999) using a polymerase having a high intrinsic error rate during transcription (Hawkins et al., J Mol Biol. 226:889-96, 1992). After the mutation cycles, clones with improved affinity for the antigen are selected using routine mehods in the art.

DNA Shuffling—Nucleic acid shuffling is a method for in vitro or in vivo homologous recombination of pools of shorter or smaller polynucleotides to produce variant polynucleotides. DNA shuffling has been described in U.S. Pat. No. 6,605,449, U.S. Pat. No. 6,489,145, WO 02/092780 and Stemmer, *Proc. Natl. Acad. Sci. USA,* 91:10747-51 (1994). Generally, DNA shuffling is comprised of 3 steps: fragmentation of the genes to be shuffled with DNase I, random hybridization of fragments and reassembly or filling in of the fragmented gene by PCR in the presence of DNA polymerase (sexual PCR), and amplification of reassembled product by conventional PCR.

DNA shuffling differs from error-prone PCR in that it is an inverse chain reaction. In error-prone PCR, the number of polymerase start sites and the number of molecules grows exponentially. In contrast, in nucleic acid reassembly or shuffling of random polynucleotides the number of start sites and the number (but not size) of the random polynucleotides decreases over time.

In the case of an antibody, DNA shuffling allows the free combinatorial association of all of the CDR1s with all of the CDR2s with all of the CDR3s, for example. It is contemplated that multiple families of sequences can be shuffled in the same reaction. Further, shuffling generally conserves the relative order, such that, for example, CDR1 will not be found in the position of CDR2. Rare shufflants will contain a large number of the best (e.g. highest affinity) CDRs and these rare shufflants may be selected based on their superior affinity.

The template polynucleotide which may be used in DNA shuffling may be DNA or RNA. It may be of various lengths depending on the size of the gene or shorter or smaller polynucleotide to be recombined or reassembled. Preferably, the template polynucleotide is from 50 bp to 50 kb. The template polynucleotide often should be double-stranded.

It is contemplated that single-stranded or double-stranded nucleic acid polynucleotides having regions of identity to the template polynucleotide and regions of heterology to the template polynucleotide may be added to the template polynucleotide, during the initial step of gene selection. It is also contemplated that two different but related polynucleotide templates can be mixed during the initial step.

Alanine scanning—Alanine scanning mutagenesis can be performed to identify hypervariable region residues that contribute significantly to antigen binding. Cunningham and Wells, (*Science* 244:1081-1085, 1989). A residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other mutationsat, or for, the sites of substitution. Thus, while the site for introducing an amino acid sequence change is predetermined, the nature of the mutation per se need not be predetermined. For example, to analyze the performance of a mutation at a given site, ala scanning or random mutagenesis is conducted at the target codon or region and the expressed antibody muteins are screened for the desired activity.

Computer-aided design—Alternatively, or in addition, it may be beneficial to analyze a crystal structure of the antigen-antibody complex to identify contact points between the antibody and antigen, or to use computer software to model such contact points. Such contact residues and neighboring residues are candidates for substitution according to the techniques elaborated herein. Once such muteins are generated, the panel of muteins is subjected to screening as described herein and antibodies with superior properties in one or more relevant assays may be selected for further development.

Affinity maturation involves preparing and screening antibody muteins that have substitutions within the CDRs of a parent antibody and selecting muteins that have improved biological properties such as binding affinity relative to the parent antibody. A convenient way for generating such substitutional muteins is affinity maturation using phage display. Briefly, several hypervariable region sites (e.g. 6-7 sites) are mutated to generate all possible amino substitutions at each site. The antibody muteins thus generated are displayed in a monovalent fashion from filamentous phage particles as fusions to the gene III product of M13 packaged within each particle. The phage-displayed muteins are then screened for their biological activity (e.g. binding affinity).

Alanine scanning mutagenesis can be performed to identify hypervariable region residues that contribute significantly to antigen binding. Alternatively, or in addition, it may be beneficial to analyze a crystal structure of the antigen-antibody complex to identify contact points between the antibody and antigen. Such contact residues and neighboring residues are candidates for substitution according to the techniques elaborated herein. Once such muteins are generated, the panel of muteins is subjected to screening as described herein and antibodies with superior properties in one or more relevant assays may be selected for further development.

Altered Effector Function

Other modifications of the antibody are contemplated. For example, it may be desirable to modify the antibody of the invention with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148: 2918-2922 (1992). Homodimeric antibodies with enhanced activity may also be prepared using heterobifunctional cross-linkers as described in Wolff et al., Cancer Research 53: 2560-2565 (1993). Alternatively, an antibody can be engineered which has dual Fc regions and may thereby have enhanced complement lysis and ADCC capabilities. See Stevenson et al., *Anti-Cancer Drug Design* 3: 219-230 (1989). In addition, it has been shown that sequences within the CDR can cause an antibody to bind to MHC Class II and trigger an unwanted helper T-cell response. A conservative substitution can allow the antibody to retain binding activity yet lose its ability to trigger an unwanted T-cell response. Also see Steplewski et al., Proc Natl Acad Sci USA. 1988; 85(13): 4852-6, incorporated herein by reference in its entirety, which described chimeric antibodies wherein a murine variable region was joined with human gamma 1, gamma 2, gamma 3, and gamma 4 constant regions.

In certain embodiments of the invention, it may be desirable to use an antibody fragment, rather than an intact antibody, to increase tumor penetration, for example. In this case, it may be desirable to modify the antibody fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, e.g., WO96/32478).

The salvage receptor binding epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the C.sub.L region or V.sub.L region, or both, of the antibody fragment. See also International applications WO 97/34631 and WO 96/32478 which describe Fc variants and their interaction with the salvage receptor.

Thus, antibodies of the invention may comprise a human Fc portion, a human consensus Fc portion, or a mutein thereof that retains the ability to interact with the Fc salvage receptor, including muteins in which cysteines involved in disulfide bonding are modified or removed, and/or in which the a met is added at the N-terminus and/or one or more of the N-terminal 20 amino acids are removed, and/or regions that interact with complement, such as the C1q binding site, are removed, and/or the ADCC site is removed [see, e.g., Molec. Immunol. 29 (5): 633-9 (1992)]. Antibodies of the IgG class may also include a different constant region, e.g. an IgG2 antibody may be modified to display an IgG1 or IgG4 constant region.

In the case of IgG1, modifications to the constant region, particularly the hinge or CH2 region, may increase or decrease effector function, including ADCC and/or CDC activity. In other embodiments, an IgG2 constant region is modified to decrease antibody-antigen aggregate formation. In the case of IgG4, modifications to the constant region, particularly the hinge region, may reduce the formation of half-antibodies. In specific exemplary embodiments, mutating the IgG4 hinge sequence Cys-Pro-Ser-Cys to the IgG1 hinge sequence Cys-Pro-Pro-Cys is provided.

Previous studies mapped the binding site on human and murine IgG for FcR primarily to the lower hinge region composed of IgG residues 233-239. Other studies proposed additional broad segments, e.g. Gly316-Lys338 for human Fc receptor I, Lys274-Arg301 and Tyr407-Arg416 for human Fc receptor III, or found a few specific residues outside the lower hinge, e.g. Asn297 and Glu318 for murine IgG2b interacting with murine Fc receptor II. The report of the 3.2-Å crystal structure of the human IgG1 Fc fragment with human Fc receptor IIIA delineated IgG1 residues Leu234-Ser239, Asp265-Glu269, Asn297-Thr299, and Ala327-Ile332 as involved in binding to Fc receptor 111A. It has been suggested based on crystal structure that in addition to the lower hinge (Leu234-Gly237), residues in IgG CH2 domain loops FG (residues 326-330) and BC (residues 265-271) might play a role in binding to Fc receptor IIA. See Shields et al., J. Biol. Chem., 276(9):6591-6604 (2001), incorporated by reference herein in its entirety. Mutation of residues within Fc receptor binding sites can result in altered effector function, such as altered ADCC or CDC activity, or altered half-life. As described above, potential mutations include insertion, deletion or substitution of one or more residues, including substitution with alanine, a conservative substitution, a non-conservative substitution, or replacement with a corresponding amino acid residue at the same position from a different IgG subclass (e.g. replacing an IgG1 residue with a corresponding IgG2 residue at that position).

Shields et al. reported that IgG1 residues involved in binding to all human Fc receptors are located in the CH2 domain proximal to the hinge and fall into two categories as follows: 1) positions that may interact directly with all FcR include Leu234-Pro238, Ala327, and Pro329 (and possibly Asp265); 2) positions that influence carbohydrate nature or position include Asp265 and Asn297. The additional IgG1 residues that affected binding to Fc receptor II are as follows: (largest effect) Arg255, Thr256, Glu258, Ser267, Asp270, Glu272, Asp280, Arg292, Ser298, and (less effect) His268, Asn276, His285, Asn286, Lys290, Gln295, Arg301, Thr307, Leu309, Asn315, Lys322, Lys326, Pro331, Ser337, Ala339, Ala378, and Lys414. A327Q, A327S, P329A, D265A and D270A reduced binding. In addition to the residues identified above for all FcR, additional IgG1 residues that reduced binding to Fc receptor IIIA by 40% or more are as follows: Ser239, Ser267 (Gly only), His268, Glu293, Gln295, Tyr296, Arg301, Val303, Lys338, and Asp376. Muteins that improved binding to FcRIIIA include T256A, K290A, S298A, E333A, K334A, and A339T. Lys414 showed a 40% reduction in binding for FcRIIA and FcRIIB, Arg416 a 30% reduction for FcRIIA and FcRIIIA, Gln419 a 30% reduction to FcRIIA and a 40% reduction to FcRIIB, and Lys360 a 23% improvement to FcRIIIA. See also Presta et al., Biochem. Soc. Trans. (2001) 30, 487-490.

For example, U.S. Pat. No. 6,194,551, incorporated herein by reference in its entirety, describes muteins with altered effector function containing mutations in the human IgG Fc region, at amino acid position 329, 331 or 322 (using Kabat numbering), some of which display reduced Clq binding or CDC activity. As another example, U.S. Pat. No. 6,737,056, incorporated herein by reference in its entirety, describes muteins with altered effector or Fc-gamma-receptor binding containing mutations in the human IgG Fc region, at amino acid position 238, 239, 248, 249, 252, 254, 255, 256, 258, 265, 267, 268, 269, 270, 272, 276, 278, 280, 283, 285, 286, 289, 290, 292, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439 (using Kabat numbering), some of which display receptor binding profiles associated with reduced ADCC or CDC activity. Of these, a mutation at amino acid position 238, 265, 269, 270, 327 or 329 are stated to reduce binding to FcRI, a mutation at amino acid position 238, 265, 269, 270, 292, 294, 295, 298, 303, 324, 327, 329, 333, 335, 338, 373, 376, 414, 416, 419, 435, 438 or 439 are stated to reduce binding to FcR11, and a mutation at amino acid position 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 is stated to reduce binding to FcRIII.

U.S. Pat. No. 5,624,821, incorporated by reference herein in its entirety, reports that Clq binding activity of an murine antibody can be altered by mutating amino acid residue 318, 320 or 322 of the heavy chain and that replacing residue 297 (Asn) results in removal of lytic activity.

United States Application Publication No. 20040132101, incorporated by reference herein in its entirety, describes muteins with mutations at amino acid positions 240, 244, 245, 247, 262, 263, 266, 299, 313, 325, 328, or 332 (using Kabat numbering) or positions 234, 235, 239, 240, 241, 243, 244, 245, 247, 262, 263, 264, 265, 266, 267, 269, 296, 297, 298, 299, 313, 325, 327, 328, 329, 330, or 332 (using Kabat numbering), of which mutations at positions 234, 235, 239, 240, 241, 243, 244, 245, 247, 262, 263, 264, 265, 266, 267, 269, 296, 297, 298, 299, 313, 325, 327, 328, 329, 330, or 332 may reduce ADCC activity or reduce binding to an Fc gamma receptor.

Chappel et al., Proc Natl Acad Sci USA. 1991; 88(20): 9036-40, incorporated herein by reference in its entirety, report that cytophilic activity of IgG1 is an intrinsic property of its heavy chain CH2 domain. Single point mutations at any of amino acid residues 234-237 of IgG1 significantly lowered or abolished its activity. Substitution of all of IgG1 residues 234-237 (LLGG) into IgG2 and IgG4 were required to restore full binding activity. An IgG2 antibody containing the entire ELLGGP sequence (residues 233-238) was observed to be more active than wild-type IgG1.

Isaacs et al., J Immunol. 1998; 161(8):3862-9, incorporated herein by reference in its entirety, report that mutations within a motif critical for Fc gammaR binding (glutamate 233 to proline, leucine/phenylalanine 234 to valine, and leucine 235 to alanine) completely prevented depletion of target cells. The mutation glutamate 318 to alanine eliminated effector function of mouse IgG2b and also reduced the potency of human IgG4.

Armour et al., Mol Immunol. 2003; 40(9):585-93, incorporated by reference herein in its entirety, identified IgG1 muteins which react with the activating receptor, FcgammaRIIa, at least 10-fold less efficiently than wildtype IgG1 but whose binding to the inhibitory receptor, FcgammaRIIb, is only four-fold reduced. Mutations were made in the region of amino acids 233-236 and/or at amino acid positions 327, 330 and 331. See also WO 99/58572, incorporated by reference herein in its entirety.

Xu et al., J Biol Chem. 1994; 269(5):3469-74, incorporated by reference herein in its entirety, report that mutating IgG1 Pro331 to Ser markedly decreased C1q binding and virually eliminated lytic activity. In contrast, the substitution of Pro for Ser331 in IgG4 bestowed partial lytic activity (40%) to the IgG4 Pro331 mutein.

Schuurman et al., Mol Immunol. 2001; 38(1):1-8, incorporated by reference herein in its entirety, report that mutating one of the hinge cysteines involved in the inter-heavy chain bond formation, Cys226, to serine resulted in a more stable inter-heavy chain linkage. Mutating the IgG4 hinge sequence Cys-Pro-Ser-Cys to the IgG1 hinge sequence Cys-Pro-Pro-Cys also markedly stabilizes the covalent interaction between the heavy chains.

Angal et al., Mol Immunol. 1993; 30(1):105-8, incorporated by reference herein in its entirety, report that mutating the serine at amino acid position 241 in IgG4 to proline (found at that position in IgG1 and IgG2) led to the production of a homogeneous antibody, as well as extending serum half-life and improving tissue distribution compared to the original chimeric IgG4.

The invention also contemplates production of antibody molecules with altered carbohydrate structure resulting in altered effector activity, including antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity [Yamane-Ohnuki et al., Biotechnol Bioeng. 2004 Sep. 5; 87(5):614-22]. Similar effects can be accomplished through decreasing the activity of this or other enzymes in the fucosylation pathway, e.g., through siRNA or antisense RNA treatment, engineering cell lines to knockout the enzyme(s), or culturing with selective glycosylation inhibitors [Rothman et al., Mol Immunol. 1989 December; 26(12):1113-23]. Some host cell strains, e.g. Lec 13 or rat hybridoma YB2/0 cell line naturally produce antibodies with lower fucosylation levels. Shields et al., J Biol Chem. 2002 Jul. 26; 277(30):26733-40; Shinkawa et al., J Biol Chem. 2003 Jan. 31; 278(5):3466-73. An increase in the level of bisected carbohydrate, e.g. through recombinantly producing antibody in cells that overexpress GnTIII enzyme, has also been determined to increase ADCC activity. Umana et al., Nat Biotechnol. 1999 February; 17(2):176-80. It has been predicted that the absence of only one of the two fucose residues may be sufficient to increase ADCC activity. [Ferrara et al., J Biol Chem. 2005 Dec. 5]

Other Covalent Modifications

Covalent modifications of the antibody are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, .alpha.-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R—N.dbd.C.dbd.N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the .alpha.-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin, et al. Arch. Biochem. Biophys. 259: 52 (1987) and by Edge et al. Anal. Biochem., 118: 131 (1981). Enzymatic cleavage of carbohydrate moieties on antibodies can be achieved by the use of a variety of endo- and exo-glycosidases as described by Thotakura et al. Meth. Enzymol. 138: 350 (1987).

Another type of covalent modification of the antibody comprises linking the antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315 456.

Each antibody molecule may be attached to one or more (i.e. 1, 2, 3, 4, 5 or more) polymer molecules. Polymer molecules are preferably attached to antibodies by linker molecules. The polymer may, in general, be a synthetic or naturally occurring polymer, for example an optionally substituted straight or branched chain polyalkene, polyalkenylene or polyoxyalkylene polymer or a branched or unbranched polysaccharide, e.g. homo- or hetero-polysaccharide. Preferred polymers are polyoxyethylene polyols and polyethylene glycol (PEG). PEG is soluble in water at room temperature and has the general formula: R(O—CH2-CH2)n O—R where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/antibody of the present invention. Preferred polymers, and methods to attach them to peptides, are shown in U.S. Pat. Nos. 4,766,106; 4,179,337; 4,495,285; and 4,609, 546 which are all hereby incorporated by reference in their entireties.

Gene Therapy

Delivery of a therapeutic antibody to appropriate cells can be effected via gene therapy ex vivo, in situ, or in vivo by use of any suitable approach known in the art, including by use of physical DNA transfer methods (e.g., liposomes or chemical treatments) or by use of viral vectors (e.g., adenovirus, adeno-associated virus, or a retrovirus). For example, for in vivo therapy, a nucleic acid encoding the desired antibody, either alone or in conjunction with a vector, liposome, or precipitate may be injected directly into the subject, and in some embodiments, may be injected at the site where the expression of the antibody compound is desired. For ex vivo treatment, the subject's cells are removed, the nucleic acid is introduced into these cells, and the modified cells are returned to the subject either directly or, for example, encapsulated within porous membranes which are implanted into the patient. See, e.g., U.S. Pat. Nos. 4,892,538 and 5,283,187. There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, and calcium phosphate precipitation. A commonly used vector for ex vivo delivery of a nucleic acid is a retrovirus.

Other in vivo nucleic acid transfer techniques include transfection with viral vectors (such as adenovirus, Herpes simplex I virus, or adeno-associated virus) and lipid-based systems. The nucleic acid and transfection agent are optionally associated with a microparticle. Exemplary transfection agents include calcium phosphate or calcium chloride co-precipitation, DEAE-dextran-mediated transfection, quaternary ammonium amphiphile DOTMA ((dioleoyloxypropyl) trimethylammonium bromide, commercialized as Lipofectin by GIBCO-BRL))(Felgner et al, (1987) Proc. Natl. Acad. Sci. USA 84, 7413-7417; Malone et al. (1989) Proc. Natl Acad. Sci. USA 86 6077-6081); lipophilic glutamate diesters with pendent trimethylammonium heads (Ito et al. (1990) Biochem. Biophys. Acta 1023, 124-132); the metabolizable parent lipids such as the cationic lipid dioctadecylamido glycylspermine (DOGS, Transfectam, Promega) and dipalmitoylphosphatidyl ethanolamylspermine (DPPES)(J. P. Behr (1986) Tetrahedron Lett. 27, 5861-5864; J. P. Behr et al. (1989) Proc. Natl. Acad. Sci. USA 86, 6982-6986); metabolizable quaternary ammonium salts (DOTB, N-(1-[2, 3-dioleoyloxy]propyl)-N,N,N-trimethylammonium methylsulfate (DOTAP)(Boehringer Mannheim), polyethyleneimine (PEI), dioleoyl esters, ChoTB, ChoSC, DOSC) (Leventis et al. (1990) Biochim. Inter. 22, 235-241); 3beta[N-(N', N'-dimethylaminoethane)-carbamoyl]cholesterol (DC-Chol), dioleoylphosphatidyl ethanolamine (DOPE)/3beta[N-(N',N'-dimethylaminoethane)-carbamoyl]cholesterolDC-Chol in one to one mixtures (Gao et al., (1991) Biochim. Biophys. Acta 1065, 8-14), spermine, spermidine, lipopolyamines (Behr et al., Bioconjugate Chem, 1994, 5: 382-389), lipophilic polylysines (LPLL) (Zhou et al., (1991) Biochim. Biophys. Acta 939, 8-18), [[(1,1,3,3-tetramethylbutyl)cre-soxy]ethoxy]jethyl]dimethylbe nzylammonium hydroxide (DEBDA hydroxide) with excess phosphatidylcholine/cholesterol (Ballas et al., (1988) Biochim. Biophys. Acta 939, 8-18), cetyltrimethylammonium bromide (CTAB)/ DOPE mixtures (Pinnaduwage et al, (1989) Biochim. Biophys. Acta 985, 33-37), lipophilic diester of glutamic acid (TMAG) with DOPE, CTAB, DEBDA, didodecylammonium bromide (DDAB), and stearylamine in admixture with phosphatidylethanolamine (Rose et al., (1991) Biotechnique 10, 520-525), DDAB/DOPE (TransfectACE, GIBCO BRL), and oligogalactose bearing lipids. Exemplary transfection enhancer agents that increase the efficiency of transfer include, for example, DEAE-dextran, polybrene, lysosome-disruptive peptide (Ohmori N I et al, Biochem Biophys Res Commun Jun. 27, 1997;235(3):726-9), chondroitan-based proteoglycans, sulfated proteoglycans, polyethylenimine, polylysine (Pollard H et al. J Biol Chem, 1998 273 (13):7507-

11), integrin-binding peptide CYGGRGDTP (SEQ ID NO: 429), linear dextran nonasaccharide, glycerol, cholesteryl groups tethered at the 3'-terminal internucleoside link of an oligonucleotide (Letsinger, R. L. 1989 Proc Natl Acad Sci USA 86: (17):6553-6), lysophosphatide, lysophosphatidylcholine, lysophosphatidylethanolamine, and 1-oleoyl lysophosphatidylcholine.

In some situations it may be desirable to deliver the nucleic acid with an agent that directs the nucleic acid-containing vector to target cells. Such "targeting" molecules include antibodies specific for a cell-surface membrane protein on the target cell, or a ligand for a receptor on the target cell. Where liposomes are employed, proteins which bind to a cell-surface membrane protein associated with endocytosis may be used for targeting and/or to facilitate uptake. Examples of such proteins include capsid proteins and fragments thereof tropic for a particular cell type, antibodies for proteins which undergo internalization in cycling, and proteins that target intracellular localization and enhance intracellular half-life. In other embodiments, receptor-mediated endocytosis can be used. Such methods are described, for example, in Wu et al., 1987 or Wagner et al., 1990. For review of the currently known gene marking and gene therapy protocols, see Anderson 1992. See also WO 93/25673 and the references cited therein. For additional reviews of gene therapy technology, see Friedmann, Science, 244: 1275-1281 (1989); Anderson, Nature, supplement to vol. 392, no 6679, pp. 25-30 (1998); Verma, Scientific American: 68-84 (1990); and Miller, Nature, 357: 455-460 (1992).

Screening Methods

Another aspect of the present invention is directed to methods of identifying antibodies which increase activity of a EphB3 comprising contacting a EphB3 with an antibody, and determining whether the antibody modifies activity of the EphB3. The activity in the presence of the test antibody is compared to the activity in the absence of the test antibody. Where the activity of the sample containing the test antibody is higher than the activity in the sample lacking the test antibody, the antibody will have activated or increased the activity. Effective therapeutics depend on identifying efficacious agents devoid of significant toxicity. Antibodies may be screened for binding affinity by methods known in the art. For example, gel-shift assays, Western blots, radiolabeled competition assay, co-fractionation by chromatography, co-precipitation, cross linking, ELISA, and the like may be used, which are described in, for example, Current Protocols in Molecular Biology (1999) John Wiley & Sons, NY, which is incorporated herein by reference in its entirety. In addition, Biacore® may be employed to assess antibody competition (See, e.g., Example 5 below).

To initially screen for antibodies which bind to the desired epitope on the target antigen, a routine cross-blocking assay such as that described in Antibodies, A Laboratory Manual, Cold Spring Harbor Laboratory, Ed Harlow and David Lane (1988), can be performed. Routine competitive binding assays may also be used, in which the unknown antibody is characterized by its ability to inhibit binding of target to a target-specific antibody of the invention. Intact antigen, fragments thereof such as the extracellular domain, or linear epitopes can be used. Epitope mapping is described in Champe et al., J. Biol. Chem. 270: 1388-1394 (1995).

In one variation of an in vitro binding assay, the invention provides a method comprising the steps of (a) contacting an immobilized EphB3 with a candidate antibody and (b) detecting binding of the candidate antibody to the EphB3. In an alternative embodiment, the candidate antibody is immobilized and binding of EphB3 is detected. Immobilization is accomplished using any of the methods well known in the art, including covalent bonding to a support, a bead, or a chromatographic resin, as well as non-covalent, high affinity interaction such as antibody binding, or use of streptavidin/biotin binding wherein the immobilized compound includes a biotin moiety. Detection of binding can be accomplished (i) using a radioactive label on the compound that is not immobilized, (ii) using a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

Antibodies that increase the activity of the target antigen may be identified by incubating a candidate antibody with target antigen (or a cell expressing target antigen) and determining the effect of the candidate antibody on the activity or expression of the target antigen. The activity in the presence of the test antibody is compared to the activity in the absence of the test antibody. Where the activity of the sample containing the test antibody is higher than the activity in the sample lacking the test antibody, the antibody will have increased activity. The selectivity of an antibody that modulates the activity of a target antigen polypeptide or polynucleotide can be evaluated by comparing its effects on the target antigen to its effect on other related compounds.

In particular exemplary embodiments, it is contemplated that the antibodies are tested for their effect in a cultured cell system to determine their ability to induce receptor phosphorylation, oligomerization, internalization, degradation, signaling, and/or EphB3-mediated cell-cell adhesion. Additionally, cellular assays including proliferation assays, soft agar assays, and/or cytotoxicity assays as described herein may be used to evaluate a particular EphB3 antibody.

The biological activity of a particular antibody, or combination of antibodies, may be evaluated in vivo using a suitable animal model. For example, xenograft cancer models wherein human cancer cells are introduced into immune compromised animals, such as nude or SCID mice, may be used. Efficacy may be predicted using assays which measure inhibition of tumor formation, tumor regression or metastasis, and the like.

The invention also comprehends high throughput screening (HTS) assays to identify antibodies that interact with or induce biological activity (i.e., induce internalization or intracellular signaling, etc.) of target antigen. HTS assays permit screening of large numbers of compounds in an efficient manner. Cell-based HTS systems are contemplated to investigate the interaction between target antigen and its binding partners. HTS assays are designed to identify "hits" or "lead compounds" having the desired property, from which modifications can be designed to improve the desired property.

In another embodiment of the invention, high throughput screening for antibody fragments or CDRs with 1, 2, 3 or more modifications to amino acids within the CDRs having suitable binding affinity to a target antigen polypeptide is employed.

Combination Therapy

Having identified more than one antibody that is effective in an animal model, it may be further advantageous to mix two or more such antibodies together (which bind to the same or different target antigens) to provide still improved efficacy. Compositions comprising one or more antibody may be administered to persons or mammals suffering from, or predisposed to suffer from, cancer. Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

Although antibody therapy may be useful for all stages of cancers, antibody therapy may be particularly appropriate in advanced or metastatic cancers. Combining the antibody therapy method with a chemotherapeutic or radiation regimen may be preferred in patients that have not received chemotherapeutic treatment, whereas treatment with the antibody therapy may be indicated for patients who have received one or more chemotherapies. Additionally, antibody therapy can also enable the use of reduced dosages of concomitant chemotherapy, particularly in patients that do not tolerate the toxicity of the chemotherapeutic agent very well.

The methods of the invention contemplate the administration of single antibodies, as well as combinations, or "cocktails", of different antibodies. Such antibody cocktails may have certain advantages inasmuch as they contain antibodies which exploit different effector mechanisms or combine directly cytotoxic antibodies with antibodies that rely on immune effector functionality. Such antibodies in combination may exhibit synergistic therapeutic effects.

The methods of the invention further contemplate the administration of single antibodies or antibody cocktails in combination with the medically-recognized standard of care for the particular cancer being treated (e.g., lung, ovarian, esophageal, colon or breast cancer).

A cytotoxic agent refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see, e.g., U.S. Patent Publications 2003/0028071 and 2003/0032995 which are incorporated by reference herein). Such agents may be conjugated, coupled, linked or associated with an antibody according to the invention.

Cancer chemotherapeutic agents include, without limitation, alkylating agents, such as carboplatin and cisplatin; nitrogen mustard alkylating agents; nitrosourea alkylating agents, such as carmustine (BCNU); antimetabolites, such as methotrexate; folinic acid; purine analog antimetabolites, mercaptopurine; pyrimidine analog antimetabolites, such as fluorouracil (5-FU) and gemcitabine (Gemzar®); hormonal antineoplastics, such as goserelin, leuprolide, and tamoxifen; natural antineoplastics, such as aldesleukin, interleukin-2, docetaxel, etoposide (VP-16), interferon alfa, paclitaxel (Taxol®), and tretinoin (ATRA); antibiotic natural antineoplastics, such as bleomycin, dactinomycin, daunorubicin, doxorubicin, daunomycin and mitomycins including mitomycin C; and vinca alkaloid natural antineoplastics, such as vinblastine, vincristine, vindesine; hydroxyurea; aceglatone, adriamycin, ifosfamide, enocitabine, epitiostanol, aclarubicin, ancitabine, nimustine, procarbazine hydrochloride, carboquone, carboplatin, carmofur, chromomycin A3, antitumor polysaccharides, antitumor platelet factors, cyclophosphamide (Cytoxin®), Schizophyllan, cytarabine (cytosine arabinoside), dacarbazine, thioinosine, thiotepa, tegafur, dolastatins, dolastatin analogs such as auristatin, CPT-11 (irinotecan), mitozantrone, vinorelbine, teniposide, aminopterin, caminomycin, esperamicins (See, e.g., U.S. Pat. No. 4,675,187), neocarzinostatin, OK-432, bleomycin, furtulon, broxuridine, busulfan, honvan, peplomycin, bestatin (Ubenimex®), interferon-β, mepitiostane, mitobronitol, melphalan, laminin peptides, lentinan, Coriolus versicolor extract, tegafur/uracil, estramustine (estrogen/mechlorethamine).

Further, additional agents used as therapy for cancer patients include EPO, G-CSF, ganciclovir; antibiotics, leuprolide; meperidine; zidovudine (AZT); interleukins 1 through 18, including mutants and analogues; interferons or cytokines, such as interferons α, β, and γ hormones, such as luteinizing hormone releasing hormone (LHRH) and analogues and, gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α& β (TNF-α & β); invasion inhibiting factor-2 (IIF-2); bone morphogenetic proteins 1-7 (BMP 1-7); somatostatin; thymosin-α-1; γ-globulin; superoxide dismutase (SOD); complement factors; anti-angiogenesis factors; antigenic materials; and prodrugs.

Prodrug refers to a precursor or derivative form of a pharmaceutically active substance that is less cytotoxic or non-cytotoxic to tumor cells compared to the parent drug and is capable of being enzymatically activated or converted into an active or the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use herein include, but are not limited to, those chemotherapeutic agents described above.

Administration and Preparation

The antibodies of the invention may be formulated into pharmaceutical compositions comprising a carrier suitable for the desired delivery method. Suitable carriers include any material which, when combined with antibodies, retains the desired activity of the antibody and is nonreactive with the subject's immune systems. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Therapeutic formulations of the antibody are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

The antibody is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. In addition, the antibody is suitably administered by pulse infusion, particularly with declining doses of the antibody. Preferably the dosing is given by injections, most preferably intravenous or subcutaneous injections. Other administration methods are contemplated, including topical, particularly transdermal, transmucosal, rectal, oral or local administration e.g. through a catheter placed close to the desired site.

For nasal administration, the pharmaceutical formulations and medicaments may be a spray or aerosol containing an appropriate solvent(s) and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions. Other strategies known in the art may be used.

The formulations of the invention may be designed to be short-acting, fast-releasing, long-acting, or sustained-releasing as described herein. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Besides those representative dosage forms described above, pharmaceutically acceptable excipients and carries are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

Specific dosages may be adjusted depending on conditions of disease, the age, body weight, general health conditions, genotype, sex, and diet of the subject, dose intervals, administration routes, excretion rate, and combinations of drugs. Any of the above dosage forms containing effective amounts are well within the bounds of routine experimentation and therefore, well within the scope of the instant invention.

Antibodies of the invention will often be prepared substantially free of other naturally occurring immunoglobulins or other biological molecules. Preferred antibodies will also exhibit minimal toxicity when administered to a mammal afflicted with, or predisposed to suffer from cancer.

The compositions of the invention may be sterilized by conventional, well known sterilization techniques. The resulting solutions may be packaged for use or filtered under aseptic conditions and lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride and stabilizers (e.g., 120% maltose, etc.).

The antibodies of the present invention may also be administered via liposomes, which are small vesicles composed of various types of lipids and/or phospholipids and/or surfactant which are useful for delivery of a drug (such as the antibodies disclosed herein and, optionally, a chemotherapeutic agent). Liposomes include emulsions, foams, micelles, insoluble monolayers, phospholipid dispersions, lamellar layers and the like, and can serve as vehicles to target the antibodies to a particular tissue as well as to increase the half life of the composition. A variety of methods are available for preparing liposomes, as described in, e.g., U.S. Pat. Nos. 4,837,028 and 5,019,369, which patents are incorporated herein by reference.

Liposomes containing the antibody are prepared by methods known in the art, such as described in Epstein et al., Proc. Natl. Acad. Sci. USA 82: 3688 (1985); Hwang et al., Proc. Natl. Acad. Sci. USA 77: 4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257: 286-288 (1982) via a disulfide interchange reaction. A chemotherapeutic agent (such as Doxorubicin) is optionally contained within the liposome [see, e.g., Gabizon et al., J. National Cancer Inst. 81(19): 1484 (1989)].

The concentration of antibody in these compositions can vary widely, i.e., from less than about 10%, usually at least about 25% to as much as 75% or 90% by weight and will be selected primarily by fluid volumes, viscosities, etc., in accordance with the particular mode of administration selected. Actual methods for preparing orally, topically and parenterally administrable compositions will be known or apparent to those skilled in the art and are described in detail in, for example, Remington's Pharmaceutical Science, 19th ed., Mack Publishing Co., Easton, Pa. (1995), which is incorporated herein by reference.

Determination of an effective amount of a composition of the invention to treat disease in a patient can be accomplished through standard empirical methods which are well known in the art. An amount adequate to accomplish this is defined as a "therapeutically effective dose." Effective amounts of an antibody will vary and depend on the severity of the disease and the weight and general state of the patient being treated, but generally range from about 1.0 µg/kg to about 100 mg/kg body weight. Exemplary doses may range from about 10 µg/kg to about 30 mg/kg, or from about 0.1 mg/kg to about 20 mg/kg or from about 1 mg/kg to about 10 mg/kg per application. Antibody may also be dosed by body surface area (e.g. up to 4.5 g/square meter). Other exemplary doses of antibody include up to 8 g total in a single administration (assuming a body weight of 80 kg or body surface area of 1.8 square meters).

Administration may be by any means known in the art. For example, antibody may be administered by one or more separate bolus administrations, or by short or long term infusion over a period of, e.g., 5, 10, 15, 30, 60, 90, 120 minutes or more. Following an initial treatment period, and depending on the patient's response and tolerance of the therapy, maintenance doses may be administered, e.g., weekly, biweekly, every 3 weeks, every 4 weeks, monthly, bimonthly, every 3 months, or every 6 months, as needed to maintain patient response. More frequent dosages may be needed until a desired suppression of disease symptoms occurs, and dosages may be adjusted as necessary. The progress of this therapy is easily monitored by conventional techniques and assays. The therapy may be for a defined period or may be chronic and continue over a period of years until disease progression or death.

Single or multiple administrations of the compositions can be carried out with the dose levels and pattern being selected by the treating physician. For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

In any event, the formulations should provide a quantity of therapeutic antibody over time that is sufficient to exert the desired biological activity, e.g. prevent or minimize the severity of cancer. The compositions of the present invention may be administered alone or as an adjunct therapy in conjunction with other therapeutics known in the art for the treatment of such diseases.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The therapeutically effective amount of the antibody to be administered will be governed by such considerations, and is the minimum amount necessary to prevent, ameliorate, or treat the target-mediated disease, condition or disorder. Such amount is preferably below the amount that is toxic to the host or renders the host significantly more susceptible to infections.

The antibody need not be, but is optionally formulated with one or more agents currently used to prevent or treat the disorder in question. The effective amount of such other agents depends on the amount of antibody present in the formulation, the type of disease, condition or disorder or treatment, and other factors discussed above. These are generally used in the same dosages and with administration routes as used hereinbefore or about from 1 to 99% of the heretofore employed dosages.

In another embodiment of the invention, there is provided an article of manufacture containing materials useful for the treatment of the desired condition. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody of the invention. The label on, or associated with, the container indicates that the composition is used for treating the condition of choice. The article of manufacture may further comprise a second container containing a second therapeutic agent (including any of the second therapeutic agents for diseases discussed herein or known in the art). The article of manufacture may further comprise another container containing a pharmaceutically-acceptable buffer, such as phosphate-buffered saline, Ringer's solution or dextrose solution for reconstituting a lyophilized antibody formulation. It may further include other materials desirable from a commercial and user standpoint, including other buffers, diluents, filters, needles, syringes, and package inserts with instructions for use.

Immunotherapy

Antibodies useful in treating patients having cancers include those which are capable of initiating a potent immune response against the tumor and those which are capable of direct cytotoxicity. Antibodies conjugated to cytotoxic agents may be used to target the cytotoxic agents to tumor tissues expressing EphB3. Alternatively, antibodies may elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, antibodies that exert a direct biological effect on tumor growth are useful in the practice of the invention. Potential mechanisms by which such directly cytotoxic antibodies may act include inhibition of cell growth, modulation of cellular differentiation, modulation of tumor angiogenesis factor profiles, and the induction of apoptosis. The mechanism by which a particular antibody exerts an anti-tumor effect may be evaluated using any number of in vitro assays designed to determine ADCC, ADMMC, complement-mediated cell lysis, and so forth, as is generally known in the art.

Anti-EphB3 antibodies may be administered in their "naked" or unconjugated form, or may be conjugated directly to other therapeutic or diagnostic agents, or may be conjugated indirectly to carrier polymers comprising such other therapeutic or diagnostic agents.

Antibodies can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are well known in the art; for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

Conjugation of antibody moieties is described in U.S. Pat. No. 6,306,393. General techniques are also described in Shih et al., Int. J. Cancer 41:832-839 (1988); Shih et al., Int. J. Cancer 46:1101-1106 (1990); and Shih et al., U.S. Pat. No. 5,057,313. This general method involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer may be, for example, an aminodextran or polypeptide of at least 50 amino acid residues. Various techniques for conjugating a drug or other agent to the carrier polymer are known in the art. A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and conjugate.

Alternatively, conjugated antibodies can be prepared by directly conjugating an antibody component with a therapeutic agent. The general procedure is analogous to the indirect method of conjugation except that a therapeutic agent is directly attached to an oxidized antibody component. For example, a carbohydrate moiety of an antibody can be attached to polyethyleneglycol to extend half-life.

Alternatively, a therapeutic agent can be attached at the hinge region of a reduced antibody component via disulfide bond formation, or using a heterobifunctional cross-linker, such as N-succinyl 3-(2-pyridyldithio)proprionate (SPDP). Yu et al., Int. J. Cancer 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Enineering and Clinical Application, Ritter et al. (eds.), pages 60-84 (Cambridge University Press 1995). A variety of bifunctional protein coupling agents are known in the art, such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Finally, fusion proteins can be constructed that comprise one or more anti-EphB3 antibody moieties and another polypeptide. Methods of making antibody fusion proteins are well known in the art. See, e.g., U.S. Pat. No. 6,306,393. Antibody fusion proteins comprising an interleukin-2 moiety are described by Boleti et al., Ann. Oncol. 6:945 (1995), Nicolet et al., Cancer Gene Ther. 2:161 (1995), Becker et al., Proc. Nat'l Acad. Sci. USA 93:7826 (1996), Hank et al., Clin. Cancer Res. 2:1951 (1996), and Hu et al., Cancer Res. 56:4998 (1996).

The antibodies of the invention may be administered in their "naked" or unconjugated form, or may have therapeutic agents conjugated to them. In one embodiment, the antibodies of the invention are used as a radiosensitizer. In such embodiments, the antibodies are conjugated to a radiosensitizing agent. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Diseases that are treatable with electromagnetic radiation include neoplastic diseases, benign and malignant tumors, and cancerous cells.

The terms "electromagnetic radiation" and "radiation" as used herein include, but are not limited to, radiation having the wavelength of $10^{-20}$ to 100 meters. Preferred embodiments of the present invention employ the electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1.0 mm), and microwave radiation (1 mm to 30 cm).

Radiosensitizers are known to increase the sensitivity of cancerous cells to the toxic effects of electromagnetic radiation. Many cancer treatment protocols currently employ radiosensitizers activated by the electromagnetic radiation of X-rays. Examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin(r), benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

In another embodiment, the antibody may be conjugated to a receptor (such streptavidin) for utilization in tumor pretargeting wherein the antibody-receptor conjugate is administered to the patient, followed by removal of unbound conjugate from the circulation using a clearing agent and then administration of a ligand (e.g., avidin) which is conjugated to a cytotoxic agent (e.g., a radionuclide).

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are well known in the art; for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

"Label" refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable. Alternatively, the label may not be detectable on its own but may be an element that is bound by another agent that is detectable (e.g. an epitope tag or one of a binding partner pair such as biotin-avidin, etc.) Thus, the antibody may comprise a label or tag that facilitates its isolation, and methods of the invention to identify antibodies include a step of isolating the antibody through interaction with the label or tag.

Exemplary therapeutic immunoconjugates comprise the antibody described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fusion proteins are described in further detail below.

Production of immunoconjugates is described in U.S. Pat. No. 6,306,393. Immunoconjugates can be prepared by indirectly conjugating a therapeutic agent to an antibody component. General techniques are described in Shih et al., Int. J. Cancer 41:832-839 (1988); Shih et al., Int. J. Cancer 46:1101-1106 (1990); and Shih et al., U.S. Pat. No. 5,057,313. The general method involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer is preferably an aminodextran or polypeptide of at least 50 amino acid residues, although other substantially equivalent polymer carriers can also be used. Preferably, the final immunoconjugate is soluble in an aqueous solution, such as mammalian serum, for ease of administration and effective targeting for use in therapy. Thus, solubilizing functions on the carrier polymer will enhance the serum solubility of the final immunoconjugate. In particular, an aminodextran will be preferred.

The process for preparing an immunoconjugate with an aminodextran carrier typically begins with a dextran polymer, advantageously a dextran of average molecular weight of about 10,000-100,000. The dextran is reacted with an oxidizing agent to affect a controlled oxidation of a portion of its carbohydrate rings to generate aldehyde groups. The oxidation is conveniently effected with glycolytic chemical reagents such as $NaIO_4$, according to conventional procedures.

The oxidized dextran is then reacted with a polyamine, preferably a diamine, and more preferably, a mono- or polyhydroxy diamine. Suitable amines include ethylene diamine, propylene diamine, or other like polymethylene diamines, diethylene triamine or like polyamines, 1,3-diamino-2-hydroxypropane, or other like hydroxylated diamines or polyamines, and the like. An excess of the amine relative to the aldehyde groups of the dextran is used to ensure substantially complete conversion of the aldehyde functions to Schiff base groups.

A reducing agent, such as $NaBH_4$, $NaBH_3$ CN or the like, is used to effect reductive stabilization of the resultant Schiff base intermediate. The resultant adduct can be purified by passage through a conventional sizing column to remove cross-linked dextrans.

Other conventional methods of derivatizing a dextran to introduce amine functions can also be used, e.g., reaction with cyanogen bromide, followed by reaction with a diamine.

The aminodextran is then reacted with a derivative of the particular drug, toxin, chelator, immunomodulator, boron addend, or other therapeutic agent to be loaded, in an activated form, preferably, a carboxyl-activated derivative, prepared by conventional means, e.g., using dicyclohexylcarbodiimide (DCC) or a water soluble variant thereof, to form an intermediate adduct.

Alternatively, polypeptide toxins such as pokeweed antiviral protein or ricin A-chain, and the like, can be coupled to aminodextran by glutaraldehyde condensation or by reaction of activated carboxyl groups on the protein with amines on the aminodextran.

Chelators for radiometals or magnetic resonance enhancers are well-known in the art. Typical are derivatives of ethylenediaminetetraacetic acid (EDTA) and diethylenetriaminepentaacetic acid (DTPA). These chelators typically have groups on the side chain by which the chelator can be attached to a carrier. Such groups include, e.g., benzylisothiocyanate, by which the DTPA or EDTA can be coupled to the amine group of a carrier. Alternatively, carboxyl groups or amine groups on a chelator can be coupled to a carrier by activation or prior derivatization and then coupling, all by well-known means.

Boron addends, such as carboranes, can be attached to antibody components by conventional methods. For example, carboranes can be prepared with carboxyl functions on pendant side chains, as is well known in the art. Attachment of such carboranes to a carrier, e.g., aminodextran, can be achieved by activation of the carboxyl groups of the carboranes and condensation with amines on the carrier to produce an intermediate conjugate. Such intermediate conjugates are then attached to antibody components to produce therapeutically useful immunoconjugates, as described below.

A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and immunoconjugate.

Conjugation of the intermediate conjugate with the antibody component is effected by oxidizing the carbohydrate portion of the antibody component and reacting the resulting aldehyde (and ketone) carbonyls with amine groups remaining on the carrier after loading with a drug, toxin, chelator, immunomodulator, boron addend, or other therapeutic agent. Alternatively, an intermediate conjugate can be attached to an oxidized antibody component via amine groups that have been introduced in the intermediate conjugate after loading with the therapeutic agent. Oxidation is conveniently effected either chemically, e.g., with $NaIO_4$ or other glycolytic reagent, or enzymatically, e.g., with neuraminidase and galactose oxidase. In the case of an aminodextran carrier, not all of the amines of the aminodextran are typically used for loading a therapeutic agent. The remaining amines of aminodextran condense with the oxidized antibody component to form Schiff base adducts, which are then reductively stabilized, normally with a borohydride reducing agent.

Analogous procedures are used to produce other immunoconjugates according to the invention. Loaded polypeptide carriers preferably have free lysine residues remaining for condensation with the oxidized carbohydrate portion of an antibody component. Carboxyls on the polypeptide carrier can, if necessary, be converted to amines by, e.g., activation with DCC and reaction with an excess of a diamine.

The final immunoconjugate is purified using conventional techniques, such as sizing chromatography on Sephacryl S-300 or affinity chromatography using one or more CD84Hy epitopes.

Alternatively, immunoconjugates can be prepared by directly conjugating an antibody component with a therapeutic agent. The general procedure is analogous to the indirect method of conjugation except that a therapeutic agent is directly attached to an oxidized antibody component.

It will be appreciated that other therapeutic agents can be substituted for the chelators described herein. Those of skill in the art will be able to devise conjugation schemes without undue experimentation.

As a further illustration, a therapeutic agent can be attached at the hinge region of a reduced antibody component via disulfide bond formation. For example, the tetanus toxoid peptides can be constructed with a single cysteine residue that is used to attach the peptide to an antibody component. As an alternative, such peptides can be attached to the antibody component using a heterobifunctional cross-linker, such as N-succinyl 3-(2-pyridyldithio)proprionate (SPDP). Yu et al., Int. J. Cancer 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Enineering and Clinical Application, Ritter et al. (eds.), pages 60-84 (Cambridge University Press 1995).

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionuclide to the antibody (see, e.g., WO94/11026).

As described above, carbohydrate moieties in the Fc region of an antibody can be used to conjugate a therapeutic agent. However, the Fc region may be absent if an antibody fragment is used as the antibody component of the immunoconjugate. Nevertheless, it is possible to introduce a carbohydrate moiety into the light chain variable region of an antibody or antibody fragment. See, for example, Leung et al., J. Immunol. 154:5919 (1995); Hansen et al., U.S. Pat. No. 5,443,953. The engineered carbohydrate moiety is then used to attach a therapeutic agent.

In addition, those of skill in the art will recognize numerous possible variations of the conjugation methods. For example, the carbohydrate moiety can be used to attach polyethyleneglycol in order to extend the half-life of an intact antibody, or antigen-binding fragment thereof, in blood, lymph, or other extracellular fluids. Moreover, it is possible to construct a "divalent immunoconjugate" by attaching therapeutic agents to a carbohydrate moiety and to a free sulflhydryl group. Such a free sulflhydryl group may be located in the hinge region of the antibody component.

Antibody Fusion Proteins

The present invention contemplates the use of fusion proteins comprising one or more antibody moieties and another polypeptide, such as an immunomodulator or toxin moiety. Methods of making antibody fusion proteins are well known in the art. See, e.g., U.S. Pat. No. 6,306,393. Antibody fusion proteins comprising an interleukin-2 moiety are described by Boleti et al., Ann. Oncol. 6:945 (1995), Nicolet et al., Cancer Gene Ther. 2:161 (1995), Becker et al., Proc. Nat'l Acad. Sci. USA 93:7826 (1996), Hank et al., Clin. Cancer Res. 2:1951 (1996), and Hu et al., Cancer Res. 56:4998 (1996). In addition, Yang et al., Hum. Antibodies Hybridomas 6:129 (1995), describe a fusion protein that includes an F(ab')$_2$ fragment and a tumor necrosis factor alpha moiety.

Methods of making antibody-toxin fusion proteins in which a recombinant molecule comprises one or more antibody components and a toxin or chemotherapeutic agent also are known to those of skill in the art. For example, antibody-*Pseudomonas* exotoxin A fusion proteins have been described by Chaudhary et al., Nature 339:394 (1989), Brinkmann et al., Proc. Nat'l Acad. Sci. USA 88:8616 (1991), Batra et al., Proc. Nat'l Acad. Sci. USA 89:5867 (1992), Friedman et al., J. Immunol. 150:3054 (1993), Wels et al., Int. J. Can. 60:137 (1995), Fominaya et al., J. Biol. Chem. 271:10560 (1996), Kuan et al., Biochemistry 35:2872 (1996), and Schmidt et al., Int. J. Can. 65:538 (1996). Antibody-toxin fusion proteins containing a diphtheria toxin moiety have been described by Kreitman et al., Leukemia 7:553 (1993), Nicholls et al., J. Biol. Chem. 268:5302 (1993), Thompson et al., J. Biol. Chem. 270:28037 (1995), and Vallera et al., Blood 88:2342 (1996). Deonarain et al., Tumor Targeting 1:177 (1995), have described an antibody-toxin fusion protein having an RNase moiety, while Linardou et al., Cell Biophys. 24-25:243 (1994), produced an antibody-toxin fusion protein comprising a DNase I component. Gelonin was used as the toxin moiety in the antibody-toxin fusion protein of Wang et al., Abstracts of the 209th ACS National Meeting, Anaheim, Calif., Apr. 2-6, 1995, Part 1, BIOT005. As a further example, Dohlsten et al., Proc. Nat'l Acad. Sci. USA 91:8945 (1994), reported an antibody-toxin fusion protein comprising Staphylococcal enterotoxin-A.

Illustrative of toxins which are suitably employed in the preparation of such conjugates are ricin, abrin, ribonuclease, DNase I, Staphylococcal enterotoxin-A, pokeweed antiviral protein, gelonin, diphtherin toxin, *Pseudomonas* exotoxin, and *Pseudomonas* endotoxin. See, for example, Pastan et al., Cell 47:641 (1986), and Goldenberg, Calif.—A Cancer Journal for Clinicians 44:43 (1994). Other suitable toxins are known to those of skill in the art.

Antibodies of the present invention may also be used in ADEPT by conjugating the antibody to a prodrug-activating enzyme which converts a prodrug (e.g., a peptidyl chemotherapeutic agent, See WO81/01145) to an active anti-cancer drug. See, for example, WO88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as abzymes, can be used to convert the prodrugs of the invention into free active drugs (See, e.g., Massey, Nature 328: 457-458 (1987)). Antibody-abzyme conjugates can be prepared as described herein for delivery of the abzyme to a tumor cell population.

The enzymes of this invention can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (See, e.g., Neuberger et al., Nature 312: 604-608 (1984))

Non-Therapeutic Uses

The antibodies of the invention may be used as affinity purification agents for target antigen or in diagnostic assays for target antigen, e.g., detecting its expression in specific cells, tissues, or serum. The antibodies may also be used for in vivo diagnostic assays. Generally, for these purposes the antibody is labeled with a radionuclide (such as $^{111}$In, $^{99}$Tc, $^{14}$C, $^{131}$I, $^{125}$I, $^{3}$H, $^{32}$P or $^{35}$S) so that the tumor can be localized using immunoscintiography.

The antibodies of the present invention may be employed in any known assay method, such as competitive binding assays, direct and indirect sandwich assays, such as ELISAs, and immunoprecipitation assays. Zola, Monoclonal Antibodies: A Manual of Techniques, pp. 147-158 (CRC Press, Inc. 1987). The antibodies may also be used for immunohistochemistry, to label tumor samples using methods known in the art.

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

EXAMPLES

The invention is illustrated by the following examples, which are not intended to be limiting in any way.

Example 1

Preparation of EphB3 Extracellular Domain (ECD)

For recombinant expression of the ECD of EphB3, a nested PCR approach was first undertaken to incorporate tags and to engineer the ends of the coding region in preparation for incorporation into an expression vector. Primers used were as follows (all are written as 5' to 3' sequences):

```
Forward #1:
                                    (SEQ ID NO: 422)
TCGTATACATTTCTTACATCTATGCGCTGGAAGAGACCCTCATGGACACA

AA

Forward #2:
                                    (SEQ ID NO: 423)
GGGACAAGTTTGTACAAAAAAGCAGGCTACGAAGGAGATATACATATGAA

ATTCTTAGTCAACGTTGCCCTTGTTTTTATGGTCGTATACATTTCTTACA

TCTATGCG

Reverse #1:
                                    (SEQ ID NO: 424)
CGGGTCGTCGAGGTCCTCGTCGAAGGGCCTCGTGTAGTGGTAGTGGTAGT

GCCT

Reverse #2:
                                    (SEQ ID NO: 425)
CCTCGTGTAGTGGTAGTGGTAGTGCCTCGAATTTGGGTCGAAAGAACATG

TTTCACCAGGG
```

PCR amplification was carried out using PfuUltra™ Hotstart PCR Master Mix (Stratagene) according to manufacturer's recommendation. The template used for the amplification was an EphB3 ECD fragment cloned in pDONOR201. The ECD PCR product was cloned into pBlueBac4.5GW using the topoisomerase cloning strategy. The final selected clones were confirmed by double-strand sequencing. 10-20 μg of DNA representing each clone was prepared for insect transfection.

The recombinant constructs were used to express the EphB3 ECD in insect cells as follows. Baculovirus was isolated by plaque purification of a co-transfection of plasmid DNA encoding the extracellular domain of EphB3 with Sapphire™ genomic *Autographa californica* DNA. Recombinant virus was amplified and used to infect Tn5 insect cells at densities ranging from 1–1.5×10⁶ cells per ml, multiplicity of infection (moi) range of 2-10 in a 10 L (working volume) wave bioreactor. Following 48 hours of infection, cells and supernatant were collected and centrifuged, and the supernatant was prepared for concentration. Supernatant was clarified on a 0.45 μm hollow fiber cartridge before 8× concentration with a tangential flow 10 kDa MW cut-off membrane. Prior to protein purification, the supernatant was filter sterilized with a 1 L, 0.2 um pore vacuum flasks.

EphB3 ECD was purified as follows. Insect cell culture supernatant containing EphB3 ECD was passed at a flow rate of 13 ml/min over a 25 mL Ni Chelating column (G.E. resin Catalog Number 17-5318-03) equilibrated in Buffer A (PBS/ 0.35M NaCl/5 mM Imidazole). The bound protein containing EphB3 ECD was eluted using a 30-column-volume gradient from Buffer A to Buffer B (PBS/0.35M NaCl/250 mM Imidazole). Fractions were examined by SDS-PAGE, and those containing EphB3 ECD at the desired purity were pooled. The pool was dialyzed vs. Buffer A and passed over 2×5 mL HisTrap (G.E.) columns. The HisTrap columns were eluted in the same fashion as the first Ni Chelating column. Fractions were examined by SDS-PAGE, and those containing EphB3 ECD protein at the desired purity were pooled. The final pool was dialyzed vs. PBS/0.1M Arginine. The final material was analyzed for identity and purity by N-terminal sequencing as well as reduced and non-reduced SDS-PAGE (Coomassie staining and Western analysis).

Example 2

Identification of Target-Specific Antibodies Secreted by Murine Hybridomas

The immunogen used for hybridoma generation was a recombinant form of the extracellular domain (ECD) (corresponding to amino acids 37-558 of SEQ ID NO: 2) of human EphB3, which was generated using the baculovirus/insect cell expression system. For the immunizations, the ECD was mixed with an equal volume of adjuvant, and the mixture was injected subcutaneously on the ventral surface of the hind limb footpads. Mice were injected with the immunogen every 3-14 days according to various immunization schedules, to produce a strong immune response. Mice showing a good immune response were then sacrificed, the lymph nodes were harvested, and the B cells in the lymph nodes were collected. The B cells were then fused to myeloma cells to produce hybridomas according to techniques well known in the art, and the hybridomas were screened for those producing antibodies recognizing EphB3 protein in ELISA and FACS assays.

Example 3

Identification of Target-Specific Antibodies by Phage Display

Screening Antibodies.

To isolate a panel of anti-EphB3 antibodies with agonistic activity, an Omniclonal phage display library (Buechler et al. U.S. Pat. No. 6,057,098) was screened that has been generated from mice hyperimmunized with the ecxtracellular domain (ECD) of EphB3.

Single colonies, obtained from the Omniclonal library according to the protocol in U.S. Pat. No. 6,057,098, were screened for binding activity in an ELISA assay. Briefly, microcultures were grown to an $OD_{600}$=0.6 at which point expression of soluble antibody fragment was induced by addition of 0.2% w/v of arabinose followed by overnight culture in a shaker incubator at 30° C. Bacteria were spun down and periplasmic extract was prepared and used to detect antibody binding activity to EphB3-ECD immobilized on Nunc MaxiSorp™ microplates following the standard ELISA protocol provided by the microplate manufacturer. Antibody binding was also assesed by measuring binding to CHO-K1-EphB3 expressing cells using Fluorescence Activated Cell Sorting (FACS) analysis.

Converting Antibody Candidates Identified by Phage Display to Whole IgG

To convert the lead candidate binders from the initial screen to antibodies comprising antibody heavy and light chain constant regions, the coding sequences for the variable regions of both the heavy and light chains of binders were cloned into a proprietary mammalian expression vector (WO 2004/033693) encoding for the kappa (κ) and gamma-1 (γ1) constant region genes.

Antibodies were transiently expressed in 293E cells as described in Handa et al (2004 American Society of Cancer Biology Poster #1937). Supernatant of transfected cells were harvested at day 6 of culture and IgG was purified using Protein A Sepharose (GE HEalthcare) following the manufacturers protocol.

Example 4

Affinity Determination of Selected Anti-EphB3 Antibodies

Protocol 1:

Protein A was immobilized onto CM5 biosensor chips via amine coupling. Anti-EphB3 antibodies, at 0.75 µg/ml, were diluted 1:100 in HBS-EP Buffer (0.1M HEPES pH7.4, 0.15M NaCl, 3 mM EDTA, 0.005% Surfactant P20), and captured onto the modified biosensor surface for 1.5 minutes. Recombinant soluble EphB3 ECD (extracellular domain) was flowed over the biosensor surface at varying concentrations in HBS-EP Buffer. Kinetic and affinity constants were determined using a combination of Scrubber and BiaEvaluation software with a 1:1 interaction model/global fit.

Protocol 2:

Rat anti-mouse Fc (RamFc) was immobilized onto CM5 biosensor chips via amine coupling. Anti-EphB3 antibodies, at 0.75 µg/ml, were diluted 1:200 in HBS-EP Buffer, and captured onto the modified biosensor surface for 1.5 minutes. Recombinant soluble EphB3 ECD was flowed over the biosensor surface at varying concentrations in HBS-EP Buffer. Kinetic and affinity constants were determined using a combination of Scrubber and BiaEvaluation software with a 1:1 interaction model/global fit.

Results of the affinity experiments are set out below in Table 3.

TABLE 3

| Antibody | $K_a$ (M$^{-1}$ sec$^{-1}$) | $K_d$ (sec$^{-1}$) | $K_D$ (nM) |
|---|---|---|---|
| XHA.05.337 | 3.53e4 | 2.79e-3 | 79 |
| XHA.05.228 | 2.15e4 | 4.52e-3 | 210 |
| XHA.05.200 | 4.86e4 | 1.39e-3 | 28.6 |
| XHA.05.111* | 2.14e5 | 1.21e-2 | 57 |
| XHA.05.885* | 1.39e5 | 1.19e-3 | 8.5 |
| XPA.04.001 | 2.15e5 | 3.19e-4 | 1.5 |
| XPA.04.019 | 1.18e5 | 7.20e-4 | 6.1 |
| XPA.04.013 | 1.16e5 | 3.88e-4 | 3.4 |
| XPA.04.018 | 1.49e5 | 2.34e-4 | 1.6 |
| XPA.04.048 | 2.66e5 | 1.60e-4 | 0.6 |

*XHA.05.111 and XHA.05.885 were analyzed with RamFc format

Example 5

EphB3 Antibody Epitope Binning

The anti-EphB3 antibodies were assigned to epitope bins by a serial competition assay strategy using surface plasmon resonance (SPR) technologies. In this approach, one antibody was immobilized onto a sensor chip, either directly or through a capture agent, and allowed to bind the ligand (EphB3 ECD) as it was injected over the immobilized antibody. A second test antibody was subsequently injected, and its ability to bind the ligand captured by the first antibody was determined. If the antibodies bind to spatially separated epitopes on the ligand, the second antibody should also be able to bind the ligand/first antibody complex. The ability of two different antibodies to simultaneously bind the same molecule of ligand is referred to as pairing.

1. The first series of experiments utilized a CM5 sensor chip coated with a high density of Rabbit anti-Mouse Fc specific antibody (RAM-Fc) on all flow cells.
   a. The running buffer was HBS-EP (Biacore®, Inc.), the temperature was set at 25° C., and the flow rate was 10 µL/min.
   b. A different antibody was captured on each flow cell by injecting a 1-10 µg/mL dilution for 1-3 minutes resulting in a capture level of 200-1000 RU.
   c. The surface was then blocked by injecting 100 µg/mL mouse IgG in HBS-EP for 30 minutes.
   d. The antibody to be tested for pairing was injected at 1 µg/mL to verify that the chip was effectively blocked and to determine the background binding level of the antibody.
   e. The ligand was injected at 2-10 µg/mL for 2-4 minutes.
   f. The antibody to be paired was injected again as in step 1d above. If the antibody bound during this injection, the two antibodies form a pair, and therefore are placed in separate epitope bins. If the second antibody did not bind, it competes with the first antibody for binding, and they are placed in the same, or overlapping epitope bins.
   g. As a control for self-pairing, each of the captured antibodies was tested for pairing with itself.
2. Once several epitope bins, or unique sets of non-pairing antibodies, were elucidated, those antibodies were used to further investigate more of the antibodies. Four antibodies at a time were used to interrogate antibodies in a serial manner. By capturing a hybridoma antibody from a different epitope bin on each of the four flow cells, followed by performing the above-described pairing protocol across all four at once, a larger sample set was interrogated.
3. This process was used to evaluate the human antibody Fab fragments as well, with the modification that the blocking step using the 100 µg/mL mouse IgG was not used, as the RAM-Fc surface does not capture the human Fabs.

As a result of the competition experiments, the epitope bins shown in Table 4 were defined. All of the antibodies with the highest binding affinity (see Example 4 above) are in BIN 3.

TABLE 4

| Epitope Bins from Biacore ® 2000 pairing data. | | | | | | | |
|---|---|---|---|---|---|---|---|
| BIN 1 | BIN 2 | BIN 3 | BIN 4 | BIN 5 | BIN 6 | BIN 7 | BIN 8 |
| XHA.05.465 | XHA.05.119 | XHA.05.964 | XHA.05.660 | XHA.05.676 | XHA.05.030 | XHA.05.200 | XHA.05.111 |
| XHA.05.783 | XHA.05.228 | XHA.05.653 | XHA.05.552 | | | XHA.05.005 | |
| XHA.05.031 | XHA.05.337 | XHA.05.885 | XHA.05.949 | | | XHA.05.001 | |
| XHA.05.942 | XHA.05.440 | XPA.04.001 | XHA.05.151 | | | XHA.05.888 | |
| XHA.05.751 | XPA.04.022 | XPA.04.013 | XPA.04.019 | | | | |
| XHA.05.599 | | XPA.04.018 | | | | | |
| XPA.04.031 | | XPA.04.036 | | | | | |
| XPA.04.030 | | XPA.04.046 | | | | | |
| XPA.04.040 | | XPA.04.048 | | | | | |

Example 6

Selection of Agonist EphB3 Antibodies Using Flow Cytometry-Based Assays and Detection of EphB3 Phosphorylation and Degradation To identify agonistic antibodies targeted to EphB3, two flow cytometry (FACS)-based assays were developed to monitor downstream effects of receptor activation: (1) total cellular phospho-tyrosine (pY), as a measure of activation of signaling pathways; and (2) receptor internalization, to measure down-regulation of activated receptor.

Total Cellular Tyrosine Phosphorylation

The total cellular pY assay employed a suspension-adapted, stably transfected CHO cell line expressing high levels of the receptor. This assay was used to screen hybridoma supernatants, purified hybridoma-derived antibodies, and purified whole IgG reformatted phage display-derived antibodies.

Suspension adapted CHO-K1 cells overexpressing EphB3 were seeded into a round bottom 96-well plate at $2 \times 10^5$ cells/well. Antibody against EphB3 was then diluted 1:10 directly into each sample well. Samples were incubated for 40-45 minutes at 37° C. After incubation, cells were fixed with 2% formaldehyde for 20 minutes at room temperature. Cells were then washed 2× with permeabilization buffer and resuspended in permeabilization buffer containing PE conjugated mouse anti-phosphotyrosine antibody (PY20). Cells were incubated for 1 hour at 4° C., washed 2× with permeabilization buffer, and analyzed by flow cytometry.

Approximately 24% of the antibodies tested showed agonistic activity in the pY assay. Immunoprecipitation followed by Western analysis (See below) was then performed on lysates from antibody-treated cells (EphB3 over-expressing CHO and tumor cell lines), and the data confirmed that the pY-inducing antibodies triggered phosphorylation of EphB3.

Assay for Determining Steady-State Levels of EphB3 on the Cell Surface

Top candidates identified using the total cellular pY assay were further characterized for cell surface EphB3 down-regulation and degradation. Epitope competition studies were first conducted using FACS and Biacore® to identify strong FACS-positive "detection" antibodies that showed minimal competition with the top pY-inducing antibodies. These antibodies were employed to develop a FACS-based assay monitoring cell surface EphB3 levels from 2 to 72 hours after addition of pY-inducing antibodies.

Suspension adapted SW620 cells were cultured for 2-72 hours with anti-EphB3 antibodies or recombinant ligand protein at 10 μg/mL. At each time point, cell surface levels of EphB3 were determined by flow cytometric analysis, using either a hybridoma-derived mouse anti-target detection antibody (for cells treated with chimeric human antibodies) or a chimeric human anti-target detection antibody (for cells treated with hybridoma derived antibodies). Although screening was done to select detection antibodies that showed minimal competition with the treatment antibodies for EphB3 binding, in most cases there were low levels of interference (10-20%). Maximum detection antibody binding was determined for each treatment antibody using conditions in which fresh SW620 cells were briefly pre-incubated with treatment antibody before staining with detection antibody.

A subset of the antibodies showed dramatic down-regulation of cell surface receptor by 2 hours that was maintained through 72 hours (see, e.g., FIG. 1).

IP-Western for Detection of Target Phosphorylation

Figure 2:
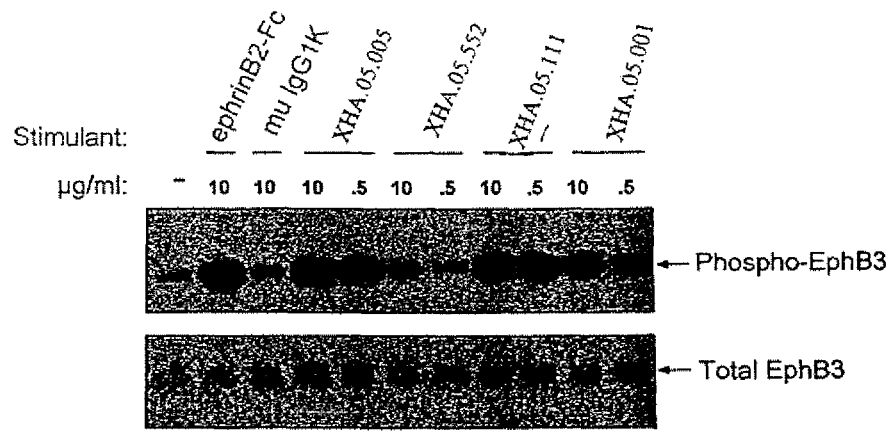
FIG. 2 shows that anti-EphB3 mAbs trigger phosphorylation of EphB3 in SW620 cells.
Figure 3:
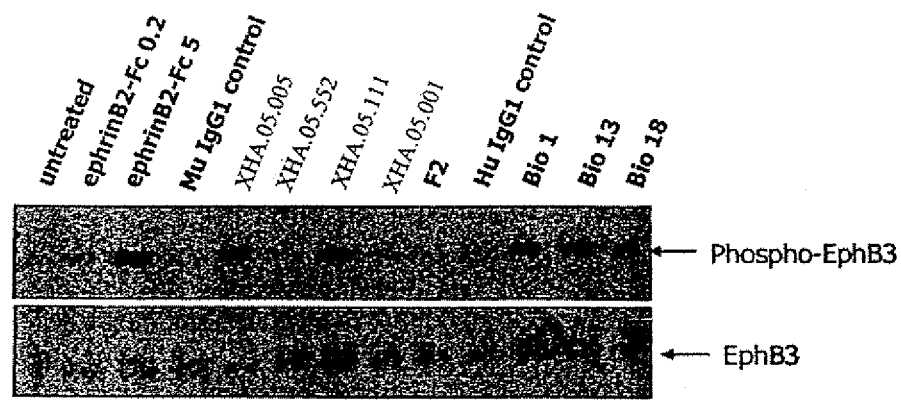
FIG. 3 shows that anti-EphB3 antibodies induce phosphorylation of EphB3 at a low antibody concentration.

Human cell lines expressing EphB3 were grown to sub-confluency, incubated in serum-free media for 30 minutes, and then treated with ligand or agonist antibody at various concentrations (0.2-10 ug/ml) for 30 minutes at 37° C. Cells were washed with PBS and lysed in Tris-buffered saline containing 1% Triton X-100 and 0.1% SDS in the presence of protease inhibitors (Roche Complete Mini, EDTA-free protease inhibitor cocktail tablets used according to manufacturer's instructions) and phosphatase inhibitors (Sigma phosphatase inhibitor cocktails 1 and 2, used according to manufacturer's recommendations). The target was immunoprecipitated from ~800 μg of clarified lysate using an anti-EphB3 specific antibody, resolved by SDS-PAGE, transferred to nitrocellulose, and subjected to Western blot analysis with an anti-phosphotyrosine antibody (4G10, Upstate). The blot was stripped and re-probed with an anti-EphB3 specific antibody to determine protein loading. As shown in FIG. 2, anti-EphB3 mAbs trigger phosphorylation of EphB3 in SW620 cells. As shown in FIG. 3, anti-EphB3 antibodies induce phosphorylation of EphB3 at a low (0.2 μg/ml) antibody concentration.

Western Blot to Confirm Degradation of the Target

Figure 4:
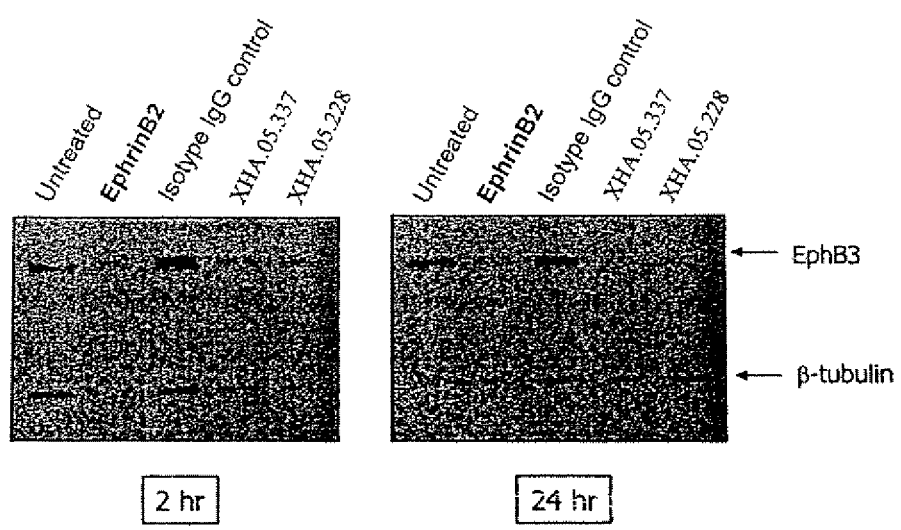
FIG. 4 shows that anti-EphB3 mAbs induce degradation, not just internalization of EphB3.
Figure 5:
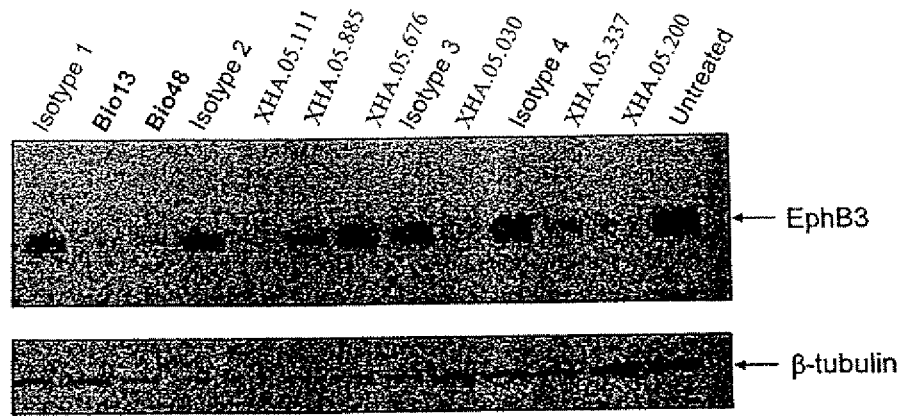
FIG. 5 shows that a subset of mAbs reduced the EphB3 protein level for at least 72 hours.
Figure 6:
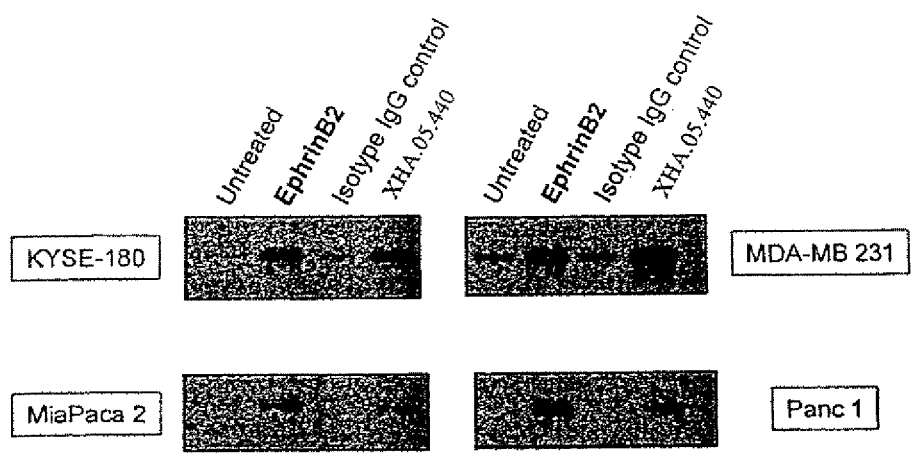
FIG. 6 shows that multiple cell lines respond to an agonist mAb by phosphorylating EphB3.

Human cell lines expressing EphB3 were left untreated or were treated with 10 μg/ml of ligand or agonist Abs for various time periods (2-72 hrs) in complete medium. The ligand or antibody was administered once at the start of the experiment. At the chosen time points, cells were washed with PBS and lysed in Tris-buffered saline containing 1% Triton X-100 and 0.1% SDS in the presence of protease inhibitors (Roche Complete Mini, EDTA-free protease inhibitor cocktail tablets used according to manufacturer's instructions) and phosphatase inhibitors (Sigma phosphatase inhibitor cocktails 1 and 2, used according to manufacturer's instructions). After clarification by centrifugation at 14,000 rpm for 10 minutes at 4° C., 40 μg of lysate was fractionated with SDS-PAGE, transferred to nitrocellulose and subjected to Western blot analysis with an anti-EphB3 specific antibody. β-tubulin was visualized as the loading control. Targets were detected by enhanced chemiluminescence and autoradiography. As shown in FIG. 4, anti-EphB3 mAbs induce degradation, not just internalization of EphB3. As shown in FIG. 5, a subset of mAbs reduced the EphB3 for at least 72 hours. Finally, as shown in FIG. 6, multiple cell lines respond to an agonist mAb by phosphorylating EphB3.

A summary of selected antibodies with respect to the aforementioned assays is set out in Table 5 below:

TABLE 5

| Antibody: | MFI: | total pY (fold increase): | Steady-state EphB3 (% reduction): | Bin: |
|---|---|---|---|---|
| XPA.04.048 | 611 | 1.7 | 47.2 | 3 |
| XPA.04.018 | 1610 | 1.7 | 46.4 | 3 |
| XPA.04.01 | 1171 | 1.6 | 46.9 | 3 |
| XPA.04.013 | 1283 | 1.6 | 49.8 | 3 |
| XHA.05.337 | 559 | 2.8 | 71.7 | 2 |
| XHA.05.200 | 942 | 1.5 | 70.4 | 7 |
| XHA.05.111 | 1110 | 1.5 | 69.4 | 8 |

TABLE 5-continued

| Antibody: | MFI: | total pY (fold increase): | Steady-state EphB3 (% reduction): | Bin: |
|---|---|---|---|---|
| XHA.05.005 | 1280 | 1.6 | 67.1 | 7 |
| XHA.05.228 | 666 | 3.3 | 66.8 | 2 |
| XHA.05.030 | 500 | 2 | 52 | 6 |
| XHA.05.964 | 800 | 1.5 | 48.6 | 3 |
| XHA.05.885 | 1200 | 1.8 | 56.4 | 3 |

Example 7

Humanization of Murine Antibodies

This example sets out a procedure for humanization of a murine anti-EphB3 antibody.

Design of Genes for Humanized XPA.04.001, XPA.04.013, XPA.04.018, XPA.04.048 Light and Heavy Chains The light chain and heavy chain variable region amino acid sequences for murine antibodies XPA.04.001, XPA.04.013, XPA.04.018, and XPA.04.048 are set forth in FIG. 7. The sequence of a human antibody identified using the National Biomedical Foundation Protein Identification Resource or similar database is used to provide the framework of the humanized antibody. To select the sequence of the humanized heavy chain, the murine heavy chain sequence is aligned with the sequence of the human antibody heavy chain. At each position, the human antibody amino acid is selected for the humanized sequence, unless that position falls in any one of four categories defined below, in which case the murine amino acid is selected:

(1) The position falls within a complementarity determining region (CDR), as defined by Kabat, J. Immunol., 125, 961-969 (1980);

(2) The human antibody amino acid is rare for human heavy chains at that position, whereas the murine amino acid is common for human heavy chains at that position;

(3) The position is immediately adjacent to a CDR in the amino acid sequence of the murine heavy chain; or (4) 3-dimensional modeling of the murine antibody suggests that the amino acid is physically close to the antigen binding region.

To select the sequence of the humanized light chain, the murine light chain sequence is aligned with the sequence of the human antibody light chain. The human antibody amino acid is selected at each position for the humanized sequence, unless the position again falls into one of the categories described above and repeated below:

(1) CDR's;

(2) murine amino acid more typical than human antibody;

(3) Adjacent to CDR's; or (4) Possible 3-dimensional proximity to binding region.

The actual nucleotide sequence of the heavy and light chain genes is selected as follows:

(1) The nucleotide sequences code for the amino acid sequences chosen as described above;

(2) 5' of these coding sequences, the nucleotide sequences code for a leader (signal) sequence. These leader sequences were chosen as typical of antibodies;

(3) 3' of the coding sequences, the nucleotide sequences are the sequences that follow the mouse light chain J5 segment and the mouse heavy chain J2 segment, which are part of the murine sequence. These sequences are included because they contain splice donor signals; and (4) At each end of the sequence is an Xba I site to allow cutting at the Xba I sites and cloning into the Xba I site of a vector.

Construction of Humanized Light and Heavy Chain Genes

To synthesize the heavy chain, four oligonucleotides are synthesized using an Applied Biosystems 380B DNA synthesizer. Two of the oligonucleotides are part of each strand of the heavy chain, and each oligonucleotide overlaps the next one by about 20 nucleotides to allow annealing. Together, the oligonucleotides cover the entire humanized heavy chain variable region with a few extra nucleotides at each end to allow cutting at the Xba I sites. The oligonucleotides are purified from polyacrylamide gels.

Each oligonucleotide is phosphorylated using ATP and T4 polynucleotide kinase by standard procedures (Maniatis et al., Molecular Cloning: A Laboratory Manual, 2nd ed., Cold Spring Harbor Laboratory, Cold Spring Harbor, N.Y. (1989)). To anneal the phosphorylated oligonucleotides, they are suspended together in 40 ul of TA (33 mM Tris acetate, pH 7.9, 66 mM potassium acetate, 10 mM magnesium acetate) at a concentration of about 3.75 µM each, heated to 95° C. for 4 min. and cooled slowly to 4° C. To synthesize the complete gene from the oligonucleotides by synthesizing the opposite strand of each oligonucleotide, the following components are added in a final volume of 100 ul:

| 10 ul | annealed oligonucleotides |
|---|---|
| 0.16 mM | each deoxyribonucleotide |
| 0.5 mM | ATP |
| 0.5 mM | DTT |
| 100 ug/ml | BSA |
| 3.5 ug/ml | T4 g43 protein (DNA polymerase) |
| 25 ug/ml | T4 g44/62 protein (polymerase accessory protein) |
| 25 ug/ml | 45 protein (polymerase accessory protein) |

The mixture is incubated at 37° C. for 30 min. Then 10 u of T4 DNA ligase is added and incubation at 37° C. is resumed for 30 min. The polymerase and ligase are inactivated by incubation of the reaction at 70° C. for 15 min. To digest the gene with Xba I, 50 ul of 2×TA containing BSA at 200 ug/ml and DTT at 1 mM, 43 ul of water, and 50 u of Xba I in 5 ul is added to the reaction. The reaction is incubated for 3 hr at 37° C., and then purified on a gel. The Xba I fragment is purified from a gel and cloned into the Xba I site of the plasmid pUC19 by standard methods. Plasmids are purified using standard techniques and sequenced using the dideoxy method.

Construction of plasmids to express humanized light and heavy chains is accomplished by isolating the light and heavy chain Xba I fragments from the pUC19 plasmid in which it had been inserted and then inserting it into the Xba I site of an appropriate expression vector which will express high levels of a complete heavy chain when transfected into an appropriate host cell.

Synthesis and Affinity of Humanized Antibody

The expression vectors are transfected into mouse Sp2/0 cells, and cells that integrate the plasmids are selected on the basis of the selectable marker(s) conferred by the expression vectors by standard methods. To verify that these cells secreted antibody that binds to EphB3, supernatant from the cells are incubated with cells that are known to express EphB3. After washing, the cells are incubated with fluorescein-conjugated goat anti-human antibody, washed, and analyzed for fluorescence on a FACSCAN cytofluorometer.

For the next experiments, cells producing the humanized antibody are injected into mice, and the resultant ascites is collected. Humanized antibody is purified to substantial homogeneity from the ascites by passage through an affinity column of goat anti-human immunoglobulin antibody, prepared on an Affigel-10 support (Bio-Rad Laboratories, Inc., Richmond, Calif.) according to standard techniques. The affinity of the humanized antibody relative to the original murine antibody is determined according to techniques known in the art.

Example 8

Human Engineering of Murine Antibodies

This example describes cloning and expression of Human Engineered™ antibodies, as well as purification of such antibodies and testing for binding activity.

Design of Human Engineered™ Sequences

Human Engineering™ of antibody variable domains has been described by Studnicka [See, e.g., Studnicka et al. U.S. Pat. No. 5,766,886; Studnicka et al. Protein Engineering 7: 805-814 (1994)] as a method for reducing immunogenicity while maintaining binding activity of antibody molecules. According to the method, each variable region amino acid has been assigned a risk of substitution. Amino acid substitutions are distinguished by one of three risk categories: (1) low risk changes are those that have the greatest potential for reducing immunogenicity with the least chance of disrupting antigen binding; (2) moderate risk changes are those that would further reduce immunogenicity, but have a greater chance of affecting antigen binding or protein folding; (3) high risk residues are those that are important for binding or for maintaining antibody structure and carry the highest risk that antigen binding or protein folding will be affected. Due to the three-dimensional structural role of prolines, modifications at prolines are generally considered to be at least moderate risk changes, even if the position is typically a low risk position. Subtitutional changes are preferred but insertions and deletions are also possible. FIG. 7 show the risk assignment for each amino acid residue of XPA.04.001, XPA.04.013, XPA.04.018, XPA.04.048 light and heavy chains, categorized as a high, moderate or low risk change.

Variable regions of the light and heavy chains of the murine antibody are Human Engineered™ using this method. Amino acid residues that are candidates for modification according to the method at low risk positions are identified by aligning the amino acid sequences of the murine variable regions with a human variable region sequence. Any human variable region can be used, including an individual VH or VL sequence or a human consensus VH or VL sequence. The amino acid residues at any number of the low risk positions, or at all of the low risk positions, can be changed.

Similarly, amino acid residues that are candidates for modification according to the method at all of the low and moderate risk positions are identified by aligning the amino acid sequences of the murine variable regions with a human variable region sequence. The amino acid residues at any number of the low or moderate risk positions, or at all of the low and moderate risk positions, can be changed.

Preparation of Expression Vectors for Permanent Cell Line Development

DNA fragments encoding each of the above-described heavy and light chain V region sequences along with antibody-derived signal sequences are constructed using synthetic nucleotide synthesis. DNA encoding each of the light chain V region amino acid sequences described above are inserted into vector pMXP10 containing the human Kappa light chain constant region. DNA encoding each of the heavy chain V region amino acid sequences described above are inserted into vector pMXP6 containing the human Gamma-1, 2, 3 or 4 heavy chain constant region. All of these vectors contain a hCMV promoter and a mouse kappa light chain 3' untranslated region as well as selectable marker genes such as neo or his for selection of G418—or histidinol—resistant transfectants, respectively.

Preparation of Expression Vectors for Transient Expression

Vectors containing either the light or heavy chain genes described above also are constructed for transient transfection. These vectors are similar to those described above for permanent transfections except that instead of the neo or his genes, they contain the Epstein-Barr virus oriP for replication in HEK293 cells that express the Epstein-Barr virus nuclear antigen.

Transient Expression of Human-Engineered Anti-EphB3 Antibody in HEK293E Cells

Separate vectors each containing oriP from the Epstein-Barr Virus and the light chain or heavy chain genes described above are transfected transiently into HEK293E cells. Transiently transfected cells are allowed to incubate for up to 10 days after which the supernatant is recovered and antibody purified using Protein A chromatography.

Development of Permanently Transfected CHO-K1 Cells

The vectors described above containing one copy each of the light and heavy genes together are transfected into Ex-Cell 302-adapted CHO-K1 cells. CHO-K1 cells adapted to suspension growth in Ex-Cell 302 medium are typically electroporated with 40 ug of linearized vector. Alternatively, linearized DNA can be complexed with linear polyethyleneimine (PEI) and used for transfection. The cells are plated in 96 well plates containing Ex-Cell 302 medium supplemented with 1% FBS and G418. Clones are screened in 96 well plates and the top ~10% of clones from each transfection are transferred to 24 well plates containing Ex-Cell 302 medium.

A productivity test is performed in 24 well plates in Ex-Cell 302 medium for cultures grown for 7 and 14 days at which time culture supernatants are tested for levels of secreted antibody by an immunoglobulin ELISA assay for IgG.

The top clones are transferred to shake flasks containing Ex-Cell 302 medium. As soon as the cells are adapted to suspension growth, a shake flask test is performed with these clones in Ex-Cell 302 medium. The cells are grown for up to 10 days in 125 ml Erlenmeyer flasks containing 25 ml media. The flasks are opened at least every other day of the incubation period to allow for gas exchange and the levels of immunoglobulin polypeptide in the culture medium are determined by IgG ELISA at the end of the incubation period. Multiple sequential transfections of the same cell line with two or three multi-unit transcription vectors results in clones and cell lines that exhibit further increases in levels of immunoglobulin production, preferably to 300 µg/ml or more.

Purification

A process for the purification of immunoglobulin polypeptides from vectors and all lines according to the invention may be designed. For example, according to methods well known in the art, cells are removed by filtration after termination. The filtrate is loaded onto a Protein A column (in multiple passes, if needed). The column is washed and then the expressed and secreted immunoglobulin polypeptides are eluted from the column. For preparation of antibody product, the Protein A pool is held at a low pH (pH 3 for a minimum of 30 minutes and a maximum of one hour) as a viral inactivation step. An adsorptive cation exchange step is next used to further purify the product. The eluate from the adsorptive separation column is passed through a virus retaining filter to provide further clearance of potential viral particles. The filtrate is further purified by passing through an anion exchange column in which the product does not bind. Finally, the purification process is concluded by transferring the product into the formulation buffer through diafiltration. The retentate is adjusted to a protein concentration of at least 1 mg/mL and a stabilizer is added.

Binding Activity

The EphB3 binding activity of the recombinant Human Engineered™ antibodies is evaluated. Protein is purified from shake flask culture supernatants by passage over a protein A column followed by concentration determination by $A_{280}$. Binding assays are performed as described in other examples.

Example 9

Effect of EphB3-Specific Antibodies In Vivo

To test for the effects of the anti-EphB3 antibodies on tumor growth in vivo, an orthotopic xenograft model is used in which a breast cancer cell line such as MDA-MB-231 or MDA-MB-435 is implanted in or near the mammary fat pads of female SCID-beige mice. The cancer cells (per mouse: $5 \times 10^6$ cells in 50-100 µl) are mixed with an equal volume of matrigel and either directly injected into a surgically exposed mammary fat pad, or injected subcutaneously above the mammary fat pad. The mice are returned to their cages, and tumor growth is monitored until a volume of approximately 100-150 mm$^3$ is reached. The mice are then randomized into treatment groups.

Treatments consist of intraperitoneal injections given twice per week of antibody or isotype control antibody. Doses used in the efficacy studies range from 0.2-20 mg/kg. Tumor volumes are measured 2-3 times per week, and efficacy is judged as the percent reduction in tumor volume in the agonist-treated mice vs. the control-treated mice.

All of the above U.S. patents, U.S. patent application publications, U.S. patent applications, foreign patents, foreign patent applications and non patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

What is claimed is:

1. An isolated antibody that binds the extracellular domain of EphB3, wherein the antibody comprises six CDR regions selected from the group consisting of:
   (a) CDR-L1, CDR-L2, CDR-L3, CDR-H1, CDR-H2 and CDR-H3 of antibody XPA.04.001, wherein the light chain variable region sequence of XPA.04.001 is set out in SEQ ID NO: 3 and the heavy chain variable sequence of XPA.04.001 is set out in SEQ ID NO: 4;
   (b) CDR-L1, CDR-L2, CDR-L3, CDR-H1, CDR-H2 and CDR-H3 of antibody XPA.04.013, wherein the light chain variable region sequence of XPA.04.013 is set out in SEQ ID NO: 5 and the heavy chain variable sequence of XPA.04.013 is set out in SEQ ID NO: 6;
   (c) CDR-L1, CDR-L2, CDR-L3, CDR-H1, CDR-H2 and CDR-H3 of antibody XPA.04.018, wherein the light chain variable region sequence of XPA.04.018 is set out in SEQ ID NO: 7 and the heavy chain variable sequence of XPA.04.018 is set out in SEQ ID NO: 8; and
   (d) CDR-L1, CDR-L2, CDR-L3, CDR-H1, CDR-H2 and CDR-H3 of antibody XPA.04.048, wherein the light chain variable region sequence of XPA.04.048 is set out in SEQ ID NO: 9 and the heavy chain variable sequence of XPA.04.048 is set out in SEQ ID NO: 10.

2. The antibody of claim 1 wherein the antibody is a chimeric antibody, a humanized antibody, a human engineered antibody, a human antibody, a single chain antibody or an antibody fragment.

3. The antibody of claim 1 that retains at least 90, 91, 92, 93, 94, 95, 96, 97, 98, or 99% identity over either the variable light or heavy region to the antibodies of XPA.04.001, XPA.04.013, XPA.04.018, or XPA.04.048.

4. The antibody of claim 1 that comprises a light chain constant region of a human antibody sequence, a heavy chain constant region of a human antibody sequence, and one or more heavy and light chain variable framework regions of a human antibody sequence.

5. The antibody of claim 4 wherein the human antibody sequence is an individual human sequence, a human consensus sequence, an individual human germline sequence, or a human consensus germline sequence.

6. The antibody of claim 4 wherein the heavy chain constant region is a modified or unmodified IgG, IgM, IgA, IgD, IgE, a fragment thereof, or combinations thereof.

7. The antibody of claim 1 that has a binding affinity of $10^{-7}$, $10^{-8}$ or $10^{-9}$ M or less to EphB3.

8. The antibody of claim 4 wherein the light chain constant region is a modified or unmodified lambda light chain constant region, a kappa light chain constant region, a fragment thereof, or combinations thereof.

9. The antibody of claim 1 that induces EphB3 phosphorylation.

10. The antibody of claim 1 that induces EphB3 oligomerization.

11. The antibody of claim 1 that induces EphB3 internalization.

12. The antibody of claim 1 that induces EphB3 degradation.

13. The antibody of claim 1 that induces EphB3 signaling.

14. The antibody of claim 1 that inhibits the binding of an ephrinB to EphB3.

15. The antibody of claim 1 that is conjugated to another diagnostic or therapeutic agent.

16. The antibody of claim 1 that is purified to at least 95% homogeneity by weight.

17. A pharmaceutical composition comprising the antibody of claim 16 and a pharmaceutically acceptable carrier.

18. A kit comprising an antibody of claim 1, packaged in a container, said kit optionally containing a second therapeutic agent, and further comprising a label attached to or packaged with the container, the label describing the contents of the container and providing indications and/or instructions regarding use of the contents of the container.

19. The kit of claim 18 wherein the container is a vial or bottle or prefilled syringe.

20. The antibody of claim 2 wherein said antibody induces an activity selected from the group consisting of: (a) Eph3 phosphorylation; (b) EphB3 oligomerization; (c) EphB3 internalization; (d) EphB3 degradation; and (e) EphB3 signaling.

* * * * *

UNITED STATES PATENT AND TRADEMARK OFFICE
CERTIFICATE OF CORRECTION

PATENT NO. : 8,586,716 B2  
APPLICATION NO. : 11/833726  
DATED : November 19, 2013  
INVENTOR(S) : Hsu et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1215 days.

Signed and Sealed this
Thirty-first Day of March, 2015

Michelle K. Lee
*Director of the United States Patent and Trademark Office*

UNITED STATES PATENT AND TRADEMARK OFFICE
CERTIFICATE OF CORRECTION

PATENT NO.       : 8,586,716 B2
APPLICATION NO.  : 11/833726
DATED            : November 19, 2013
INVENTOR(S)      : Jeff Hsu et al.

Page 1 of 1

It is certified that error appears in the above-identified patent and that said Letters Patent is hereby corrected as shown below:

In the Claims:

At Column 214, line 57, Claim 20, "Eph3" should be -- EphB3 --.

Signed and Sealed this
Twenty-fifth Day of August, 2015

Michelle K. Lee
*Director of the United States Patent and Trademark Office*

SEQUENCE LISTING

```
<160> NUMBER OF SEQ ID NOS: 429

<210> SEQ ID NO 1
<211> LENGTH: 4234
<212> TYPE: DNA
<213> ORGANISM: Homo sapiens

<400> SEQUENCE: 1
cgtgagcggc gcagcaagat cccagctcgg accccggacg gcgcgcgccc ccgaagcccc        60
ggatcccagt cgggcccgca gctgaccgcc agattactgt gcatcccgaa tcacgaccac       120
ctgcaccctc ctgccccggc ccgccccca agtcctcagg cacccagctc ccggcgcc         180 cggatcctcc tggaccggtc cgtccagatt cccgcgggac cgacctgtcc gcatccccag       240
gaccgccggg ctcggtgcac cgcctcggtc ccggagccgc ccgcctggat tgcattccct       300
cctctcctgg atctcctggg acccgacgcg agcctgcccc ggagcccgcc gagcgcaccc       360
tctctcgggt gcctgcagcc ccgccggcgc ggcccggccc ggcgcggccc ggctcggctc       420
ctagagctgc cacggccatg gccagagccc gcccgccgcc gccgccgtcg ccgccgccgg       480
ggcttctgcc gctgctccct ccgctgctgc tgctgccgct gctgctgctg cccgccggct       540
gccgggcgct ggaagagacc ctcatggaca caaaatgggt aacatctgag ttggcgtgga       600
catctcatcc agaaagtggg tgggaagagg tgagtggcta cgatgaggcc atgaatccca       660
```

```
tccgcacata ccaggtgtgt aatgtgcgcg agtcaagcca gaacaactgg cttcgcacgg    720
ggttcatctg gcggcgggat gtgcagcggg tctacgtgga gctcaagttc actgtgcgtg    780
actgcaacag catccccaac atccccggct cctgcaagga gaccttcaac ctcttctact    840
acgaggctga cagcgatgtg gcctcagcct cctcccccctt ctggatggag aaccoctacg    900 tgaaagtgga caccattgca cccgatgaga gcttctcgcg gctggatgcc ggccgtgtca    960
acaccaaggt gcgcagcttt gggccacttt ccaaggctgg cttctacctg gccttccagg   1020
accagggcgc ctgcatgtcg ctcatctccg tgcgcgcctt ctacaagaag tgtgcatcca   1080
ccaccgcagg cttcgcactc ttccccgaga ccctcactgg ggcggagccc acctcgctgg   1140
tcattgctcc tggcacctgc atccctaacg ccgtggaggt gtcggtgcca ctcaagctct   1200
actgcaacgg cgatggggag tggatggtgc ctgtgggtgc ctgcacctgt gccaccggcc   1260
atgagccagc tgccaaggag tcccagtgcc gcccctgtcc ccctgggagc tacaaggcga   1320
agcagggaga ggggccctgc ctcccatgtc cccccaacag ccgtaccacc tccccagccg   1380
ccagcatctg cacctgccac aataacttct accgtgcaga ctcggactct gcggacagtg   1440
cctgtaccac cgtgccatct ccaccccgag gtgtgatctc caatgtgaat gaaacctcac   1500
tgatcctcga gtggagtgag ccccgggacc tgggtggccg ggatgacctc ctgtacaatg   1560
tcatctgcaa gaagtgccat ggggctggag gggcctcagc ctgctcacgc tgtgatgaca   1620
acgtggagtt tgtgcctcgg cagctgggcc tgacggagcg ccgggtccac atcagccatc   1680
tgctggccca cacgcgctac acctttgagg tgcaggcggt caacggtgtc tcgggcaaga   1740
gccctctgcc gcctcgttat gcggccgtga atatcaccac aaaccaggct gccccgtctg   1800
aagtgcccac actacgcctg cacagcagct caggcagcag cctcaccctg tcctgggcac   1860
ccccagagcg gcccaacgga gtcatcctgg actacgagat gaagtacttt gagaagagcg   1920
agggcatcgc ctccacagtg accagccaga tgaactccgt gcagctggac gggcttcggc   1980
ctgacgcccg ctatgtggtc caggtccgtg cccgcacagt agctggctat gggcagtaca   2040
gccgccctgc cgagtttgag accacaagtg agagaggctc tggggcccag cagctccagg   2100
agcagcttcc cctcatcgtg ggctccgcta cagctgggct tgtcttcgtg gtggctgtcg   2160
tggtcatcgc tatcgtctgc ctcaggaagc agcgacacgg ctctgattcg gagtacacgg   2220
agaagctgca gcagtacatt gctcctggaa tgaaggttta tattgacccct tttacctacg   2280 aggaccctaa tgaggctgtt cgggagtttg ccaaggagat cgacgtgtcc tgcgtcaaga   2340
tcgaggaggt gatcggagct ggggaatttg ggaagtgtgg ccgtggtcga ctgaaacagc   2400
ctggccgccg agaggtgttt gtggccatca gacgctgaag gtgggctac accgagaggc   2460 agcggcggga cttcctaagc gaggcctcca tcatgggtca gtttgatcac cccaatataa   2520
tccggctcga gggcgtggtc accaaaagtc ggccagttat gatcctcact gagttcatgg   2580
aaaactgcgc cctggactcc ttcctccggc tcaacgatgg gcagttcacg gtcatccagc   2640
tggtgggcat gttgcggggc attgctgccg gcatgaagta cctgtccgag atgaactatg   2700
tgcaccgcga cctggctgct cgcaacatcc ttgtcaacag caacctggtc tgcaaagtct   2760
cagactttgg cctctcccgc ttcctggagg atgacccctc cgatcctacc tacaccagtt   2820
ccctgggcgg aagatccccc atccgctgga ctgcccagga ggccatagcc tatcggaagt   2880
tcacttctgc tagtgatgtc tggagctacg gaattgtcat gtgggaggtc atgagctatg   2940
gagagcgacc ctactgggac atgagcaacc aggatgtcat caatgccgtg gagcaggatt   3000
accggctgcc accacccatg gactgtccca gcagcactgca ccagctcatg ctggactgct   3060
```

```
gggtgcggga ccggaacctc aggcccaaat tctcccagat tgtcaatacc ctggacaagc   3120
tcatccgcaa tgctgccagc ctcaaggtca ttgccagcgc tcagtctggc atgtcacagc   3180
ccctcctgga ccgcacggtc ccagattaca caaccttcac gacagttggt gattggctgg   3240
atgccatcaa gatggggcgg tacaaggaga gcttcgtcag tgcggggttt gcatcttttg   3300
acctggtggc ccagatgacg gcagaagacc tgctccgtat tggggtcacc ctggccggcc   3360
accagaagaa gatcctgagc agtatccagg acatgcggct gcagatgaac agacgctgc    3420 ctgtgcaggt ctgacaccgg ctcccacggg gaccctgagg accgtgcagg gatgccaagc   3480
agccggctgg actttcggac tcttggactt ttggatgcct ggccttaggc tgtggcccag   3540
aagctggaag tttgggaaag gcccaagctg ggacttctcc aggcctgtgt tccctcccca   3600
ggaagtgcgc cccaaacctc ttcatattga agatggatta ggagaggggg tgatgacccc   3660
tccccaagcc cctcagggcc cagaccttcc tgctctccag caggggatcc ccacaacctc   3720
acacttgtct gttcttcagt gctggaggtc ctggcagggt caggctgggg taagccgggg   3780
ttccacaggg cccagccctg cagggggtct ggcccccag gtaggcggag agcagtccct    3840
ccctcaggaa ctgaggagg ggactccagg aatggggaaa tgtgacacca ccatcctgaa    3900
gccagcttgc acctccagtt tgcacaggga tttgttctgg gggctgaggg ccctgtcccc   3960 accccgccc ttggtgctgt cataaaaggg caggcagggg caggctgagg agttgccctt    4020 tgcccccag agactgactc tcagagccag agatgggatg tgtgagtgtg tgtgtgtgtg    4080
tgtgtgtgtg cgcgcgcgcg cgcgtgtgtg tgtgcacgca ctggcctgca cagagagcat   4140
gggtgagcgt gtaaaagctt ggccctgtgc cctacaatgg ggccagctgg gccgacagca   4200
gaataaaggc aataagatga aaaaaaaaaa aaaa                               4234

<210> SEQ ID NO 2
<211> LENGTH: 998
<212> TYPE: PRT
<213> ORGANISM: Homo sapiens

<400> SEQUENCE: 2

Met Ala Arg Ala Arg Pro Pro Pro Pro Ser Pro Pro Pro Gly Leu
1               5                   10                  15

Leu Pro Leu Leu Pro Pro Leu Leu Leu Pro Leu Leu Leu Leu Pro
                20                  25                  30

Ala Gly Cys Arg Ala Leu Glu Glu Thr Leu Met Asp Thr Lys Trp Val
            35                  40                  45

Thr Ser Glu Leu Ala Trp Thr Ser His Pro Glu Ser Gly Trp Glu Glu
        50                  55                  60

Val Ser Gly Tyr Asp Glu Ala Met Asn Pro Ile Arg Thr Tyr Gln Val
65                  70                  75                  80

Cys Asn Val Arg Glu Ser Ser Gln Asn Asn Trp Leu Arg Thr Gly Phe
                85                  90                  95

Ile Trp Arg Arg Asp Val Gln Arg Val Tyr Val Glu Leu Lys Phe Thr
            100                 105                 110

Val Arg Asp Cys Asn Ser Ile Pro Asn Ile Pro Gly Ser Cys Lys Glu
        115                 120                 125

Thr Phe Asn Leu Phe Tyr Tyr Glu Ala Asp Ser Asp Val Ala Ser Ala
    130                 135                 140

Ser Ser Pro Phe Trp Met Glu Asn Pro Tyr Val Lys Val Asp Thr Ile
145                 150                 155                 160

Ala Pro Asp Glu Ser Phe Ser Arg Leu Asp Ala Gly Arg Val Asn Thr
                165                 170                 175
```

-continued

```
Lys Val Arg Ser Phe Gly Pro Leu Ser Lys Ala Gly Phe Tyr Leu Ala
            180                 185                 190
Phe Gln Asp Gln Gly Ala Cys Met Ser Leu Ile Ser Val Arg Ala Phe
            195                 200                 205
Tyr Lys Lys Cys Ala Ser Thr Thr Ala Gly Phe Ala Leu Phe Pro Glu
210                 215                 220
Thr Leu Thr Gly Ala Glu Pro Thr Ser Leu Val Ile Ala Pro Gly Thr
225                 230                 235                 240
Cys Ile Pro Asn Ala Val Glu Val Ser Val Pro Leu Lys Leu Tyr Cys
            245                 250                 255
Asn Gly Asp Gly Glu Trp Met Val Pro Val Gly Ala Cys Thr Cys Ala
            260                 265                 270
Thr Gly His Glu Pro Ala Ala Lys Glu Ser Gln Cys Arg Pro Cys Pro
            275                 280                 285
Pro Gly Ser Tyr Lys Ala Lys Gln Gly Glu Gly Pro Cys Leu Pro Cys
            290                 295                 300
Pro Pro Asn Ser Arg Thr Thr Ser Pro Ala Ala Ser Ile Cys Thr Cys
305                 310                 315                 320
His Asn Asn Phe Tyr Arg Ala Asp Ser Asp Ser Ala Asp Ser Ala Cys
            325                 330                 335
Thr Thr Val Pro Ser Pro Pro Arg Gly Val Ile Ser Asn Val Asn Glu
            340                 345                 350
Thr Ser Leu Ile Leu Glu Trp Ser Glu Pro Arg Asp Leu Gly Gly Arg
            355                 360                 365
Asp Asp Leu Leu Tyr Asn Val Ile Cys Lys Lys Cys His Gly Ala Gly
            370                 375                 380
Gly Ala Ser Ala Cys Ser Arg Cys Asp Asp Asn Val Glu Phe Val Pro
385                 390                 395                 400
Arg Gln Leu Gly Leu Thr Glu Arg Arg Val His Ile Ser His Leu Leu
            405                 410                 415
Ala His Thr Arg Tyr Thr Phe Glu Val Gln Ala Val Asn Gly Val Ser
            420                 425                 430
Gly Lys Ser Pro Leu Pro Pro Arg Tyr Ala Ala Val Asn Ile Thr Thr
            435                 440                 445
Asn Gln Ala Ala Pro Ser Glu Val Pro Thr Leu Arg Leu His Ser Ser
450                 455                 460
Ser Gly Ser Ser Leu Thr Leu Ser Trp Ala Pro Pro Glu Arg Pro Asn
465                 470                 475                 480
Gly Val Ile Leu Asp Tyr Glu Met Lys Tyr Phe Glu Lys Ser Glu Gly
            485                 490                 495
Ile Ala Ser Thr Val Thr Ser Gln Met Asn Ser Val Gln Leu Asp Gly
            500                 505                 510
Leu Arg Pro Asp Ala Arg Tyr Val Val Gln Val Arg Ala Arg Thr Val
            515                 520                 525
Ala Gly Tyr Gly Gln Tyr Ser Arg Pro Ala Glu Phe Glu Thr Thr Ser
530                 535                 540
Glu Arg Gly Ser Gly Ala Gln Gln Leu Gln Glu Gln Leu Pro Leu Ile
545                 550                 555                 560
Val Gly Ser Ala Thr Ala Gly Leu Val Phe Val Ala Val Val Val Val
            565                 570                 575
Ile Ala Ile Val Cys Leu Arg Lys Gln Arg His Gly Ser Asp Ser Glu
            580                 585                 590
Tyr Thr Glu Lys Leu Gln Gln Tyr Ile Ala Pro Gly Met Lys Val Tyr
```

```
                595                 600                 605
Ile Asp Pro Phe Thr Tyr Glu Asp Pro Asn Glu Ala Val Arg Glu Phe
610                 615                 620

Ala Lys Glu Ile Asp Val Ser Cys Val Lys Ile Glu Glu Val Ile Gly
625                 630                 635                 640

Ala Gly Glu Phe Gly Glu Val Cys Arg Gly Arg Leu Lys Gln Pro Gly
                645                 650                 655

Arg Arg Glu Val Phe Val Ala Ile Lys Thr Leu Lys Val Gly Tyr Thr
                660                 665                 670

Glu Arg Gln Arg Arg Asp Phe Leu Ser Glu Ala Ser Ile Met Gly Gln
                675                 680                 685

Phe Asp His Pro Asn Ile Ile Arg Leu Glu Gly Val Val Thr Lys Ser
690                 695                 700

Arg Pro Val Met Ile Leu Thr Glu Phe Met Glu Asn Cys Ala Leu Asp
705                 710                 715                 720

Ser Phe Leu Arg Leu Asn Asp Gly Gln Phe Thr Val Ile Gln Leu Val
                725                 730                 735

Gly Met Leu Arg Gly Ile Ala Ala Gly Met Lys Tyr Leu Ser Glu Met
                740                 745                 750

Asn Tyr Val His Arg Asp Leu Ala Ala Arg Asn Ile Leu Val Asn Ser
                755                 760                 765

Asn Leu Val Cys Lys Val Ser Asp Phe Gly Leu Ser Arg Phe Leu Glu
                770                 775                 780

Asp Asp Pro Ser Asp Pro Thr Tyr Thr Ser Ser Leu Gly Gly Lys Ile
785                 790                 795                 800

Pro Ile Arg Trp Thr Ala Pro Glu Ala Ile Ala Tyr Arg Lys Phe Thr
                805                 810                 815

Ser Ala Ser Asp Val Trp Ser Tyr Gly Ile Val Met Trp Glu Val Met
                820                 825                 830

Ser Tyr Gly Glu Arg Pro Tyr Trp Asp Met Ser Asn Gln Asp Val Ile
                835                 840                 845

Asn Ala Val Glu Gln Asp Tyr Arg Leu Pro Pro Met Asp Cys Pro
850                 855                 860

Thr Ala Leu His Gln Leu Met Leu Asp Cys Trp Val Arg Asp Arg Asn
865                 870                 875                 880

Leu Arg Pro Lys Phe Ser Gln Ile Val Asn Thr Leu Asp Lys Leu Ile
                885                 890                 895

Arg Asn Ala Ala Ser Leu Lys Val Ile Ala Ser Ala Gln Ser Gly Met
                900                 905                 910

Ser Gln Pro Leu Leu Asp Arg Thr Val Pro Asp Tyr Thr Thr Phe Thr
                915                 920                 925

Thr Val Gly Asp Trp Leu Asp Ala Ile Lys Met Gly Arg Tyr Lys Glu
930                 935                 940

Ser Phe Val Ser Ala Gly Phe Ala Ser Phe Asp Leu Val Ala Gln Met
945                 950                 955                 960

Thr Ala Glu Asp Leu Leu Arg Ile Gly Val Thr Leu Ala Gly His Gln
                965                 970                 975

Lys Lys Ile Leu Ser Ser Ile Gln Asp Met Arg Leu Gln Met Asn Gln
                980                 985                 990

Thr Leu Pro Val Gln Val
                995

<210> SEQ ID NO 3
<211> LENGTH: 113
```

```
<212> TYPE: PRT
<213> ORGANISM: Homo sapiens

<400> SEQUENCE: 3

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gly Gly Thr Lys Leu Glu Leu Lys
            100                 105                 110

Arg

<210> SEQ ID NO 4
<211> LENGTH: 113
<212> TYPE: PRT
<213> ORGANISM: Homo sapiens

<400> SEQUENCE: 4

Gln Val Gln Leu Gln Gln Ser Gly Ala Glu Leu Val Met Pro Gly Ala
1               5                   10                  15

Ser Val Lys Leu Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Gly Ala Glu Tyr Trp Gly Gln Gly Thr Thr Leu Thr Val Ser
            100                 105                 110

Ser

<210> SEQ ID NO 5
<211> LENGTH: 113
<212> TYPE: PRT
<213> ORGANISM: Homo sapiens

<400> SEQUENCE: 5

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
```

```
                65                  70                  75                  80
        Ser Arg Val Glu Ala Glu Asp Val Gly Val Tyr Tyr Cys Met Gln His
                        85                  90                  95

Leu Glu Tyr Pro Leu Thr Phe Gly Ala Gly Thr Lys Leu Glu Leu Lys
                        100                 105                 110

Arg

<210> SEQ ID NO 6
<211> LENGTH: 114
<212> TYPE: PRT
<213> ORGANISM: Homo sapiens

<400> SEQUENCE: 6

Gln Val Gln Leu Gln Gln Pro Gly Pro Asp Leu Val Met Pro Gly Ala
        1               5                   10                  15

Ser Val Lys Leu Ser Cys Lys Ala Ser Gly Tyr Thr Phe Thr Asn Tyr
                        20                  25                  30

Tyr Ile His Trp Val Lys Gln Arg Pro Gly Gln Gly Leu Glu Trp Ile
                        35                  40                  45

Gly Gln Ile Asp Pro Ser Asp Ser Thr Asp Tyr Asn Gln Lys Phe
                50                  55                  60

Lys Gly Lys Ala Thr Leu Thr Val Asp Lys Ser Ser Thr Ala Phe
        65                      70                  75                  80

Met Gln Leu Ser Ser Leu Thr Ser Glu Asp Ser Ala Val Tyr Phe Cys
                        85                  90                  95

Ala Arg Ser Ser Thr Gly Pro Trp Gly Gln Gly Thr Thr Leu Thr Val
                        100                 105                 110

Ser Ser

<210> SEQ ID NO 7
<211> LENGTH: 113
<212> TYPE: PRT
<213> ORGANISM: Homo sapiens

<400> SEQUENCE: 7

Asp Ile Val Met Thr Gln Ala Ala Pro Ser Val Pro Val Thr Pro Gly
        1               5                   10                  15

Glu Ser Val Ser Ile Pro Cys Arg Ser Ser Lys Ser Leu Leu His Ser
                        20                  25                  30

Asn Gly Asn Thr Tyr Leu Tyr Trp Phe Leu Gln Arg Pro Gly Gln Ser
                        35                  40                  45

Pro Gln Leu Leu Ile Tyr Arg Met Ser Asn Leu Ala Ser Gly Val Pro
                50                  55                  60

Asp Arg Phe Ser Gly Ser Gly Ser Gly Thr Asp Phe Thr Leu Arg Ile
        65                      70                  75                  80

Gly Arg Val Glu Ala Glu Asp Val Gly Val Tyr Tyr Cys Met Gln His
                        85                  90                  95

Leu Glu Tyr Pro Leu Thr Phe Gly Ala Gly Thr Lys Leu Glu Leu Lys
                        100                 105                 110

Arg

<210> SEQ ID NO 8
<211> LENGTH: 113
<212> TYPE: PRT
<213> ORGANISM: Homo sapiens

<400> SEQUENCE: 8
```

```
Gln Val Gln Leu Gln Gln Pro Gly Ala Glu Leu Val Met Pro Gly Ala
1               5                   10                  15

Ser Met Lys Leu Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
            35                  40                  45

Gly Glu Ile Asp Pro Ser Asp Phe Tyr Thr Asn Tyr Asn Gln Lys Phe
        50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Ile Ser Ser Trp Gly Gln Gly Thr Thr Leu Thr Val Ser
            100                 105                 110

Ser
```

<210> SEQ ID NO 9
<211> LENGTH: 113
<212> TYPE: PRT
<213> ORGANISM: Homo sapiens

<400> SEQUENCE: 9

```
Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
            35                  40                  45

Leu Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110

Arg
```

<210> SEQ ID NO 10
<211> LENGTH: 113
<212> TYPE: PRT
<213> ORGANISM: Homo sapiens

<400> SEQUENCE: 10

```
Glu Val Gln Leu Gln Gln Ser Gly Ala Glu Leu Val Met Pro Gly Ala
1               5                   10                  15

Ser Val Lys Leu Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
            35                  40                  45

Gly Glu Ile Asp Pro Ser Asp Ser Tyr Thr Asn Tyr Asn Gln Lys Phe
        50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95
```

```
Thr Arg Gly Ile Thr Asn Trp Gly Gln Gly Thr Thr Leu Thr Val Ser
                100                 105                 110
Ser

<210> SEQ ID NO 11
<211> LENGTH: 8
<212> TYPE: PRT
<213> ORGANISM: Homo sapiens

<400> SEQUENCE: 11

Trp Arg Arg Asp Val Gln Arg Val
1               5

<210> SEQ ID NO 12
<211> LENGTH: 8
<212> TYPE: PRT
<213> ORGANISM: Homo sapiens

<400> SEQUENCE: 12

Arg Arg Asp Val Gln Arg Val Tyr
1               5

<210> SEQ ID NO 13
<211> LENGTH: 8
<212> TYPE: PRT
<213> ORGANISM: Homo sapiens

<400> SEQUENCE: 13

Arg Asp Val Gln Arg Val Tyr Val
1               5

<210> SEQ ID NO 14
<211> LENGTH: 8
<212> TYPE: PRT
<213> ORGANISM: Homo sapiens

<400> SEQUENCE: 14

Asp Val Gln Arg Val Tyr Val Glu
1               5

<210> SEQ ID NO 15
<211> LENGTH: 8
<212> TYPE: PRT
<213> ORGANISM: Homo sapiens

<400> SEQUENCE: 15

Val Gln Arg Val Tyr Val Glu Leu
1               5

<210> SEQ ID NO 16
<211> LENGTH: 8
<212> TYPE: PRT
<213> ORGANISM: Homo sapiens

<400> SEQUENCE: 16

Gln Arg Val Tyr Val Glu Leu Lys
1               5

<210> SEQ ID NO 17
<211> LENGTH: 8
<212> TYPE: PRT
<213> ORGANISM: Homo sapiens

<400> SEQUENCE: 17

Arg Val Tyr Val Glu Leu Lys Phe
```

<210> SEQ ID NO 18
<211> LENGTH: 8
<212> TYPE: PRT
<213> ORGANISM: Homo sapiens

<400> SEQUENCE: 18

Val Tyr Val Glu Leu Lys Phe Thr
1               5

<210> SEQ ID NO 19
<211> LENGTH: 8
<212> TYPE: PRT
<213> ORGANISM: Homo sapiens

<400> SEQUENCE: 19

Tyr Val Glu Leu Lys Phe Thr Val
1               5

<210> SEQ ID NO 20
<211> LENGTH: 8
<212> TYPE: PRT
<213> ORGANISM: Homo sapiens

<400> SEQUENCE: 20

Val Glu Leu Lys Phe Thr Val Arg
1               5

<210> SEQ ID NO 21
<211> LENGTH: 8
<212> TYPE: PRT
<213> ORGANISM: Homo sapiens

<400> SEQUENCE: 21

Glu Leu Lys Phe Thr Val Arg Asp
1               5

<210> SEQ ID NO 22
<211> LENGTH: 9
<212> TYPE: PRT
<213> ORGANISM: Homo sapiens

<400> SEQUENCE: 22

Trp Arg Arg Asp Val Gln Arg Val Tyr
1               5

<210> SEQ ID NO 23
<211> LENGTH: 9
<212> TYPE: PRT
<213> ORGANISM: Homo sapiens

<400> SEQUENCE: 23

Arg Arg Asp Val Gln Arg Val Tyr Val
1               5

<210> SEQ ID NO 24
<211> LENGTH: 9
<212> TYPE: PRT
<213> ORGANISM: Homo sapiens

<400> SEQUENCE: 24

Arg Asp Val Gln Arg Val Tyr Val Glu
1               5

```
<210> SEQ ID NO 25
<211> LENGTH: 9
<212> TYPE: PRT
<213> ORGANISM: Homo sapiens

<400> SEQUENCE: 25

Asp Val Gln Arg Val Tyr Val Glu Leu
1               5

<210> SEQ ID NO 26
<211> LENGTH: 9
<212> TYPE: PRT
<213> ORGANISM: Homo sapiens

<400> SEQUENCE: 26

Val Gln Arg Val Tyr Val Glu Leu Lys
1               5

<210> SEQ ID NO 27
<211> LENGTH: 9
<212> TYPE: PRT
<213> ORGANISM: Homo sapiens

<400> SEQUENCE: 27

Gln Arg Val Tyr Val Glu Leu Lys Phe
1               5

<210> SEQ ID NO 28
<211> LENGTH: 9
<212> TYPE: PRT
<213> ORGANISM: Homo sapiens

<400> SEQUENCE: 28

Arg Val Tyr Val Glu Leu Lys Phe Thr
1               5

<210> SEQ ID NO 29
<211> LENGTH: 9
<212> TYPE: PRT
<213> ORGANISM: Homo sapiens

<400> SEQUENCE: 29

Val Tyr Val Glu Leu Lys Phe Thr Val
1               5

<210> SEQ ID NO 30
<211> LENGTH: 9
<212> TYPE: PRT
<213> ORGANISM: Homo sapiens

<400> SEQUENCE: 30

Tyr Val Glu Leu Lys Phe Thr Val Arg
1               5

<210> SEQ ID NO 31
<211> LENGTH: 9
<212> TYPE: PRT
<213> ORGANISM: Homo sapiens

<400> SEQUENCE: 31

Val Glu Leu Lys Phe Thr Val Arg Asp
1               5

<210> SEQ ID NO 32
<211> LENGTH: 10
<212> TYPE: PRT
```

<213> ORGANISM: Homo sapiens

<400> SEQUENCE: 32

Trp Arg Arg Asp Val Gln Arg Val Tyr Val
1               5                   10

<210> SEQ ID NO 33
<211> LENGTH: 10
<212> TYPE: PRT
<213> ORGANISM: Homo sapiens

<400> SEQUENCE: 33

Arg Arg Asp Val Gln Arg Val Tyr Val Glu
1               5                   10

<210> SEQ ID NO 34
<211> LENGTH: 10
<212> TYPE: PRT
<213> ORGANISM: Homo sapiens

<400> SEQUENCE: 34

Arg Asp Val Gln Arg Val Tyr Val Glu Leu
1               5                   10

<210> SEQ ID NO 35
<211> LENGTH: 10
<212> TYPE: PRT
<213> ORGANISM: Homo sapiens

<400> SEQUENCE: 35

Asp Val Gln Arg Val Tyr Val Glu Leu Lys
1               5                   10

<210> SEQ ID NO 36
<211> LENGTH: 10
<212> TYPE: PRT
<213> ORGANISM: Homo sapiens

<400> SEQUENCE: 36

Val Gln Arg Val Tyr Val Glu Leu Lys Phe
1               5                   10

<210> SEQ ID NO 37
<211> LENGTH: 10
<212> TYPE: PRT
<213> ORGANISM: Homo sapiens

<400> SEQUENCE: 37

Gln Arg Val Tyr Val Glu Leu Lys Phe Thr
1               5                   10

<210> SEQ ID NO 38
<211> LENGTH: 10
<212> TYPE: PRT
<213> ORGANISM: Homo sapiens

<400> SEQUENCE: 38

Arg Val Tyr Val Glu Leu Lys Phe Thr Val
1               5                   10

<210> SEQ ID NO 39
<211> LENGTH: 10
<212> TYPE: PRT
<213> ORGANISM: Homo sapiens

<400> SEQUENCE: 39

Val Tyr Val Glu Leu Lys Phe Thr Val Arg
1               5                   10

<210> SEQ ID NO 40
<211> LENGTH: 10
<212> TYPE: PRT
<213> ORGANISM: Homo sapiens

<400> SEQUENCE: 40

Tyr Val Glu Leu Lys Phe Thr Val Arg Asp
1               5                   10

<210> SEQ ID NO 41
<211> LENGTH: 8
<212> TYPE: PRT
<213> ORGANISM: Homo sapiens

<400> SEQUENCE: 41

Asn Pro Tyr Val Lys Val Asp Thr
1               5

<210> SEQ ID NO 42
<211> LENGTH: 8
<212> TYPE: PRT
<213> ORGANISM: Homo sapiens

<400> SEQUENCE: 42

Pro Tyr Val Lys Val Asp Thr Ile
1               5

<210> SEQ ID NO 43
<211> LENGTH: 8
<212> TYPE: PRT
<213> ORGANISM: Homo sapiens

<400> SEQUENCE: 43

Tyr Val Lys Val Asp Thr Ile Ala
1               5

<210> SEQ ID NO 44
<211> LENGTH: 8
<212> TYPE: PRT
<213> ORGANISM: Homo sapiens

<400> SEQUENCE: 44

Val Lys Val Asp Thr Ile Ala Pro
1               5

<210> SEQ ID NO 45
<211> LENGTH: 8
<212> TYPE: PRT
<213> ORGANISM: Homo sapiens

<400> SEQUENCE: 45

Lys Val Asp Thr Ile Ala Pro Asp
1               5

<210> SEQ ID NO 46
<211> LENGTH: 8
<212> TYPE: PRT
<213> ORGANISM: Homo sapiens

<400> SEQUENCE: 46

Val Asp Thr Ile Ala Pro Asp Glu
1               5

<210> SEQ ID NO 47
<211> LENGTH: 8
<212> TYPE: PRT
<213> ORGANISM: Homo sapiens

<400> SEQUENCE: 47

Asp Thr Ile Ala Pro Asp Glu Ser
1               5

<210> SEQ ID NO 48
<211> LENGTH: 8
<212> TYPE: PRT
<213> ORGANISM: Homo sapiens

<400> SEQUENCE: 48

Thr Ile Ala Pro Asp Glu Ser Phe
1               5

<210> SEQ ID NO 49
<211> LENGTH: 8
<212> TYPE: PRT
<213> ORGANISM: Homo sapiens

<400> SEQUENCE: 49

Ile Ala Pro Asp Glu Ser Phe Ser
1               5

<210> SEQ ID NO 50
<211> LENGTH: 8
<212> TYPE: PRT
<213> ORGANISM: Homo sapiens

<400> SEQUENCE: 50

Ala Pro Asp Glu Ser Phe Ser Arg
1               5

<210> SEQ ID NO 51
<211> LENGTH: 8
<212> TYPE: PRT
<213> ORGANISM: Homo sapiens

<400> SEQUENCE: 51

Pro Asp Glu Ser Phe Ser Arg Leu
1               5

<210> SEQ ID NO 52
<211> LENGTH: 8
<212> TYPE: PRT
<213> ORGANISM: Homo sapiens

<400> SEQUENCE: 52

Asp Glu Ser Phe Ser Arg Leu Asp
1               5

<210> SEQ ID NO 53
<211> LENGTH: 8
<212> TYPE: PRT
<213> ORGANISM: Homo sapiens

<400> SEQUENCE: 53

Glu Ser Phe Ser Arg Leu Asp Ala
1               5

<210> SEQ ID NO 54

```
<211> LENGTH: 8
<212> TYPE: PRT
<213> ORGANISM: Homo sapiens

<400> SEQUENCE: 54

Ser Phe Ser Arg Leu Asp Ala Gly
1               5

<210> SEQ ID NO 55
<211> LENGTH: 8
<212> TYPE: PRT
<213> ORGANISM: Homo sapiens

<400> SEQUENCE: 55

Phe Ser Arg Leu Asp Ala Gly Arg
1               5

<210> SEQ ID NO 56
<211> LENGTH: 8
<212> TYPE: PRT
<213> ORGANISM: Homo sapiens

<400> SEQUENCE: 56

Ser Arg Leu Asp Ala Gly Arg Val
1               5

<210> SEQ ID NO 57
<211> LENGTH: 8
<212> TYPE: PRT
<213> ORGANISM: Homo sapiens

<400> SEQUENCE: 57

Arg Leu Asp Ala Gly Arg Val Asn
1               5

<210> SEQ ID NO 58
<211> LENGTH: 8
<212> TYPE: PRT
<213> ORGANISM: Homo sapiens

<400> SEQUENCE: 58

Leu Asp Ala Gly Arg Val Asn Thr
1               5

<210> SEQ ID NO 59
<211> LENGTH: 8
<212> TYPE: PRT
<213> ORGANISM: Homo sapiens

<400> SEQUENCE: 59

Asp Ala Gly Arg Val Asn Thr Lys
1               5

<210> SEQ ID NO 60
<211> LENGTH: 8
<212> TYPE: PRT
<213> ORGANISM: Homo sapiens

<400> SEQUENCE: 60

Ala Gly Arg Val Asn Thr Lys Val
1               5

<210> SEQ ID NO 61
<211> LENGTH: 8
<212> TYPE: PRT
<213> ORGANISM: Homo sapiens
```

<400> SEQUENCE: 61

Gly Arg Val Asn Thr Lys Val Arg
1               5

<210> SEQ ID NO 62
<211> LENGTH: 8
<212> TYPE: PRT
<213> ORGANISM: Homo sapiens

<400> SEQUENCE: 62

Arg Val Asn Thr Lys Val Arg Ser
1               5

<210> SEQ ID NO 63
<211> LENGTH: 8
<212> TYPE: PRT
<213> ORGANISM: Homo sapiens

<400> SEQUENCE: 63

Val Asn Thr Lys Val Arg Ser Phe
1               5

<210> SEQ ID NO 64
<211> LENGTH: 8
<212> TYPE: PRT
<213> ORGANISM: Homo sapiens

<400> SEQUENCE: 64

Asn Thr Lys Val Arg Ser Phe Gly
1               5

<210> SEQ ID NO 65
<211> LENGTH: 8
<212> TYPE: PRT
<213> ORGANISM: Homo sapiens

<400> SEQUENCE: 65

Thr Lys Val Arg Ser Phe Gly Pro
1               5

<210> SEQ ID NO 66
<211> LENGTH: 8
<212> TYPE: PRT
<213> ORGANISM: Homo sapiens

<400> SEQUENCE: 66

Lys Val Arg Ser Phe Gly Pro Leu
1               5

<210> SEQ ID NO 67
<211> LENGTH: 8
<212> TYPE: PRT
<213> ORGANISM: Homo sapiens

<400> SEQUENCE: 67

Val Arg Ser Phe Gly Pro Leu Ser
1               5

<210> SEQ ID NO 68
<211> LENGTH: 8
<212> TYPE: PRT
<213> ORGANISM: Homo sapiens

<400> SEQUENCE: 68

```
Arg Ser Phe Gly Pro Leu Ser Lys
1               5
```

<210> SEQ ID NO 69
<211> LENGTH: 8
<212> TYPE: PRT
<213> ORGANISM: Homo sapiens

<400> SEQUENCE: 69

```
Ser Phe Gly Pro Leu Ser Lys Ala
1               5
```

<210> SEQ ID NO 70
<211> LENGTH: 8
<212> TYPE: PRT
<213> ORGANISM: Homo sapiens

<400> SEQUENCE: 70

```
Phe Gly Pro Leu Ser Lys Ala Gly
1               5
```

<210> SEQ ID NO 71
<211> LENGTH: 8
<212> TYPE: PRT
<213> ORGANISM: Homo sapiens

<400> SEQUENCE: 71

```
Gly Pro Leu Ser Lys Ala Gly Phe
1               5
```

<210> SEQ ID NO 72
<211> LENGTH: 8
<212> TYPE: PRT
<213> ORGANISM: Homo sapiens

<400> SEQUENCE: 72

```
Pro Leu Ser Lys Ala Gly Phe Tyr
1               5
```

<210> SEQ ID NO 73
<211> LENGTH: 8
<212> TYPE: PRT
<213> ORGANISM: Homo sapiens

<400> SEQUENCE: 73

```
Leu Ser Lys Ala Gly Phe Tyr Leu
1               5
```

<210> SEQ ID NO 74
<211> LENGTH: 8
<212> TYPE: PRT
<213> ORGANISM: Homo sapiens

<400> SEQUENCE: 74

```
Ser Lys Ala Gly Phe Tyr Leu Ala
1               5
```

<210> SEQ ID NO 75
<211> LENGTH: 8
<212> TYPE: PRT
<213> ORGANISM: Homo sapiens

<400> SEQUENCE: 75

```
Lys Ala Gly Phe Tyr Leu Ala Phe
1               5
```

```
<210> SEQ ID NO 76
<211> LENGTH: 8
<212> TYPE: PRT
<213> ORGANISM: Homo sapiens

<400> SEQUENCE: 76

Ala Gly Phe Tyr Leu Ala Phe Gln
1               5

<210> SEQ ID NO 77
<211> LENGTH: 9
<212> TYPE: PRT
<213> ORGANISM: Homo sapiens

<400> SEQUENCE: 77

Asn Pro Tyr Val Lys Val Asp Thr Ile
1               5

<210> SEQ ID NO 78
<211> LENGTH: 9
<212> TYPE: PRT
<213> ORGANISM: Homo sapiens

<400> SEQUENCE: 78

Pro Tyr Val Lys Val Asp Thr Ile Ala
1               5

<210> SEQ ID NO 79
<211> LENGTH: 9
<212> TYPE: PRT
<213> ORGANISM: Homo sapiens

<400> SEQUENCE: 79

Tyr Val Lys Val Asp Thr Ile Ala Pro
1               5

<210> SEQ ID NO 80
<211> LENGTH: 9
<212> TYPE: PRT
<213> ORGANISM: Homo sapiens

<400> SEQUENCE: 80

Val Lys Val Asp Thr Ile Ala Pro Asp
1               5

<210> SEQ ID NO 81
<211> LENGTH: 9
<212> TYPE: PRT
<213> ORGANISM: Homo sapiens

<400> SEQUENCE: 81

Lys Val Asp Thr Ile Ala Pro Asp Glu
1               5

<210> SEQ ID NO 82
<211> LENGTH: 9
<212> TYPE: PRT
<213> ORGANISM: Homo sapiens

<400> SEQUENCE: 82

Val Asp Thr Ile Ala Pro Asp Glu Ser
1               5

<210> SEQ ID NO 83
<211> LENGTH: 9
```

```
<212> TYPE: PRT
<213> ORGANISM: Homo sapiens

<400> SEQUENCE: 83

Asp Thr Ile Ala Pro Asp Glu Ser Phe
1               5

<210> SEQ ID NO 84
<211> LENGTH: 9
<212> TYPE: PRT
<213> ORGANISM: Homo sapiens

<400> SEQUENCE: 84

Thr Ile Ala Pro Asp Glu Ser Phe Ser
1               5

<210> SEQ ID NO 85
<211> LENGTH: 9
<212> TYPE: PRT
<213> ORGANISM: Homo sapiens

<400> SEQUENCE: 85

Ile Ala Pro Asp Glu Ser Phe Ser Arg
1               5

<210> SEQ ID NO 86
<211> LENGTH: 9
<212> TYPE: PRT
<213> ORGANISM: Homo sapiens

<400> SEQUENCE: 86

Ala Pro Asp Glu Ser Phe Ser Arg Leu
1               5

<210> SEQ ID NO 87
<211> LENGTH: 9
<212> TYPE: PRT
<213> ORGANISM: Homo sapiens

<400> SEQUENCE: 87

Pro Asp Glu Ser Phe Ser Arg Leu Asp
1               5

<210> SEQ ID NO 88
<211> LENGTH: 9
<212> TYPE: PRT
<213> ORGANISM: Homo sapiens

<400> SEQUENCE: 88

Asp Glu Ser Phe Ser Arg Leu Asp Ala
1               5

<210> SEQ ID NO 89
<211> LENGTH: 9
<212> TYPE: PRT
<213> ORGANISM: Homo sapiens

<400> SEQUENCE: 89

Glu Ser Phe Ser Arg Leu Asp Ala Gly
1               5

<210> SEQ ID NO 90
<211> LENGTH: 9
<212> TYPE: PRT
<213> ORGANISM: Homo sapiens
```

```
<400> SEQUENCE: 90

Ser Phe Ser Arg Leu Asp Ala Gly Arg
1               5

<210> SEQ ID NO 91
<211> LENGTH: 9
<212> TYPE: PRT
<213> ORGANISM: Homo sapiens

<400> SEQUENCE: 91

Phe Ser Arg Leu Asp Ala Gly Arg Val
1               5

<210> SEQ ID NO 92
<211> LENGTH: 9
<212> TYPE: PRT
<213> ORGANISM: Homo sapiens

<400> SEQUENCE: 92

Ser Arg Leu Asp Ala Gly Arg Val Asn
1               5

<210> SEQ ID NO 93
<211> LENGTH: 9
<212> TYPE: PRT
<213> ORGANISM: Homo sapiens

<400> SEQUENCE: 93

Arg Leu Asp Ala Gly Arg Val Asn Thr
1               5

<210> SEQ ID NO 94
<211> LENGTH: 9
<212> TYPE: PRT
<213> ORGANISM: Homo sapiens

<400> SEQUENCE: 94

Leu Asp Ala Gly Arg Val Asn Thr Lys
1               5

<210> SEQ ID NO 95
<211> LENGTH: 9
<212> TYPE: PRT
<213> ORGANISM: Homo sapiens

<400> SEQUENCE: 95

Asp Ala Gly Arg Val Asn Thr Lys Val
1               5

<210> SEQ ID NO 96
<211> LENGTH: 9
<212> TYPE: PRT
<213> ORGANISM: Homo sapiens

<400> SEQUENCE: 96

Ala Gly Arg Val Asn Thr Lys Val Arg
1               5

<210> SEQ ID NO 97
<211> LENGTH: 9
<212> TYPE: PRT
<213> ORGANISM: Homo sapiens

<400> SEQUENCE: 97

Gly Arg Val Asn Thr Lys Val Arg Ser
```

```
1               5
```

<210> SEQ ID NO 98
<211> LENGTH: 9
<212> TYPE: PRT
<213> ORGANISM: Homo sapiens

<400> SEQUENCE: 98

```
Arg Val Asn Thr Lys Val Arg Ser Phe
1               5
```

<210> SEQ ID NO 99
<211> LENGTH: 9
<212> TYPE: PRT
<213> ORGANISM: Homo sapiens

<400> SEQUENCE: 99

```
Val Asn Thr Lys Val Arg Ser Phe Gly
1               5
```

<210> SEQ ID NO 100
<211> LENGTH: 9
<212> TYPE: PRT
<213> ORGANISM: Homo sapiens

<400> SEQUENCE: 100

```
Asn Thr Lys Val Arg Ser Phe Gly Pro
1               5
```

<210> SEQ ID NO 101
<211> LENGTH: 9
<212> TYPE: PRT
<213> ORGANISM: Homo sapiens

<400> SEQUENCE: 101

```
Thr Lys Val Arg Ser Phe Gly Pro Leu
1               5
```

<210> SEQ ID NO 102
<211> LENGTH: 9
<212> TYPE: PRT
<213> ORGANISM: Homo sapiens

<400> SEQUENCE: 102

```
Lys Val Arg Ser Phe Gly Pro Leu Ser
1               5
```

<210> SEQ ID NO 103
<211> LENGTH: 9
<212> TYPE: PRT
<213> ORGANISM: Homo sapiens

<400> SEQUENCE: 103

```
Val Arg Ser Phe Gly Pro Leu Ser Lys
1               5
```

<210> SEQ ID NO 104
<211> LENGTH: 9
<212> TYPE: PRT
<213> ORGANISM: Homo sapiens

<400> SEQUENCE: 104

```
Arg Ser Phe Gly Pro Leu Ser Lys Ala
1               5
```

```
<210> SEQ ID NO 105
<211> LENGTH: 9
<212> TYPE: PRT
<213> ORGANISM: Homo sapiens

<400> SEQUENCE: 105

Ser Phe Gly Pro Leu Ser Lys Ala Gly
1               5

<210> SEQ ID NO 106
<211> LENGTH: 9
<212> TYPE: PRT
<213> ORGANISM: Homo sapiens

<400> SEQUENCE: 106

Phe Gly Pro Leu Ser Lys Ala Gly Phe
1               5

<210> SEQ ID NO 107
<211> LENGTH: 9
<212> TYPE: PRT
<213> ORGANISM: Homo sapiens

<400> SEQUENCE: 107

Gly Pro Leu Ser Lys Ala Gly Phe Tyr
1               5

<210> SEQ ID NO 108
<211> LENGTH: 9
<212> TYPE: PRT
<213> ORGANISM: Homo sapiens

<400> SEQUENCE: 108

Pro Leu Ser Lys Ala Gly Phe Tyr Leu
1               5

<210> SEQ ID NO 109
<211> LENGTH: 9
<212> TYPE: PRT
<213> ORGANISM: Homo sapiens

<400> SEQUENCE: 109

Leu Ser Lys Ala Gly Phe Tyr Leu Ala
1               5

<210> SEQ ID NO 110
<211> LENGTH: 9
<212> TYPE: PRT
<213> ORGANISM: Homo sapiens

<400> SEQUENCE: 110

Ser Lys Ala Gly Phe Tyr Leu Ala Phe
1               5

<210> SEQ ID NO 111
<211> LENGTH: 9
<212> TYPE: PRT
<213> ORGANISM: Homo sapiens

<400> SEQUENCE: 111

Lys Ala Gly Phe Tyr Leu Ala Phe Gln
1               5

<210> SEQ ID NO 112
<211> LENGTH: 10
<212> TYPE: PRT
```

<213> ORGANISM: Homo sapiens

<400> SEQUENCE: 112

Asn Pro Tyr Val Lys Val Asp Thr Ile Ala
1               5                   10

<210> SEQ ID NO 113
<211> LENGTH: 10
<212> TYPE: PRT
<213> ORGANISM: Homo sapiens

<400> SEQUENCE: 113

Pro Tyr Val Lys Val Asp Thr Ile Ala Pro
1               5                   10

<210> SEQ ID NO 114
<211> LENGTH: 10
<212> TYPE: PRT
<213> ORGANISM: Homo sapiens

<400> SEQUENCE: 114

Tyr Val Lys Val Asp Thr Ile Ala Pro Asp
1               5                   10

<210> SEQ ID NO 115
<211> LENGTH: 10
<212> TYPE: PRT
<213> ORGANISM: Homo sapiens

<400> SEQUENCE: 115

Val Lys Val Asp Thr Ile Ala Pro Asp Glu
1               5                   10

<210> SEQ ID NO 116
<211> LENGTH: 10
<212> TYPE: PRT
<213> ORGANISM: Homo sapiens

<400> SEQUENCE: 116

Lys Val Asp Thr Ile Ala Pro Asp Glu Ser
1               5                   10

<210> SEQ ID NO 117
<211> LENGTH: 10
<212> TYPE: PRT
<213> ORGANISM: Homo sapiens

<400> SEQUENCE: 117

Val Asp Thr Ile Ala Pro Asp Glu Ser Phe
1               5                   10

<210> SEQ ID NO 118
<211> LENGTH: 10
<212> TYPE: PRT
<213> ORGANISM: Homo sapiens

<400> SEQUENCE: 118

Asp Thr Ile Ala Pro Asp Glu Ser Phe Ser
1               5                   10

<210> SEQ ID NO 119
<211> LENGTH: 10
<212> TYPE: PRT
<213> ORGANISM: Homo sapiens

<400> SEQUENCE: 119

```
Thr Ile Ala Pro Asp Glu Ser Phe Ser Arg
1               5                   10
```

<210> SEQ ID NO 120
<211> LENGTH: 10
<212> TYPE: PRT
<213> ORGANISM: Homo sapiens

<400> SEQUENCE: 120

```
Ile Ala Pro Asp Glu Ser Phe Ser Arg Leu
1               5                   10
```

<210> SEQ ID NO 121
<211> LENGTH: 10
<212> TYPE: PRT
<213> ORGANISM: Homo sapiens

<400> SEQUENCE: 121

```
Ala Pro Asp Glu Ser Phe Ser Arg Leu Asp
1               5                   10
```

<210> SEQ ID NO 122
<211> LENGTH: 10
<212> TYPE: PRT
<213> ORGANISM: Homo sapiens

<400> SEQUENCE: 122

```
Pro Asp Glu Ser Phe Ser Arg Leu Asp Ala
1               5                   10
```

<210> SEQ ID NO 123
<211> LENGTH: 10
<212> TYPE: PRT
<213> ORGANISM: Homo sapiens

<400> SEQUENCE: 123

```
Asp Glu Ser Phe Ser Arg Leu Asp Ala Gly
1               5                   10
```

<210> SEQ ID NO 124
<211> LENGTH: 10
<212> TYPE: PRT
<213> ORGANISM: Homo sapiens

<400> SEQUENCE: 124

```
Glu Ser Phe Ser Arg Leu Asp Ala Gly Arg
1               5                   10
```

<210> SEQ ID NO 125
<211> LENGTH: 10
<212> TYPE: PRT
<213> ORGANISM: Homo sapiens

<400> SEQUENCE: 125

```
Ser Phe Ser Arg Leu Asp Ala Gly Arg Val
1               5                   10
```

<210> SEQ ID NO 126
<211> LENGTH: 10
<212> TYPE: PRT
<213> ORGANISM: Homo sapiens

<400> SEQUENCE: 126

```
Phe Ser Arg Leu Asp Ala Gly Arg Val Asn
1               5                   10
```

<210> SEQ ID NO 127
<211> LENGTH: 10
<212> TYPE: PRT
<213> ORGANISM: Homo sapiens

<400> SEQUENCE: 127

Ser Arg Leu Asp Ala Gly Arg Val Asn Thr
1               5                   10

<210> SEQ ID NO 128
<211> LENGTH: 10
<212> TYPE: PRT
<213> ORGANISM: Homo sapiens

<400> SEQUENCE: 128

Arg Leu Asp Ala Gly Arg Val Asn Thr Lys
1               5                   10

<210> SEQ ID NO 129
<211> LENGTH: 10
<212> TYPE: PRT
<213> ORGANISM: Homo sapiens

<400> SEQUENCE: 129

Leu Asp Ala Gly Arg Val Asn Thr Lys Val
1               5                   10

<210> SEQ ID NO 130
<211> LENGTH: 10
<212> TYPE: PRT
<213> ORGANISM: Homo sapiens

<400> SEQUENCE: 130

Asp Ala Gly Arg Val Asn Thr Lys Val Arg
1               5                   10

<210> SEQ ID NO 131
<211> LENGTH: 10
<212> TYPE: PRT
<213> ORGANISM: Homo sapiens

<400> SEQUENCE: 131

Ala Gly Arg Val Asn Thr Lys Val Arg Ser
1               5                   10

<210> SEQ ID NO 132
<211> LENGTH: 10
<212> TYPE: PRT
<213> ORGANISM: Homo sapiens

<400> SEQUENCE: 132

Gly Arg Val Asn Thr Lys Val Arg Ser Phe
1               5                   10

<210> SEQ ID NO 133
<211> LENGTH: 10
<212> TYPE: PRT
<213> ORGANISM: Homo sapiens

<400> SEQUENCE: 133

Arg Val Asn Thr Lys Val Arg Ser Phe Gly
1               5                   10

<210> SEQ ID NO 134

```
<211> LENGTH: 10
<212> TYPE: PRT
<213> ORGANISM: Homo sapiens

<400> SEQUENCE: 134

Val Asn Thr Lys Val Arg Ser Phe Gly Pro
1               5                   10

<210> SEQ ID NO 135
<211> LENGTH: 10
<212> TYPE: PRT
<213> ORGANISM: Homo sapiens

<400> SEQUENCE: 135

Asn Thr Lys Val Arg Ser Phe Gly Pro Leu
1               5                   10

<210> SEQ ID NO 136
<211> LENGTH: 10
<212> TYPE: PRT
<213> ORGANISM: Homo sapiens

<400> SEQUENCE: 136

Thr Lys Val Arg Ser Phe Gly Pro Leu Ser
1               5                   10

<210> SEQ ID NO 137
<211> LENGTH: 10
<212> TYPE: PRT
<213> ORGANISM: Homo sapiens

<400> SEQUENCE: 137

Lys Val Arg Ser Phe Gly Pro Leu Ser Lys
1               5                   10

<210> SEQ ID NO 138
<211> LENGTH: 10
<212> TYPE: PRT
<213> ORGANISM: Homo sapiens

<400> SEQUENCE: 138

Val Arg Ser Phe Gly Pro Leu Ser Lys Ala
1               5                   10

<210> SEQ ID NO 139
<211> LENGTH: 10
<212> TYPE: PRT
<213> ORGANISM: Homo sapiens

<400> SEQUENCE: 139

Arg Ser Phe Gly Pro Leu Ser Lys Ala Gly
1               5                   10

<210> SEQ ID NO 140
<211> LENGTH: 10
<212> TYPE: PRT
<213> ORGANISM: Homo sapiens

<400> SEQUENCE: 140

Ser Phe Gly Pro Leu Ser Lys Ala Gly Phe
1               5                   10

<210> SEQ ID NO 141
<211> LENGTH: 10
<212> TYPE: PRT
<213> ORGANISM: Homo sapiens
```

<400> SEQUENCE: 141

Phe Gly Pro Leu Ser Lys Ala Gly Phe Tyr
1               5                   10

<210> SEQ ID NO 142
<211> LENGTH: 10
<212> TYPE: PRT
<213> ORGANISM: Homo sapiens

<400> SEQUENCE: 142

Gly Pro Leu Ser Lys Ala Gly Phe Tyr Leu
1               5                   10

<210> SEQ ID NO 143
<211> LENGTH: 10
<212> TYPE: PRT
<213> ORGANISM: Homo sapiens

<400> SEQUENCE: 143

Pro Leu Ser Lys Ala Gly Phe Tyr Leu Ala
1               5                   10

<210> SEQ ID NO 144
<211> LENGTH: 10
<212> TYPE: PRT
<213> ORGANISM: Homo sapiens

<400> SEQUENCE: 144

Leu Ser Lys Ala Gly Phe Tyr Leu Ala Phe
1               5                   10

<210> SEQ ID NO 145
<211> LENGTH: 10
<212> TYPE: PRT
<213> ORGANISM: Homo sapiens

<400> SEQUENCE: 145

Ser Lys Ala Gly Phe Tyr Leu Ala Phe Gln
1               5                   10

<210> SEQ ID NO 146
<211> LENGTH: 8
<212> TYPE: PRT
<213> ORGANISM: Homo sapiens

<400> SEQUENCE: 146

Asn Ala Val Glu Val Ser Val Pro
1               5

<210> SEQ ID NO 147
<211> LENGTH: 8
<212> TYPE: PRT
<213> ORGANISM: Homo sapiens

<400> SEQUENCE: 147

Ala Val Glu Val Ser Val Pro Leu
1               5

<210> SEQ ID NO 148
<211> LENGTH: 8
<212> TYPE: PRT
<213> ORGANISM: Homo sapiens

<400> SEQUENCE: 148

```
Val Glu Val Ser Val Pro Leu Lys
1               5

<210> SEQ ID NO 149
<211> LENGTH: 8
<212> TYPE: PRT
<213> ORGANISM: Homo sapiens

<400> SEQUENCE: 149

Glu Val Ser Val Pro Leu Lys Leu
1               5

<210> SEQ ID NO 150
<211> LENGTH: 8
<212> TYPE: PRT
<213> ORGANISM: Homo sapiens

<400> SEQUENCE: 150

Val Ser Val Pro Leu Lys Leu Tyr
1               5

<210> SEQ ID NO 151
<211> LENGTH: 8
<212> TYPE: PRT
<213> ORGANISM: Homo sapiens

<400> SEQUENCE: 151

Ser Val Pro Leu Lys Leu Tyr Cys
1               5

<210> SEQ ID NO 152
<211> LENGTH: 9
<212> TYPE: PRT
<213> ORGANISM: Homo sapiens

<400> SEQUENCE: 152

Asn Ala Val Glu Val Ser Val Pro Leu
1               5

<210> SEQ ID NO 153
<211> LENGTH: 9
<212> TYPE: PRT
<213> ORGANISM: Homo sapiens

<400> SEQUENCE: 153

Ala Val Glu Val Ser Val Pro Leu Lys
1               5

<210> SEQ ID NO 154
<211> LENGTH: 9
<212> TYPE: PRT
<213> ORGANISM: Homo sapiens

<400> SEQUENCE: 154

Val Glu Val Ser Val Pro Leu Lys Leu
1               5

<210> SEQ ID NO 155
<211> LENGTH: 9
<212> TYPE: PRT
<213> ORGANISM: Homo sapiens

<400> SEQUENCE: 155

Glu Val Ser Val Pro Leu Lys Leu Tyr
1               5
```

```
<210> SEQ ID NO 156
<211> LENGTH: 9
<212> TYPE: PRT
<213> ORGANISM: Homo sapiens

<400> SEQUENCE: 156

Val Ser Val Pro Leu Lys Leu Tyr Cys
1               5

<210> SEQ ID NO 157
<211> LENGTH: 10
<212> TYPE: PRT
<213> ORGANISM: Homo sapiens

<400> SEQUENCE: 157

Asn Ala Val Glu Val Ser Val Pro Leu Lys
1               5                   10

<210> SEQ ID NO 158
<211> LENGTH: 10
<212> TYPE: PRT
<213> ORGANISM: Homo sapiens

<400> SEQUENCE: 158

Ala Val Glu Val Ser Val Pro Leu Lys Leu
1               5                   10

<210> SEQ ID NO 159
<211> LENGTH: 10
<212> TYPE: PRT
<213> ORGANISM: Homo sapiens

<400> SEQUENCE: 159

Val Glu Val Ser Val Pro Leu Lys Leu Tyr
1               5                   10

<210> SEQ ID NO 160
<211> LENGTH: 10
<212> TYPE: PRT
<213> ORGANISM: Homo sapiens

<400> SEQUENCE: 160

Glu Val Ser Val Pro Leu Lys Leu Tyr Cys
1               5                   10

<210> SEQ ID NO 161
<211> LENGTH: 8
<212> TYPE: PRT
<213> ORGANISM: Homo sapiens

<400> SEQUENCE: 161

Gly His Glu Pro Ala Ala Lys Glu
1               5

<210> SEQ ID NO 162
<211> LENGTH: 8
<212> TYPE: PRT
<213> ORGANISM: Homo sapiens

<400> SEQUENCE: 162

His Glu Pro Ala Ala Lys Glu Ser
1               5

<210> SEQ ID NO 163
<211> LENGTH: 8
```

```
<212> TYPE: PRT
<213> ORGANISM: Homo sapiens

<400> SEQUENCE: 163

Glu Pro Ala Ala Lys Glu Ser Gln
1               5

<210> SEQ ID NO 164
<211> LENGTH: 8
<212> TYPE: PRT
<213> ORGANISM: Homo sapiens

<400> SEQUENCE: 164

Pro Ala Ala Lys Glu Ser Gln Cys
1               5

<210> SEQ ID NO 165
<211> LENGTH: 8
<212> TYPE: PRT
<213> ORGANISM: Homo sapiens

<400> SEQUENCE: 165

Ala Ala Lys Glu Ser Gln Cys Arg
1               5

<210> SEQ ID NO 166
<211> LENGTH: 8
<212> TYPE: PRT
<213> ORGANISM: Homo sapiens

<400> SEQUENCE: 166

Ala Lys Glu Ser Gln Cys Arg Pro
1               5

<210> SEQ ID NO 167
<211> LENGTH: 8
<212> TYPE: PRT
<213> ORGANISM: Homo sapiens

<400> SEQUENCE: 167

Lys Glu Ser Gln Cys Arg Pro Cys
1               5

<210> SEQ ID NO 168
<211> LENGTH: 8
<212> TYPE: PRT
<213> ORGANISM: Homo sapiens

<400> SEQUENCE: 168

Glu Ser Gln Cys Arg Pro Cys Pro
1               5

<210> SEQ ID NO 169
<211> LENGTH: 8
<212> TYPE: PRT
<213> ORGANISM: Homo sapiens

<400> SEQUENCE: 169

Ser Gln Cys Arg Pro Cys Pro Pro
1               5

<210> SEQ ID NO 170
<211> LENGTH: 8
<212> TYPE: PRT
<213> ORGANISM: Homo sapiens
```

-continued

```
<400> SEQUENCE: 170

Gln Cys Arg Pro Cys Pro Pro Gly
1               5

<210> SEQ ID NO 171
<211> LENGTH: 8
<212> TYPE: PRT
<213> ORGANISM: Homo sapiens

<400> SEQUENCE: 171

Cys Arg Pro Cys Pro Pro Gly Ser
1               5

<210> SEQ ID NO 172
<211> LENGTH: 8
<212> TYPE: PRT
<213> ORGANISM: Homo sapiens

<400> SEQUENCE: 172

Arg Pro Cys Pro Pro Gly Ser Tyr
1               5

<210> SEQ ID NO 173
<211> LENGTH: 8
<212> TYPE: PRT
<213> ORGANISM: Homo sapiens

<400> SEQUENCE: 173

Pro Cys Pro Pro Gly Ser Tyr Lys
1               5

<210> SEQ ID NO 174
<211> LENGTH: 8
<212> TYPE: PRT
<213> ORGANISM: Homo sapiens

<400> SEQUENCE: 174

Cys Pro Pro Gly Ser Tyr Lys Ala
1               5

<210> SEQ ID NO 175
<211> LENGTH: 8
<212> TYPE: PRT
<213> ORGANISM: Homo sapiens

<400> SEQUENCE: 175

Pro Pro Gly Ser Tyr Lys Ala Lys
1               5

<210> SEQ ID NO 176
<211> LENGTH: 8
<212> TYPE: PRT
<213> ORGANISM: Homo sapiens

<400> SEQUENCE: 176

Pro Gly Ser Tyr Lys Ala Lys Gln
1               5

<210> SEQ ID NO 177
<211> LENGTH: 8
<212> TYPE: PRT
<213> ORGANISM: Homo sapiens

<400> SEQUENCE: 177

Gly Ser Tyr Lys Ala Lys Gln Gly
```

```
1               5

<210> SEQ ID NO 178
<211> LENGTH: 8
<212> TYPE: PRT
<213> ORGANISM: Homo sapiens

<400> SEQUENCE: 178

Ser Tyr Lys Ala Lys Gln Gly Glu
1               5

<210> SEQ ID NO 179
<211> LENGTH: 9
<212> TYPE: PRT
<213> ORGANISM: Homo sapiens

<400> SEQUENCE: 179

Gly His Glu Pro Ala Ala Lys Glu Ser
1               5

<210> SEQ ID NO 180
<211> LENGTH: 9
<212> TYPE: PRT
<213> ORGANISM: Homo sapiens

<400> SEQUENCE: 180

His Glu Pro Ala Ala Lys Glu Ser Gln
1               5

<210> SEQ ID NO 181
<211> LENGTH: 9
<212> TYPE: PRT
<213> ORGANISM: Homo sapiens

<400> SEQUENCE: 181

Glu Pro Ala Ala Lys Glu Ser Gln Cys
1               5

<210> SEQ ID NO 182
<211> LENGTH: 9
<212> TYPE: PRT
<213> ORGANISM: Homo sapiens

<400> SEQUENCE: 182

Pro Ala Ala Lys Glu Ser Gln Cys Arg
1               5

<210> SEQ ID NO 183
<211> LENGTH: 9
<212> TYPE: PRT
<213> ORGANISM: Homo sapiens

<400> SEQUENCE: 183

Ala Ala Lys Glu Ser Gln Cys Arg Pro
1               5

<210> SEQ ID NO 184
<211> LENGTH: 9
<212> TYPE: PRT
<213> ORGANISM: Homo sapiens

<400> SEQUENCE: 184

Ala Lys Glu Ser Gln Cys Arg Pro Cys
1               5
```

```
<210> SEQ ID NO 185
<211> LENGTH: 9
<212> TYPE: PRT
<213> ORGANISM: Homo sapiens

<400> SEQUENCE: 185

Lys Glu Ser Gln Cys Arg Pro Cys Pro
1               5

<210> SEQ ID NO 186
<211> LENGTH: 9
<212> TYPE: PRT
<213> ORGANISM: Homo sapiens

<400> SEQUENCE: 186

Glu Ser Gln Cys Arg Pro Cys Pro Pro
1               5

<210> SEQ ID NO 187
<211> LENGTH: 9
<212> TYPE: PRT
<213> ORGANISM: Homo sapiens

<400> SEQUENCE: 187

Ser Gln Cys Arg Pro Cys Pro Pro Gly
1               5

<210> SEQ ID NO 188
<211> LENGTH: 9
<212> TYPE: PRT
<213> ORGANISM: Homo sapiens

<400> SEQUENCE: 188

Gln Cys Arg Pro Cys Pro Pro Gly Ser
1               5

<210> SEQ ID NO 189
<211> LENGTH: 9
<212> TYPE: PRT
<213> ORGANISM: Homo sapiens

<400> SEQUENCE: 189

Cys Arg Pro Cys Pro Pro Gly Ser Tyr
1               5

<210> SEQ ID NO 190
<211> LENGTH: 9
<212> TYPE: PRT
<213> ORGANISM: Homo sapiens

<400> SEQUENCE: 190

Arg Pro Cys Pro Pro Gly Ser Tyr Lys
1               5

<210> SEQ ID NO 191
<211> LENGTH: 9
<212> TYPE: PRT
<213> ORGANISM: Homo sapiens

<400> SEQUENCE: 191

Pro Cys Pro Pro Gly Ser Tyr Lys Ala
1               5

<210> SEQ ID NO 192
<211> LENGTH: 9
<212> TYPE: PRT
```

<213> ORGANISM: Homo sapiens

<400> SEQUENCE: 192

Cys Pro Pro Gly Ser Tyr Lys Ala Lys
1               5

<210> SEQ ID NO 193
<211> LENGTH: 9
<212> TYPE: PRT
<213> ORGANISM: Homo sapiens

<400> SEQUENCE: 193

Pro Pro Gly Ser Tyr Lys Ala Lys Gln
1               5

<210> SEQ ID NO 194
<211> LENGTH: 9
<212> TYPE: PRT
<213> ORGANISM: Homo sapiens

<400> SEQUENCE: 194

Pro Gly Ser Tyr Lys Ala Lys Gln Gly
1               5

<210> SEQ ID NO 195
<211> LENGTH: 9
<212> TYPE: PRT
<213> ORGANISM: Homo sapiens

<400> SEQUENCE: 195

Gly Ser Tyr Lys Ala Lys Gln Gly Glu
1               5

<210> SEQ ID NO 196
<211> LENGTH: 10
<212> TYPE: PRT
<213> ORGANISM: Homo sapiens

<400> SEQUENCE: 196

Gly His Glu Pro Ala Ala Lys Glu Ser Gln
1               5                   10

<210> SEQ ID NO 197
<211> LENGTH: 10
<212> TYPE: PRT
<213> ORGANISM: Homo sapiens

<400> SEQUENCE: 197

His Glu Pro Ala Ala Lys Glu Ser Gln Cys
1               5                   10

<210> SEQ ID NO 198
<211> LENGTH: 10
<212> TYPE: PRT
<213> ORGANISM: Homo sapiens

<400> SEQUENCE: 198

Glu Pro Ala Ala Lys Glu Ser Gln Cys Arg
1               5                   10

<210> SEQ ID NO 199
<211> LENGTH: 10
<212> TYPE: PRT
<213> ORGANISM: Homo sapiens

<400> SEQUENCE: 199

```
Pro Ala Ala Lys Glu Ser Gln Cys Arg Pro
1               5                   10
```

<210> SEQ ID NO 200
<211> LENGTH: 10
<212> TYPE: PRT
<213> ORGANISM: Homo sapiens

<400> SEQUENCE: 200

```
Ala Ala Lys Glu Ser Gln Cys Arg Pro Cys
1               5                   10
```

<210> SEQ ID NO 201
<211> LENGTH: 10
<212> TYPE: PRT
<213> ORGANISM: Homo sapiens

<400> SEQUENCE: 201

```
Ala Lys Glu Ser Gln Cys Arg Pro Cys Pro
1               5                   10
```

<210> SEQ ID NO 202
<211> LENGTH: 10
<212> TYPE: PRT
<213> ORGANISM: Homo sapiens

<400> SEQUENCE: 202

```
Lys Glu Ser Gln Cys Arg Pro Cys Pro Pro
1               5                   10
```

<210> SEQ ID NO 203
<211> LENGTH: 10
<212> TYPE: PRT
<213> ORGANISM: Homo sapiens

<400> SEQUENCE: 203

```
Glu Ser Gln Cys Arg Pro Cys Pro Pro Gly
1               5                   10
```

<210> SEQ ID NO 204
<211> LENGTH: 10
<212> TYPE: PRT
<213> ORGANISM: Homo sapiens

<400> SEQUENCE: 204

```
Ser Gln Cys Arg Pro Cys Pro Pro Gly Ser
1               5                   10
```

<210> SEQ ID NO 205
<211> LENGTH: 10
<212> TYPE: PRT
<213> ORGANISM: Homo sapiens

<400> SEQUENCE: 205

```
Gln Cys Arg Pro Cys Pro Pro Gly Ser Tyr
1               5                   10
```

<210> SEQ ID NO 206
<211> LENGTH: 10
<212> TYPE: PRT
<213> ORGANISM: Homo sapiens

<400> SEQUENCE: 206

```
Cys Arg Pro Cys Pro Pro Gly Ser Tyr Lys
1               5                   10
```

<210> SEQ ID NO 207
<211> LENGTH: 10
<212> TYPE: PRT
<213> ORGANISM: Homo sapiens

<400> SEQUENCE: 207

Arg Pro Cys Pro Pro Gly Ser Tyr Lys Ala
1               5                   10

<210> SEQ ID NO 208
<211> LENGTH: 10
<212> TYPE: PRT
<213> ORGANISM: Homo sapiens

<400> SEQUENCE: 208

Pro Cys Pro Pro Gly Ser Tyr Lys Ala Lys
1               5                   10

<210> SEQ ID NO 209
<211> LENGTH: 10
<212> TYPE: PRT
<213> ORGANISM: Homo sapiens

<400> SEQUENCE: 209

Cys Pro Pro Gly Ser Tyr Lys Ala Lys Gln
1               5                   10

<210> SEQ ID NO 210
<211> LENGTH: 10
<212> TYPE: PRT
<213> ORGANISM: Homo sapiens

<400> SEQUENCE: 210

Pro Pro Gly Ser Tyr Lys Ala Lys Gln Gly
1               5                   10

<210> SEQ ID NO 211
<211> LENGTH: 10
<212> TYPE: PRT
<213> ORGANISM: Homo sapiens

<400> SEQUENCE: 211

Pro Gly Ser Tyr Lys Ala Lys Gln Gly Glu
1               5                   10

<210> SEQ ID NO 212
<211> LENGTH: 8
<212> TYPE: PRT
<213> ORGANISM: Homo sapiens

<400> SEQUENCE: 212

Pro Ala Ala Ser Ile Cys Thr Cys
1               5

<210> SEQ ID NO 213
<211> LENGTH: 8
<212> TYPE: PRT
<213> ORGANISM: Homo sapiens

<400> SEQUENCE: 213

Ala Ala Ser Ile Cys Thr Cys His
1               5

<210> SEQ ID NO 214

```
<211> LENGTH: 8
<212> TYPE: PRT
<213> ORGANISM: Homo sapiens

<400> SEQUENCE: 214

Ala Ser Ile Cys Thr Cys His Asn
1               5

<210> SEQ ID NO 215
<211> LENGTH: 8
<212> TYPE: PRT
<213> ORGANISM: Homo sapiens

<400> SEQUENCE: 215

Ser Ile Cys Thr Cys His Asn Asn
1               5

<210> SEQ ID NO 216
<211> LENGTH: 8
<212> TYPE: PRT
<213> ORGANISM: Homo sapiens

<400> SEQUENCE: 216

Ile Cys Thr Cys His Asn Asn Phe
1               5

<210> SEQ ID NO 217
<211> LENGTH: 8
<212> TYPE: PRT
<213> ORGANISM: Homo sapiens

<400> SEQUENCE: 217

Cys Thr Cys His Asn Asn Phe Tyr
1               5

<210> SEQ ID NO 218
<211> LENGTH: 8
<212> TYPE: PRT
<213> ORGANISM: Homo sapiens

<400> SEQUENCE: 218

Thr Cys His Asn Asn Phe Tyr Arg
1               5

<210> SEQ ID NO 219
<211> LENGTH: 8
<212> TYPE: PRT
<213> ORGANISM: Homo sapiens

<400> SEQUENCE: 219

Cys His Asn Asn Phe Tyr Arg Ala
1               5

<210> SEQ ID NO 220
<211> LENGTH: 8
<212> TYPE: PRT
<213> ORGANISM: Homo sapiens

<400> SEQUENCE: 220

His Asn Asn Phe Tyr Arg Ala Asp
1               5

<210> SEQ ID NO 221
<211> LENGTH: 8
<212> TYPE: PRT
<213> ORGANISM: Homo sapiens
```

<400> SEQUENCE: 221

Asn Asn Phe Tyr Arg Ala Asp Ser
1               5

<210> SEQ ID NO 222
<211> LENGTH: 8
<212> TYPE: PRT
<213> ORGANISM: Homo sapiens

<400> SEQUENCE: 222

Asn Phe Tyr Arg Ala Asp Ser Asp
1               5

<210> SEQ ID NO 223
<211> LENGTH: 8
<212> TYPE: PRT
<213> ORGANISM: Homo sapiens

<400> SEQUENCE: 223

Phe Tyr Arg Ala Asp Ser Asp Ser
1               5

<210> SEQ ID NO 224
<211> LENGTH: 8
<212> TYPE: PRT
<213> ORGANISM: Homo sapiens

<400> SEQUENCE: 224

Tyr Arg Ala Asp Ser Asp Ser Ala
1               5

<210> SEQ ID NO 225
<211> LENGTH: 8
<212> TYPE: PRT
<213> ORGANISM: Homo sapiens

<400> SEQUENCE: 225

Arg Ala Asp Ser Asp Ser Ala Asp
1               5

<210> SEQ ID NO 226
<211> LENGTH: 8
<212> TYPE: PRT
<213> ORGANISM: Homo sapiens

<400> SEQUENCE: 226

Ala Asp Ser Asp Ser Ala Asp Ser
1               5

<210> SEQ ID NO 227
<211> LENGTH: 8
<212> TYPE: PRT
<213> ORGANISM: Homo sapiens

<400> SEQUENCE: 227

Asp Ser Asp Ser Ala Asp Ser Ala
1               5

<210> SEQ ID NO 228
<211> LENGTH: 8
<212> TYPE: PRT
<213> ORGANISM: Homo sapiens

<400> SEQUENCE: 228

```
Ser Asp Ser Ala Asp Ser Ala Cys
1               5
```

<210> SEQ ID NO 229
<211> LENGTH: 9
<212> TYPE: PRT
<213> ORGANISM: Homo sapiens

<400> SEQUENCE: 229

```
Pro Ala Ala Ser Ile Cys Thr Cys His
1               5
```

<210> SEQ ID NO 230
<211> LENGTH: 9
<212> TYPE: PRT
<213> ORGANISM: Homo sapiens

<400> SEQUENCE: 230

```
Ala Ala Ser Ile Cys Thr Cys His Asn
1               5
```

<210> SEQ ID NO 231
<211> LENGTH: 9
<212> TYPE: PRT
<213> ORGANISM: Homo sapiens

<400> SEQUENCE: 231

```
Ala Ser Ile Cys Thr Cys His Asn Asn
1               5
```

<210> SEQ ID NO 232
<211> LENGTH: 9
<212> TYPE: PRT
<213> ORGANISM: Homo sapiens

<400> SEQUENCE: 232

```
Ser Ile Cys Thr Cys His Asn Asn Phe
1               5
```

<210> SEQ ID NO 233
<211> LENGTH: 9
<212> TYPE: PRT
<213> ORGANISM: Homo sapiens

<400> SEQUENCE: 233

```
Ile Cys Thr Cys His Asn Asn Phe Tyr
1               5
```

<210> SEQ ID NO 234
<211> LENGTH: 9
<212> TYPE: PRT
<213> ORGANISM: Homo sapiens

<400> SEQUENCE: 234

```
Cys Thr Cys His Asn Asn Phe Tyr Arg
1               5
```

<210> SEQ ID NO 235
<211> LENGTH: 9
<212> TYPE: PRT
<213> ORGANISM: Homo sapiens

<400> SEQUENCE: 235

```
Thr Cys His Asn Asn Phe Tyr Arg Ala
1               5
```

```
<210> SEQ ID NO 236
<211> LENGTH: 9
<212> TYPE: PRT
<213> ORGANISM: Homo sapiens

<400> SEQUENCE: 236

Cys His Asn Asn Phe Tyr Arg Ala Asp
1               5

<210> SEQ ID NO 237
<211> LENGTH: 9
<212> TYPE: PRT
<213> ORGANISM: Homo sapiens

<400> SEQUENCE: 237

His Asn Asn Phe Tyr Arg Ala Asp Ser
1               5

<210> SEQ ID NO 238
<211> LENGTH: 9
<212> TYPE: PRT
<213> ORGANISM: Homo sapiens

<400> SEQUENCE: 238

Asn Asn Phe Tyr Arg Ala Asp Ser Asp
1               5

<210> SEQ ID NO 239
<211> LENGTH: 9
<212> TYPE: PRT
<213> ORGANISM: Homo sapiens

<400> SEQUENCE: 239

Asn Phe Tyr Arg Ala Asp Ser Asp Ser
1               5

<210> SEQ ID NO 240
<211> LENGTH: 9
<212> TYPE: PRT
<213> ORGANISM: Homo sapiens

<400> SEQUENCE: 240

Phe Tyr Arg Ala Asp Ser Asp Ser Ala
1               5

<210> SEQ ID NO 241
<211> LENGTH: 9
<212> TYPE: PRT
<213> ORGANISM: Homo sapiens

<400> SEQUENCE: 241

Tyr Arg Ala Asp Ser Asp Ser Ala Asp
1               5

<210> SEQ ID NO 242
<211> LENGTH: 9
<212> TYPE: PRT
<213> ORGANISM: Homo sapiens

<400> SEQUENCE: 242

Arg Ala Asp Ser Asp Ser Ala Asp Ser
1               5

<210> SEQ ID NO 243
<211> LENGTH: 9
```

```
<212> TYPE: PRT
<213> ORGANISM: Homo sapiens

<400> SEQUENCE: 243

Ala Asp Ser Asp Ser Ala Asp Ser Ala
1               5

<210> SEQ ID NO 244
<211> LENGTH: 9
<212> TYPE: PRT
<213> ORGANISM: Homo sapiens

<400> SEQUENCE: 244

Asp Ser Asp Ser Ala Asp Ser Ala Cys
1               5

<210> SEQ ID NO 245
<211> LENGTH: 10
<212> TYPE: PRT
<213> ORGANISM: Homo sapiens

<400> SEQUENCE: 245

Pro Ala Ala Ser Ile Cys Thr Cys His Asn
1               5                   10

<210> SEQ ID NO 246
<211> LENGTH: 10
<212> TYPE: PRT
<213> ORGANISM: Homo sapiens

<400> SEQUENCE: 246

Ala Ala Ser Ile Cys Thr Cys His Asn Asn
1               5                   10

<210> SEQ ID NO 247
<211> LENGTH: 10
<212> TYPE: PRT
<213> ORGANISM: Homo sapiens

<400> SEQUENCE: 247

Ala Ser Ile Cys Thr Cys His Asn Asn Phe
1               5                   10

<210> SEQ ID NO 248
<211> LENGTH: 10
<212> TYPE: PRT
<213> ORGANISM: Homo sapiens

<400> SEQUENCE: 248

Ser Ile Cys Thr Cys His Asn Asn Phe Tyr
1               5                   10

<210> SEQ ID NO 249
<211> LENGTH: 10
<212> TYPE: PRT
<213> ORGANISM: Homo sapiens

<400> SEQUENCE: 249

Ile Cys Thr Cys His Asn Asn Phe Tyr Arg
1               5                   10

<210> SEQ ID NO 250
<211> LENGTH: 10
<212> TYPE: PRT
<213> ORGANISM: Homo sapiens
```

```
<400> SEQUENCE: 250

Cys Thr Cys His Asn Asn Phe Tyr Arg Ala
1               5                   10

<210> SEQ ID NO 251
<211> LENGTH: 10
<212> TYPE: PRT
<213> ORGANISM: Homo sapiens

<400> SEQUENCE: 251

Thr Cys His Asn Asn Phe Tyr Arg Ala Asp
1               5                   10

<210> SEQ ID NO 252
<211> LENGTH: 10
<212> TYPE: PRT
<213> ORGANISM: Homo sapiens

<400> SEQUENCE: 252

Cys His Asn Asn Phe Tyr Arg Ala Asp Ser
1               5                   10

<210> SEQ ID NO 253
<211> LENGTH: 10
<212> TYPE: PRT
<213> ORGANISM: Homo sapiens

<400> SEQUENCE: 253

His Asn Asn Phe Tyr Arg Ala Asp Ser Asp
1               5                   10

<210> SEQ ID NO 254
<211> LENGTH: 10
<212> TYPE: PRT
<213> ORGANISM: Homo sapiens

<400> SEQUENCE: 254

Asn Asn Phe Tyr Arg Ala Asp Ser Asp Ser
1               5                   10

<210> SEQ ID NO 255
<211> LENGTH: 10
<212> TYPE: PRT
<213> ORGANISM: Homo sapiens

<400> SEQUENCE: 255

Asn Phe Tyr Arg Ala Asp Ser Asp Ser Ala
1               5                   10

<210> SEQ ID NO 256
<211> LENGTH: 10
<212> TYPE: PRT
<213> ORGANISM: Homo sapiens

<400> SEQUENCE: 256

Phe Tyr Arg Ala Asp Ser Asp Ser Ala Asp
1               5                   10

<210> SEQ ID NO 257
<211> LENGTH: 10
<212> TYPE: PRT
<213> ORGANISM: Homo sapiens

<400> SEQUENCE: 257

Tyr Arg Ala Asp Ser Asp Ser Ala Asp Ser
```

```
1               5                   10
```

<210> SEQ ID NO 258
<211> LENGTH: 10
<212> TYPE: PRT
<213> ORGANISM: Homo sapiens

<400> SEQUENCE: 258

```
Arg Ala Asp Ser Asp Ser Ala Asp Ser Ala
1               5                   10
```

<210> SEQ ID NO 259
<211> LENGTH: 10
<212> TYPE: PRT
<213> ORGANISM: Homo sapiens

<400> SEQUENCE: 259

```
Ala Asp Ser Asp Ser Ala Asp Ser Ala Cys
1               5                   10
```

<210> SEQ ID NO 260
<211> LENGTH: 8
<212> TYPE: PRT
<213> ORGANISM: Homo sapiens

<400> SEQUENCE: 260

```
Pro Arg Asp Leu Gly Gly Arg Asp
1               5
```

<210> SEQ ID NO 261
<211> LENGTH: 8
<212> TYPE: PRT
<213> ORGANISM: Homo sapiens

<400> SEQUENCE: 261

```
Arg Asp Leu Gly Gly Arg Asp Asp
1               5
```

<210> SEQ ID NO 262
<211> LENGTH: 8
<212> TYPE: PRT
<213> ORGANISM: Homo sapiens

<400> SEQUENCE: 262

```
Asp Leu Gly Gly Arg Asp Asp Leu
1               5
```

<210> SEQ ID NO 263
<211> LENGTH: 8
<212> TYPE: PRT
<213> ORGANISM: Homo sapiens

<400> SEQUENCE: 263

```
Leu Gly Gly Arg Asp Asp Leu Leu
1               5
```

<210> SEQ ID NO 264
<211> LENGTH: 8
<212> TYPE: PRT
<213> ORGANISM: Homo sapiens

<400> SEQUENCE: 264

```
Gly Gly Arg Asp Asp Leu Leu Tyr
1               5
```

```
<210> SEQ ID NO 265
<211> LENGTH: 8
<212> TYPE: PRT
<213> ORGANISM: Homo sapiens

<400> SEQUENCE: 265

Gly Arg Asp Asp Leu Leu Tyr Asn
1               5

<210> SEQ ID NO 266
<211> LENGTH: 8
<212> TYPE: PRT
<213> ORGANISM: Homo sapiens

<400> SEQUENCE: 266

Arg Asp Asp Leu Leu Tyr Asn Val
1               5

<210> SEQ ID NO 267
<211> LENGTH: 8
<212> TYPE: PRT
<213> ORGANISM: Homo sapiens

<400> SEQUENCE: 267

Asp Asp Leu Leu Tyr Asn Val Ile
1               5

<210> SEQ ID NO 268
<211> LENGTH: 8
<212> TYPE: PRT
<213> ORGANISM: Homo sapiens

<400> SEQUENCE: 268

Asp Leu Leu Tyr Asn Val Ile Cys
1               5

<210> SEQ ID NO 269
<211> LENGTH: 8
<212> TYPE: PRT
<213> ORGANISM: Homo sapiens

<400> SEQUENCE: 269

Leu Leu Tyr Asn Val Ile Cys Lys
1               5

<210> SEQ ID NO 270
<211> LENGTH: 8
<212> TYPE: PRT
<213> ORGANISM: Homo sapiens

<400> SEQUENCE: 270

Leu Tyr Asn Val Ile Cys Lys Lys
1               5

<210> SEQ ID NO 271
<211> LENGTH: 8
<212> TYPE: PRT
<213> ORGANISM: Homo sapiens

<400> SEQUENCE: 271

Tyr Asn Val Ile Cys Lys Lys Cys
1               5

<210> SEQ ID NO 272
<211> LENGTH: 8
<212> TYPE: PRT
```

<213> ORGANISM: Homo sapiens

<400> SEQUENCE: 272

Asn Val Ile Cys Lys Lys Cys His
1               5

<210> SEQ ID NO 273
<211> LENGTH: 8
<212> TYPE: PRT
<213> ORGANISM: Homo sapiens

<400> SEQUENCE: 273

Val Ile Cys Lys Lys Cys His Gly
1               5

<210> SEQ ID NO 274
<211> LENGTH: 8
<212> TYPE: PRT
<213> ORGANISM: Homo sapiens

<400> SEQUENCE: 274

Ile Cys Lys Lys Cys His Gly Ala
1               5

<210> SEQ ID NO 275
<211> LENGTH: 9
<212> TYPE: PRT
<213> ORGANISM: Homo sapiens

<400> SEQUENCE: 275

Pro Arg Asp Leu Gly Gly Arg Asp Asp
1               5

<210> SEQ ID NO 276
<211> LENGTH: 9
<212> TYPE: PRT
<213> ORGANISM: Homo sapiens

<400> SEQUENCE: 276

Arg Asp Leu Gly Gly Arg Asp Asp Leu
1               5

<210> SEQ ID NO 277
<211> LENGTH: 9
<212> TYPE: PRT
<213> ORGANISM: Homo sapiens

<400> SEQUENCE: 277

Asp Leu Gly Gly Arg Asp Asp Leu Leu
1               5

<210> SEQ ID NO 278
<211> LENGTH: 9
<212> TYPE: PRT
<213> ORGANISM: Homo sapiens

<400> SEQUENCE: 278

Leu Gly Gly Arg Asp Asp Leu Leu Tyr
1               5

<210> SEQ ID NO 279
<211> LENGTH: 9
<212> TYPE: PRT
<213> ORGANISM: Homo sapiens

<400> SEQUENCE: 279

Gly Gly Arg Asp Asp Leu Leu Tyr Asn
1               5

<210> SEQ ID NO 280
<211> LENGTH: 9
<212> TYPE: PRT
<213> ORGANISM: Homo sapiens

<400> SEQUENCE: 280

Gly Arg Asp Asp Leu Leu Tyr Asn Val
1               5

<210> SEQ ID NO 281
<211> LENGTH: 9
<212> TYPE: PRT
<213> ORGANISM: Homo sapiens

<400> SEQUENCE: 281

Arg Asp Asp Leu Leu Tyr Asn Val Ile
1               5

<210> SEQ ID NO 282
<211> LENGTH: 9
<212> TYPE: PRT
<213> ORGANISM: Homo sapiens

<400> SEQUENCE: 282

Asp Asp Leu Leu Tyr Asn Val Ile Cys
1               5

<210> SEQ ID NO 283
<211> LENGTH: 9
<212> TYPE: PRT
<213> ORGANISM: Homo sapiens

<400> SEQUENCE: 283

Asp Leu Leu Tyr Asn Val Ile Cys Lys
1               5

<210> SEQ ID NO 284
<211> LENGTH: 9
<212> TYPE: PRT
<213> ORGANISM: Homo sapiens

<400> SEQUENCE: 284

Leu Leu Tyr Asn Val Ile Cys Lys Lys
1               5

<210> SEQ ID NO 285
<211> LENGTH: 9
<212> TYPE: PRT
<213> ORGANISM: Homo sapiens

<400> SEQUENCE: 285

Leu Tyr Asn Val Ile Cys Lys Lys Cys
1               5

<210> SEQ ID NO 286
<211> LENGTH: 9
<212> TYPE: PRT
<213> ORGANISM: Homo sapiens

<400> SEQUENCE: 286

Tyr Asn Val Ile Cys Lys Lys Cys His
1               5

```
<210> SEQ ID NO 287
<211> LENGTH: 9
<212> TYPE: PRT
<213> ORGANISM: Homo sapiens

<400> SEQUENCE: 287

Asn Val Ile Cys Lys Lys Cys His Gly
1               5

<210> SEQ ID NO 288
<211> LENGTH: 9
<212> TYPE: PRT
<213> ORGANISM: Homo sapiens

<400> SEQUENCE: 288

Val Ile Cys Lys Lys Cys His Gly Ala
1               5

<210> SEQ ID NO 289
<211> LENGTH: 10
<212> TYPE: PRT
<213> ORGANISM: Homo sapiens

<400> SEQUENCE: 289

Pro Arg Asp Leu Gly Gly Arg Asp Asp Leu
1               5                   10

<210> SEQ ID NO 290
<211> LENGTH: 10
<212> TYPE: PRT
<213> ORGANISM: Homo sapiens

<400> SEQUENCE: 290

Arg Asp Leu Gly Gly Arg Asp Asp Leu Leu
1               5                   10

<210> SEQ ID NO 291
<211> LENGTH: 10
<212> TYPE: PRT
<213> ORGANISM: Homo sapiens

<400> SEQUENCE: 291

Asp Leu Gly Gly Arg Asp Asp Leu Leu Tyr
1               5                   10

<210> SEQ ID NO 292
<211> LENGTH: 10
<212> TYPE: PRT
<213> ORGANISM: Homo sapiens

<400> SEQUENCE: 292

Leu Gly Gly Arg Asp Asp Leu Leu Tyr Asn
1               5                   10

<210> SEQ ID NO 293
<211> LENGTH: 10
<212> TYPE: PRT
<213> ORGANISM: Homo sapiens

<400> SEQUENCE: 293

Gly Gly Arg Asp Asp Leu Leu Tyr Asn Val
1               5                   10

<210> SEQ ID NO 294
```

```
<211> LENGTH: 10
<212> TYPE: PRT
<213> ORGANISM: Homo sapiens

<400> SEQUENCE: 294

Gly Arg Asp Asp Leu Leu Tyr Asn Val Ile
1               5                   10

<210> SEQ ID NO 295
<211> LENGTH: 10
<212> TYPE: PRT
<213> ORGANISM: Homo sapiens

<400> SEQUENCE: 295

Arg Asp Asp Leu Leu Tyr Asn Val Ile Cys
1               5                   10

<210> SEQ ID NO 296
<211> LENGTH: 10
<212> TYPE: PRT
<213> ORGANISM: Homo sapiens

<400> SEQUENCE: 296

Asp Asp Leu Leu Tyr Asn Val Ile Cys Lys
1               5                   10

<210> SEQ ID NO 297
<211> LENGTH: 10
<212> TYPE: PRT
<213> ORGANISM: Homo sapiens

<400> SEQUENCE: 297

Asp Leu Leu Tyr Asn Val Ile Cys Lys Lys
1               5                   10

<210> SEQ ID NO 298
<211> LENGTH: 10
<212> TYPE: PRT
<213> ORGANISM: Homo sapiens

<400> SEQUENCE: 298

Leu Leu Tyr Asn Val Ile Cys Lys Lys Cys
1               5                   10

<210> SEQ ID NO 299
<211> LENGTH: 10
<212> TYPE: PRT
<213> ORGANISM: Homo sapiens

<400> SEQUENCE: 299

Leu Tyr Asn Val Ile Cys Lys Lys Cys His
1               5                   10

<210> SEQ ID NO 300
<211> LENGTH: 10
<212> TYPE: PRT
<213> ORGANISM: Homo sapiens

<400> SEQUENCE: 300

Tyr Asn Val Ile Cys Lys Lys Cys His Gly
1               5                   10

<210> SEQ ID NO 301
<211> LENGTH: 10
<212> TYPE: PRT
<213> ORGANISM: Homo sapiens
```

<400> SEQUENCE: 301

Asn Val Ile Cys Lys Lys Cys His Gly Ala
1               5                   10

<210> SEQ ID NO 302
<211> LENGTH: 8
<212> TYPE: PRT
<213> ORGANISM: Homo sapiens

<400> SEQUENCE: 302

Pro Leu Pro Pro Arg Tyr Ala Ala
1               5

<210> SEQ ID NO 303
<211> LENGTH: 8
<212> TYPE: PRT
<213> ORGANISM: Homo sapiens

<400> SEQUENCE: 303

Leu Pro Pro Arg Tyr Ala Ala Val
1               5

<210> SEQ ID NO 304
<211> LENGTH: 8
<212> TYPE: PRT
<213> ORGANISM: Homo sapiens

<400> SEQUENCE: 304

Pro Pro Arg Tyr Ala Ala Val Asn
1               5

<210> SEQ ID NO 305
<211> LENGTH: 8
<212> TYPE: PRT
<213> ORGANISM: Homo sapiens

<400> SEQUENCE: 305

Pro Arg Tyr Ala Ala Val Asn Ile
1               5

<210> SEQ ID NO 306
<211> LENGTH: 8
<212> TYPE: PRT
<213> ORGANISM: Homo sapiens

<400> SEQUENCE: 306

Arg Tyr Ala Ala Val Asn Ile Thr
1               5

<210> SEQ ID NO 307
<211> LENGTH: 8
<212> TYPE: PRT
<213> ORGANISM: Homo sapiens

<400> SEQUENCE: 307

Tyr Ala Ala Val Asn Ile Thr Thr
1               5

<210> SEQ ID NO 308
<211> LENGTH: 8
<212> TYPE: PRT
<213> ORGANISM: Homo sapiens

<400> SEQUENCE: 308

```
Ala Ala Val Asn Ile Thr Thr Asn
1               5

<210> SEQ ID NO 309
<211> LENGTH: 8
<212> TYPE: PRT
<213> ORGANISM: Homo sapiens

<400> SEQUENCE: 309

Ala Val Asn Ile Thr Thr Asn Gln
1               5

<210> SEQ ID NO 310
<211> LENGTH: 8
<212> TYPE: PRT
<213> ORGANISM: Homo sapiens

<400> SEQUENCE: 310

Val Asn Ile Thr Thr Asn Gln Ala
1               5

<210> SEQ ID NO 311
<211> LENGTH: 8
<212> TYPE: PRT
<213> ORGANISM: Homo sapiens

<400> SEQUENCE: 311

Asn Ile Thr Thr Asn Gln Ala Ala
1               5

<210> SEQ ID NO 312
<211> LENGTH: 8
<212> TYPE: PRT
<213> ORGANISM: Homo sapiens

<400> SEQUENCE: 312

Ile Thr Thr Asn Gln Ala Ala Pro
1               5

<210> SEQ ID NO 313
<211> LENGTH: 8
<212> TYPE: PRT
<213> ORGANISM: Homo sapiens

<400> SEQUENCE: 313

Thr Thr Asn Gln Ala Ala Pro Ser
1               5

<210> SEQ ID NO 314
<211> LENGTH: 8
<212> TYPE: PRT
<213> ORGANISM: Homo sapiens

<400> SEQUENCE: 314

Thr Asn Gln Ala Ala Pro Ser Glu
1               5

<210> SEQ ID NO 315
<211> LENGTH: 8
<212> TYPE: PRT
<213> ORGANISM: Homo sapiens

<400> SEQUENCE: 315

Asn Gln Ala Ala Pro Ser Glu Val
1               5
```

<210> SEQ ID NO 316
<211> LENGTH: 8
<212> TYPE: PRT
<213> ORGANISM: Homo sapiens

<400> SEQUENCE: 316

Gln Ala Ala Pro Ser Glu Val Pro
1               5

<210> SEQ ID NO 317
<211> LENGTH: 8
<212> TYPE: PRT
<213> ORGANISM: Homo sapiens

<400> SEQUENCE: 317

Ala Ala Pro Ser Glu Val Pro Thr
1               5

<210> SEQ ID NO 318
<211> LENGTH: 8
<212> TYPE: PRT
<213> ORGANISM: Homo sapiens

<400> SEQUENCE: 318

Ala Pro Ser Glu Val Pro Thr Leu
1               5

<210> SEQ ID NO 319
<211> LENGTH: 8
<212> TYPE: PRT
<213> ORGANISM: Homo sapiens

<400> SEQUENCE: 319

Pro Ser Glu Val Pro Thr Leu Arg
1               5

<210> SEQ ID NO 320
<211> LENGTH: 8
<212> TYPE: PRT
<213> ORGANISM: Homo sapiens

<400> SEQUENCE: 320

Ser Glu Val Pro Thr Leu Arg Leu
1               5

<210> SEQ ID NO 321
<211> LENGTH: 8
<212> TYPE: PRT
<213> ORGANISM: Homo sapiens

<400> SEQUENCE: 321

Glu Val Pro Thr Leu Arg Leu His
1               5

<210> SEQ ID NO 322
<211> LENGTH: 8
<212> TYPE: PRT
<213> ORGANISM: Homo sapiens

<400> SEQUENCE: 322

Val Pro Thr Leu Arg Leu His Ser
1               5

<210> SEQ ID NO 323
<211> LENGTH: 8

```
<212> TYPE: PRT
<213> ORGANISM: Homo sapiens

<400> SEQUENCE: 323

Pro Thr Leu Arg Leu His Ser Ser
1               5

<210> SEQ ID NO 324
<211> LENGTH: 8
<212> TYPE: PRT
<213> ORGANISM: Homo sapiens

<400> SEQUENCE: 324

Thr Leu Arg Leu His Ser Ser Ser
1               5

<210> SEQ ID NO 325
<211> LENGTH: 8
<212> TYPE: PRT
<213> ORGANISM: Homo sapiens

<400> SEQUENCE: 325

Leu Arg Leu His Ser Ser Ser Gly
1               5

<210> SEQ ID NO 326
<211> LENGTH: 8
<212> TYPE: PRT
<213> ORGANISM: Homo sapiens

<400> SEQUENCE: 326

Arg Leu His Ser Ser Ser Gly Ser
1               5

<210> SEQ ID NO 327
<211> LENGTH: 8
<212> TYPE: PRT
<213> ORGANISM: Homo sapiens

<400> SEQUENCE: 327

Leu His Ser Ser Ser Gly Ser Ser
1               5

<210> SEQ ID NO 328
<211> LENGTH: 8
<212> TYPE: PRT
<213> ORGANISM: Homo sapiens

<400> SEQUENCE: 328

His Ser Ser Ser Gly Ser Ser Leu
1               5

<210> SEQ ID NO 329
<211> LENGTH: 9
<212> TYPE: PRT
<213> ORGANISM: Homo sapiens

<400> SEQUENCE: 329

Pro Leu Pro Pro Arg Tyr Ala Ala Val
1               5

<210> SEQ ID NO 330
<211> LENGTH: 9
<212> TYPE: PRT
<213> ORGANISM: Homo sapiens
```

```
<400> SEQUENCE: 330

Leu Pro Pro Arg Tyr Ala Ala Val Asn
1               5

<210> SEQ ID NO 331
<211> LENGTH: 9
<212> TYPE: PRT
<213> ORGANISM: Homo sapiens

<400> SEQUENCE: 331

Pro Pro Arg Tyr Ala Ala Val Asn Ile
1               5

<210> SEQ ID NO 332
<211> LENGTH: 9
<212> TYPE: PRT
<213> ORGANISM: Homo sapiens

<400> SEQUENCE: 332

Pro Arg Tyr Ala Ala Val Asn Ile Thr
1               5

<210> SEQ ID NO 333
<211> LENGTH: 9
<212> TYPE: PRT
<213> ORGANISM: Homo sapiens

<400> SEQUENCE: 333

Arg Tyr Ala Ala Val Asn Ile Thr Thr
1               5

<210> SEQ ID NO 334
<211> LENGTH: 9
<212> TYPE: PRT
<213> ORGANISM: Homo sapiens

<400> SEQUENCE: 334

Tyr Ala Ala Val Asn Ile Thr Thr Asn
1               5

<210> SEQ ID NO 335
<211> LENGTH: 9
<212> TYPE: PRT
<213> ORGANISM: Homo sapiens

<400> SEQUENCE: 335

Ala Ala Val Asn Ile Thr Thr Asn Gln
1               5

<210> SEQ ID NO 336
<211> LENGTH: 9
<212> TYPE: PRT
<213> ORGANISM: Homo sapiens

<400> SEQUENCE: 336

Ala Val Asn Ile Thr Thr Asn Gln Ala
1               5

<210> SEQ ID NO 337
<211> LENGTH: 9
<212> TYPE: PRT
<213> ORGANISM: Homo sapiens

<400> SEQUENCE: 337

Val Asn Ile Thr Thr Asn Gln Ala Ala
```

```
1               5

<210> SEQ ID NO 338
<211> LENGTH: 9
<212> TYPE: PRT
<213> ORGANISM: Homo sapiens

<400> SEQUENCE: 338

Asn Ile Thr Thr Asn Gln Ala Ala Pro
1               5

<210> SEQ ID NO 339
<211> LENGTH: 9
<212> TYPE: PRT
<213> ORGANISM: Homo sapiens

<400> SEQUENCE: 339

Ile Thr Thr Asn Gln Ala Ala Pro Ser
1               5

<210> SEQ ID NO 340
<211> LENGTH: 9
<212> TYPE: PRT
<213> ORGANISM: Homo sapiens

<400> SEQUENCE: 340

Thr Thr Asn Gln Ala Ala Pro Ser Glu
1               5

<210> SEQ ID NO 341
<211> LENGTH: 9
<212> TYPE: PRT
<213> ORGANISM: Homo sapiens

<400> SEQUENCE: 341

Thr Asn Gln Ala Ala Pro Ser Glu Val
1               5

<210> SEQ ID NO 342
<211> LENGTH: 9
<212> TYPE: PRT
<213> ORGANISM: Homo sapiens

<400> SEQUENCE: 342

Asn Gln Ala Ala Pro Ser Glu Val Pro
1               5

<210> SEQ ID NO 343
<211> LENGTH: 9
<212> TYPE: PRT
<213> ORGANISM: Homo sapiens

<400> SEQUENCE: 343

Gln Ala Ala Pro Ser Glu Val Pro Thr
1               5

<210> SEQ ID NO 344
<211> LENGTH: 9
<212> TYPE: PRT
<213> ORGANISM: Homo sapiens

<400> SEQUENCE: 344

Ala Ala Pro Ser Glu Val Pro Thr Leu
1               5
```

```
<210> SEQ ID NO 345
<211> LENGTH: 9
<212> TYPE: PRT
<213> ORGANISM: Homo sapiens

<400> SEQUENCE: 345

Ala Pro Ser Glu Val Pro Thr Leu Arg
1               5

<210> SEQ ID NO 346
<211> LENGTH: 9
<212> TYPE: PRT
<213> ORGANISM: Homo sapiens

<400> SEQUENCE: 346

Pro Ser Glu Val Pro Thr Leu Arg Leu
1               5

<210> SEQ ID NO 347
<211> LENGTH: 9
<212> TYPE: PRT
<213> ORGANISM: Homo sapiens

<400> SEQUENCE: 347

Ser Glu Val Pro Thr Leu Arg Leu His
1               5

<210> SEQ ID NO 348
<211> LENGTH: 9
<212> TYPE: PRT
<213> ORGANISM: Homo sapiens

<400> SEQUENCE: 348

Glu Val Pro Thr Leu Arg Leu His Ser
1               5

<210> SEQ ID NO 349
<211> LENGTH: 9
<212> TYPE: PRT
<213> ORGANISM: Homo sapiens

<400> SEQUENCE: 349

Val Pro Thr Leu Arg Leu His Ser Ser
1               5

<210> SEQ ID NO 350
<211> LENGTH: 9
<212> TYPE: PRT
<213> ORGANISM: Homo sapiens

<400> SEQUENCE: 350

Pro Thr Leu Arg Leu His Ser Ser Ser
1               5

<210> SEQ ID NO 351
<211> LENGTH: 9
<212> TYPE: PRT
<213> ORGANISM: Homo sapiens

<400> SEQUENCE: 351

Thr Leu Arg Leu His Ser Ser Ser Gly
1               5

<210> SEQ ID NO 352
<211> LENGTH: 9
<212> TYPE: PRT
```

<213> ORGANISM: Homo sapiens

<400> SEQUENCE: 352

Leu Arg Leu His Ser Ser Ser Gly Ser
1               5

<210> SEQ ID NO 353
<211> LENGTH: 9
<212> TYPE: PRT
<213> ORGANISM: Homo sapiens

<400> SEQUENCE: 353

Arg Leu His Ser Ser Ser Gly Ser Ser
1               5

<210> SEQ ID NO 354
<211> LENGTH: 9
<212> TYPE: PRT
<213> ORGANISM: Homo sapiens

<400> SEQUENCE: 354

Leu His Ser Ser Ser Gly Ser Ser Leu
1               5

<210> SEQ ID NO 355
<211> LENGTH: 10
<212> TYPE: PRT
<213> ORGANISM: Homo sapiens

<400> SEQUENCE: 355

Pro Leu Pro Pro Arg Tyr Ala Ala Val Asn
1               5                   10

<210> SEQ ID NO 356
<211> LENGTH: 10
<212> TYPE: PRT
<213> ORGANISM: Homo sapiens

<400> SEQUENCE: 356

Leu Pro Pro Arg Tyr Ala Ala Val Asn Ile
1               5                   10

<210> SEQ ID NO 357
<211> LENGTH: 10
<212> TYPE: PRT
<213> ORGANISM: Homo sapiens

<400> SEQUENCE: 357

Pro Pro Arg Tyr Ala Ala Val Asn Ile Thr
1               5                   10

<210> SEQ ID NO 358
<211> LENGTH: 10
<212> TYPE: PRT
<213> ORGANISM: Homo sapiens

<400> SEQUENCE: 358

Pro Arg Tyr Ala Ala Val Asn Ile Thr Thr
1               5                   10

<210> SEQ ID NO 359
<211> LENGTH: 10
<212> TYPE: PRT
<213> ORGANISM: Homo sapiens

<400> SEQUENCE: 359

Arg Tyr Ala Ala Val Asn Ile Thr Thr Asn
1               5                   10

<210> SEQ ID NO 360
<211> LENGTH: 10
<212> TYPE: PRT
<213> ORGANISM: Homo sapiens

<400> SEQUENCE: 360

Tyr Ala Ala Val Asn Ile Thr Thr Asn Gln
1               5                   10

<210> SEQ ID NO 361
<211> LENGTH: 10
<212> TYPE: PRT
<213> ORGANISM: Homo sapiens

<400> SEQUENCE: 361

Ala Ala Val Asn Ile Thr Thr Asn Gln Ala
1               5                   10

<210> SEQ ID NO 362
<211> LENGTH: 10
<212> TYPE: PRT
<213> ORGANISM: Homo sapiens

<400> SEQUENCE: 362

Ala Val Asn Ile Thr Thr Asn Gln Ala Ala
1               5                   10

<210> SEQ ID NO 363
<211> LENGTH: 10
<212> TYPE: PRT
<213> ORGANISM: Homo sapiens

<400> SEQUENCE: 363

Val Asn Ile Thr Thr Asn Gln Ala Ala Pro
1               5                   10

<210> SEQ ID NO 364
<211> LENGTH: 10
<212> TYPE: PRT
<213> ORGANISM: Homo sapiens

<400> SEQUENCE: 364

Asn Ile Thr Thr Asn Gln Ala Ala Pro Ser
1               5                   10

<210> SEQ ID NO 365
<211> LENGTH: 10
<212> TYPE: PRT
<213> ORGANISM: Homo sapiens

<400> SEQUENCE: 365

Ile Thr Thr Asn Gln Ala Ala Pro Ser Glu
1               5                   10

<210> SEQ ID NO 366
<211> LENGTH: 10
<212> TYPE: PRT
<213> ORGANISM: Homo sapiens

<400> SEQUENCE: 366

Thr Thr Asn Gln Ala Ala Pro Ser Glu Val
1               5                   10

```
<210> SEQ ID NO 367
<211> LENGTH: 10
<212> TYPE: PRT
<213> ORGANISM: Homo sapiens

<400> SEQUENCE: 367

Thr Asn Gln Ala Ala Pro Ser Glu Val Pro
1               5                   10

<210> SEQ ID NO 368
<211> LENGTH: 10
<212> TYPE: PRT
<213> ORGANISM: Homo sapiens

<400> SEQUENCE: 368

Asn Gln Ala Ala Pro Ser Glu Val Pro Thr
1               5                   10

<210> SEQ ID NO 369
<211> LENGTH: 10
<212> TYPE: PRT
<213> ORGANISM: Homo sapiens

<400> SEQUENCE: 369

Gln Ala Ala Pro Ser Glu Val Pro Thr Leu
1               5                   10

<210> SEQ ID NO 370
<211> LENGTH: 10
<212> TYPE: PRT
<213> ORGANISM: Homo sapiens

<400> SEQUENCE: 370

Ala Ala Pro Ser Glu Val Pro Thr Leu Arg
1               5                   10

<210> SEQ ID NO 371
<211> LENGTH: 10
<212> TYPE: PRT
<213> ORGANISM: Homo sapiens

<400> SEQUENCE: 371

Ala Pro Ser Glu Val Pro Thr Leu Arg Leu
1               5                   10

<210> SEQ ID NO 372
<211> LENGTH: 10
<212> TYPE: PRT
<213> ORGANISM: Homo sapiens

<400> SEQUENCE: 372

Pro Ser Glu Val Pro Thr Leu Arg Leu His
1               5                   10

<210> SEQ ID NO 373
<211> LENGTH: 10
<212> TYPE: PRT
<213> ORGANISM: Homo sapiens

<400> SEQUENCE: 373

Ser Glu Val Pro Thr Leu Arg Leu His Ser
1               5                   10

<210> SEQ ID NO 374
```

```
<211> LENGTH: 10
<212> TYPE: PRT
<213> ORGANISM: Homo sapiens

<400> SEQUENCE: 374

Glu Val Pro Thr Leu Arg Leu His Ser Ser
1               5                   10

<210> SEQ ID NO 375
<211> LENGTH: 10
<212> TYPE: PRT
<213> ORGANISM: Homo sapiens

<400> SEQUENCE: 375

Val Pro Thr Leu Arg Leu His Ser Ser Ser
1               5                   10

<210> SEQ ID NO 376
<211> LENGTH: 10
<212> TYPE: PRT
<213> ORGANISM: Homo sapiens

<400> SEQUENCE: 376

Pro Thr Leu Arg Leu His Ser Ser Ser Gly
1               5                   10

<210> SEQ ID NO 377
<211> LENGTH: 10
<212> TYPE: PRT
<213> ORGANISM: Homo sapiens

<400> SEQUENCE: 377

Thr Leu Arg Leu His Ser Ser Ser Gly Ser
1               5                   10

<210> SEQ ID NO 378
<211> LENGTH: 10
<212> TYPE: PRT
<213> ORGANISM: Homo sapiens

<400> SEQUENCE: 378

Leu Arg Leu His Ser Ser Ser Gly Ser Ser
1               5                   10

<210> SEQ ID NO 379
<211> LENGTH: 10
<212> TYPE: PRT
<213> ORGANISM: Homo sapiens

<400> SEQUENCE: 379

Arg Leu His Ser Ser Ser Gly Ser Ser Leu
1               5                   10

<210> SEQ ID NO 380
<211> LENGTH: 8
<212> TYPE: PRT
<213> ORGANISM: Homo sapiens

<400> SEQUENCE: 380

Gln Leu Asp Gly Leu Arg Pro Asp
1               5

<210> SEQ ID NO 381
<211> LENGTH: 8
<212> TYPE: PRT
<213> ORGANISM: Homo sapiens
```

<400> SEQUENCE: 381

Leu Asp Gly Leu Arg Pro Asp Ala
1               5

<210> SEQ ID NO 382
<211> LENGTH: 8
<212> TYPE: PRT
<213> ORGANISM: Homo sapiens

<400> SEQUENCE: 382

Asp Gly Leu Arg Pro Asp Ala Arg
1               5

<210> SEQ ID NO 383
<211> LENGTH: 8
<212> TYPE: PRT
<213> ORGANISM: Homo sapiens

<400> SEQUENCE: 383

Gly Leu Arg Pro Asp Ala Arg Tyr
1               5

<210> SEQ ID NO 384
<211> LENGTH: 8
<212> TYPE: PRT
<213> ORGANISM: Homo sapiens

<400> SEQUENCE: 384

Leu Arg Pro Asp Ala Arg Tyr Val
1               5

<210> SEQ ID NO 385
<211> LENGTH: 8
<212> TYPE: PRT
<213> ORGANISM: Homo sapiens

<400> SEQUENCE: 385

Arg Pro Asp Ala Arg Tyr Val Val
1               5

<210> SEQ ID NO 386
<211> LENGTH: 8
<212> TYPE: PRT
<213> ORGANISM: Homo sapiens

<400> SEQUENCE: 386

Pro Asp Ala Arg Tyr Val Val Gln
1               5

<210> SEQ ID NO 387
<211> LENGTH: 8
<212> TYPE: PRT
<213> ORGANISM: Homo sapiens

<400> SEQUENCE: 387

Asp Ala Arg Tyr Val Val Gln Val
1               5

<210> SEQ ID NO 388
<211> LENGTH: 8
<212> TYPE: PRT
<213> ORGANISM: Homo sapiens

<400> SEQUENCE: 388

Ala Arg Tyr Val Val Gln Val Arg
1               5

<210> SEQ ID NO 389
<211> LENGTH: 8
<212> TYPE: PRT
<213> ORGANISM: Homo sapiens

<400> SEQUENCE: 389

Arg Tyr Val Val Gln Val Arg Ala
1               5

<210> SEQ ID NO 390
<211> LENGTH: 8
<212> TYPE: PRT
<213> ORGANISM: Homo sapiens

<400> SEQUENCE: 390

Tyr Val Val Gln Val Arg Ala Arg
1               5

<210> SEQ ID NO 391
<211> LENGTH: 8
<212> TYPE: PRT
<213> ORGANISM: Homo sapiens

<400> SEQUENCE: 391

Val Val Gln Val Arg Ala Arg Thr
1               5

<210> SEQ ID NO 392
<211> LENGTH: 8
<212> TYPE: PRT
<213> ORGANISM: Homo sapiens

<400> SEQUENCE: 392

Val Gln Val Arg Ala Arg Thr Val
1               5

<210> SEQ ID NO 393
<211> LENGTH: 8
<212> TYPE: PRT
<213> ORGANISM: Homo sapiens

<400> SEQUENCE: 393

Gln Val Arg Ala Arg Thr Val Ala
1               5

<210> SEQ ID NO 394
<211> LENGTH: 8
<212> TYPE: PRT
<213> ORGANISM: Homo sapiens

<400> SEQUENCE: 394

Val Arg Ala Arg Thr Val Ala Gly
1               5

<210> SEQ ID NO 395
<211> LENGTH: 9
<212> TYPE: PRT
<213> ORGANISM: Homo sapiens

<400> SEQUENCE: 395

Gln Leu Asp Gly Leu Arg Pro Asp Ala
1               5

<210> SEQ ID NO 396
<211> LENGTH: 9
<212> TYPE: PRT
<213> ORGANISM: Homo sapiens

<400> SEQUENCE: 396

Leu Asp Gly Leu Arg Pro Asp Ala Arg
1               5

<210> SEQ ID NO 397
<211> LENGTH: 9
<212> TYPE: PRT
<213> ORGANISM: Homo sapiens

<400> SEQUENCE: 397

Asp Gly Leu Arg Pro Asp Ala Arg Tyr
1               5

<210> SEQ ID NO 398
<211> LENGTH: 9
<212> TYPE: PRT
<213> ORGANISM: Homo sapiens

<400> SEQUENCE: 398

Gly Leu Arg Pro Asp Ala Arg Tyr Val
1               5

<210> SEQ ID NO 399
<211> LENGTH: 9
<212> TYPE: PRT
<213> ORGANISM: Homo sapiens

<400> SEQUENCE: 399

Leu Arg Pro Asp Ala Arg Tyr Val Val
1               5

<210> SEQ ID NO 400
<211> LENGTH: 9
<212> TYPE: PRT
<213> ORGANISM: Homo sapiens

<400> SEQUENCE: 400

Arg Pro Asp Ala Arg Tyr Val Val Gln
1               5

<210> SEQ ID NO 401
<211> LENGTH: 9
<212> TYPE: PRT
<213> ORGANISM: Homo sapiens

<400> SEQUENCE: 401

Pro Asp Ala Arg Tyr Val Val Gln Val
1               5

<210> SEQ ID NO 402
<211> LENGTH: 9
<212> TYPE: PRT
<213> ORGANISM: Homo sapiens

<400> SEQUENCE: 402

Asp Ala Arg Tyr Val Val Gln Val Arg
1               5

<210> SEQ ID NO 403
<211> LENGTH: 9

```
<212> TYPE: PRT
<213> ORGANISM: Homo sapiens

<400> SEQUENCE: 403

Ala Arg Tyr Val Val Gln Val Arg Ala
1               5

<210> SEQ ID NO 404
<211> LENGTH: 9
<212> TYPE: PRT
<213> ORGANISM: Homo sapiens

<400> SEQUENCE: 404

Arg Tyr Val Val Gln Val Arg Ala Arg
1               5

<210> SEQ ID NO 405
<211> LENGTH: 9
<212> TYPE: PRT
<213> ORGANISM: Homo sapiens

<400> SEQUENCE: 405

Tyr Val Val Gln Val Arg Ala Arg Thr
1               5

<210> SEQ ID NO 406
<211> LENGTH: 9
<212> TYPE: PRT
<213> ORGANISM: Homo sapiens

<400> SEQUENCE: 406

Val Val Gln Val Arg Ala Arg Thr Val
1               5

<210> SEQ ID NO 407
<211> LENGTH: 9
<212> TYPE: PRT
<213> ORGANISM: Homo sapiens

<400> SEQUENCE: 407

Val Gln Val Arg Ala Arg Thr Val Ala
1               5

<210> SEQ ID NO 408
<211> LENGTH: 9
<212> TYPE: PRT
<213> ORGANISM: Homo sapiens

<400> SEQUENCE: 408

Gln Val Arg Ala Arg Thr Val Ala Gly
1               5

<210> SEQ ID NO 409
<211> LENGTH: 10
<212> TYPE: PRT
<213> ORGANISM: Homo sapiens

<400> SEQUENCE: 409

Gln Leu Asp Gly Leu Arg Pro Asp Ala Arg
1               5                   10

<210> SEQ ID NO 410
<211> LENGTH: 10
<212> TYPE: PRT
<213> ORGANISM: Homo sapiens
```

```
<400> SEQUENCE: 410

Leu Asp Gly Leu Arg Pro Asp Ala Arg Tyr
1               5                   10

<210> SEQ ID NO 411
<211> LENGTH: 10
<212> TYPE: PRT
<213> ORGANISM: Homo sapiens

<400> SEQUENCE: 411

Asp Gly Leu Arg Pro Asp Ala Arg Tyr Val
1               5                   10

<210> SEQ ID NO 412
<211> LENGTH: 10
<212> TYPE: PRT
<213> ORGANISM: Homo sapiens

<400> SEQUENCE: 412

Gly Leu Arg Pro Asp Ala Arg Tyr Val Val
1               5                   10

<210> SEQ ID NO 413
<211> LENGTH: 10
<212> TYPE: PRT
<213> ORGANISM: Homo sapiens

<400> SEQUENCE: 413

Leu Arg Pro Asp Ala Arg Tyr Val Val Gln
1               5                   10

<210> SEQ ID NO 414
<211> LENGTH: 10
<212> TYPE: PRT
<213> ORGANISM: Homo sapiens

<400> SEQUENCE: 414

Arg Pro Asp Ala Arg Tyr Val Val Gln Val
1               5                   10

<210> SEQ ID NO 415
<211> LENGTH: 10
<212> TYPE: PRT
<213> ORGANISM: Homo sapiens

<400> SEQUENCE: 415

Pro Asp Ala Arg Tyr Val Val Gln Val Arg
1               5                   10

<210> SEQ ID NO 416
<211> LENGTH: 10
<212> TYPE: PRT
<213> ORGANISM: Homo sapiens

<400> SEQUENCE: 416

Asp Ala Arg Tyr Val Val Gln Val Arg Ala
1               5                   10

<210> SEQ ID NO 417
<211> LENGTH: 10
<212> TYPE: PRT
<213> ORGANISM: Homo sapiens

<400> SEQUENCE: 417

Ala Arg Tyr Val Val Gln Val Arg Ala Arg
```

<210> SEQ ID NO 418
<211> LENGTH: 10
<212> TYPE: PRT
<213> ORGANISM: Homo sapiens

<400> SEQUENCE: 418

Arg Tyr Val Val Gln Val Arg Ala Arg Thr
1               5                   10

<210> SEQ ID NO 419
<211> LENGTH: 10
<212> TYPE: PRT
<213> ORGANISM: Homo sapiens

<400> SEQUENCE: 419

Tyr Val Val Gln Val Arg Ala Arg Thr Val
1               5                   10

<210> SEQ ID NO 420
<211> LENGTH: 10
<212> TYPE: PRT
<213> ORGANISM: Homo sapiens

<400> SEQUENCE: 420

Val Val Gln Val Arg Ala Arg Thr Val Ala
1               5                   10

<210> SEQ ID NO 421
<211> LENGTH: 10
<212> TYPE: PRT
<213> ORGANISM: Homo sapiens

<400> SEQUENCE: 421

Val Gln Val Arg Ala Arg Thr Val Ala Gly
1               5                   10

<210> SEQ ID NO 422
<211> LENGTH: 52
<212> TYPE: DNA
<213> ORGANISM: Homo sapiens

<400> SEQUENCE: 422
tcgtatacat ttcttacatc tatgcgctgg aagagaccct catggacaca aa          52

<210> SEQ ID NO 423
<211> LENGTH: 108
<212> TYPE: DNA
<213> ORGANISM: Homo sapiens

<400> SEQUENCE: 423
gggacaagtt tgtacaaaaa agcaggctac gaaggagata tacatatgaa attcttagtc    60
aacgttgccc ttgttttat ggtcgtatac atttcttaca tctatgcg                108

<210> SEQ ID NO 424
<211> LENGTH: 54
<212> TYPE: DNA
<213> ORGANISM: Homo sapiens

<400> SEQUENCE: 424
cgggtcgtcg aggtcctcgt cgaagggcct cgtgtagtgg tagtggtagt gcct          54

<210> SEQ ID NO 425

<211> LENGTH: 61
<212> TYPE: DNA
<213> ORGANISM: Homo sapiens

<400> SEQUENCE: 425
cctcgtgtag tggtagtggt agtgcctcga atttgggtcg aaagaacatg tttcaccagg    60
g    61

<210> SEQ ID NO 426
<211> LENGTH: 15
<212> TYPE: PRT
<213> ORGANISM: Artificial Sequence
<220> FEATURE:
<223> OTHER INFORMATION: Synthetic peptide

<400> SEQUENCE: 426

Ala Lys Lys Leu Val His Thr Pro Tyr Ser Phe Lys Glu Asp Phe
1               5                   10                  15

<210> SEQ ID NO 427
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 427

Ala Lys Xaa Leu Val Xaa Thr Pro Xaa Ser Phe Xaa Glu Asp Xaa
1               5                   10                  15

<210> SEQ ID NO 428
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:

-continued

```
<221> NAME/KEY: misc_feature
<222> LOCATION: (15)..(15)
<223> OTHER INFORMATION: Xaa can be any naturally occurring amino acid

<400> SEQUENCE: 428

Ala Tyr Xaa Leu Tyr Xaa Thr Tyr Xaa Ser Tyr Xaa Glu Tyr Xaa
1               5                   10                  15

<210> SEQ ID NO 429
<211> LENGTH: 9
<212> TYPE: PRT
<213> ORGANISM: Artificial Sequence
<220> FEATURE:
<223> OTHER INFORMATION: Synthetic peptide

<400> SEQUENCE: 429

Cys Tyr Gly Gly Arg Gly Asp Thr Pro
1               5
```